United States Patent
Shatz et al.

(10) Patent No.: US 10,138,286 B2
(45) Date of Patent: Nov. 27, 2018

(54) METHODS AND COMPOSITIONS FOR INHIBITING THE EFFECTS OF AMYLOID BETA OLIGOMERS

(71) Applicant: The Board of Trustees of the Leland Stanford Junior University, Stanford, CA (US)

(72) Inventors: Carla J. Shatz, Palo Alto, CA (US); Taeho Kim, Lexington, MA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/772,357

(22) PCT Filed: Mar. 10, 2014

(86) PCT No.: PCT/US2014/022674
§ 371 (c)(1),
(2) Date: Sep. 2, 2015

(87) PCT Pub. No.: WO2014/164519
PCT Pub. Date: Oct. 9, 2014

(65) Prior Publication Data
US 2016/0009782 A1 Jan. 14, 2016

Related U.S. Application Data

(60) Provisional application No. 61/777,835, filed on Mar. 12, 2013.

(51) Int. Cl.
*C07K 14/705* (2006.01)
*A61K 38/17* (2006.01)
*A61K 38/00* (2006.01)

(52) U.S. Cl.
CPC .... *C07K 14/70503* (2013.01); *A61K 38/1774* (2013.01); *A61K 38/00* (2013.01); *C07K 2319/30* (2013.01); *C07K 2319/70* (2013.01)

(58) Field of Classification Search
CPC ............... A61K 38/00; A61K 38/1774; C07K 2319/30; C07K 2319/70; C07K 14/70503
See application file for complete search history.

(56) References Cited

U.S. PATENT DOCUMENTS

| | | |
|---|---|---|
| 2009/0098109 A1 | 4/2009 | Shatz et al. |
| 2009/0226457 A1 | 9/2009 | Cosman |
| 2009/0285803 A1 | 11/2009 | Atwal et al. |
| 2012/0148495 A1 | 6/2012 | Hensch |

OTHER PUBLICATIONS https://en.wikipedia.org/wiki/LILRB2, retrieved Dec. 8, 2017.*
Ghiso et al., "Alzheimer's Disease and Glaucoma: Mechanistic Similarities and Differences", J. Glaucoma (NIH Public Access), 2013, pp. S36-S38, vol. 22, (Suppl 5), Abstract, Lippincott Williams & Wilkins, Philadelphia, PA.
Park et al., "Alterations of the synapse of the inner retinal layers after chronic intraocular-pressure elevation in glaucoma animal model", Molecular Brain, Aug. 2014, pp. 1-10, vol. 7:53., Abstract, BioMed Central Ltd., London, United Kingdom.
Heimel et al., "The Role of GABAergic Inhibition in Ocular Dominance Plasticity", Neural Plasticity, May 27, 2011, pp. 1-12, vol. 2011, Article ID 391763, Abstract, Hindawi Publishing Corporation, Cairo, Egypt.
Kim, et al. Human LilrB2 is a [beta]-amyloid receptor and its murine homolog PirB regulates synaptic plasticity in an Alzheimer's model. Science Sep. 20, 2013, 341(6152):1399-404.
Chen et al. "Crystal structure of myeloid cell activating receptor leukocyte Ig-like receptor A2, (LILRA2/ILT1/LIR-7) domain swapped dimer: molecular basis for its non-binding to MHC complexes" J. Mol. Biol. (2009) 386, 841?853; p. 842, col. 1, 1st paragraph.

* cited by examiner

*Primary Examiner* — Gregory S Emch
(74) *Attorney, Agent, or Firm* — Pamela J. Sherwood; Bozicevic, Field & Francis LLP

(57) ABSTRACT

Methods and compositions are provided for reducing the effects of amyloid beta (Aβ) oligomers on a cell. Aspects of the methods generally include providing an agent that prevents Aβ oligomer activation of PirB/LILRB2 protein on cells, or providing a PirB/LILRB2 polypeptide composition to cells to prevent the Aβ oligomer activation of cells mediated by non-PirB/LILRB2 receptors. These methods find many uses, for example, in treating the decline in CNS function in individuals suffering from an Aβ-associated disease or disorder, and for screening candidate agents to identify new therapeutics that interfere with these toxic effects of Aβ in individuals having an Aβ-associated disease or disorder.

3 Claims, 28 Drawing Sheets
(13 of 28 Drawing Sheet(s) Filed in Color)
Specification includes a Sequence Listing.

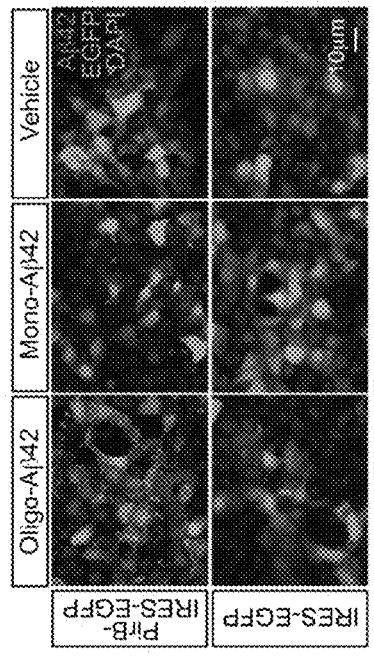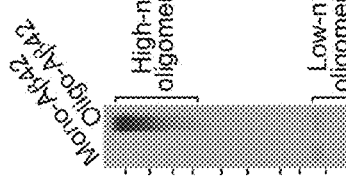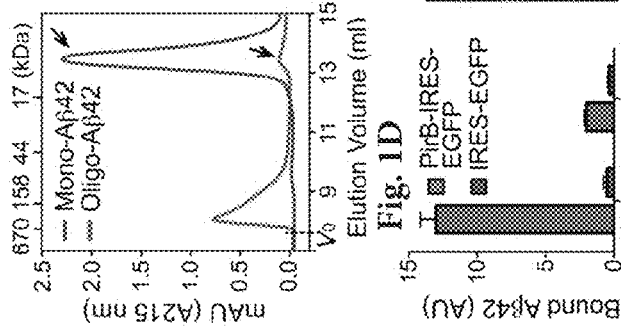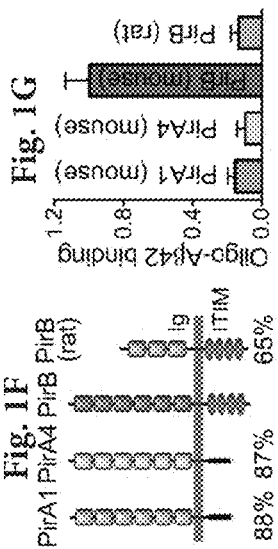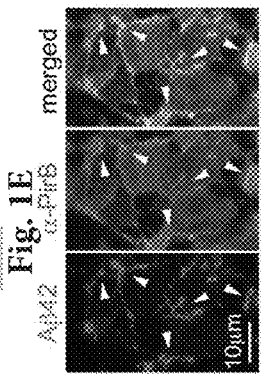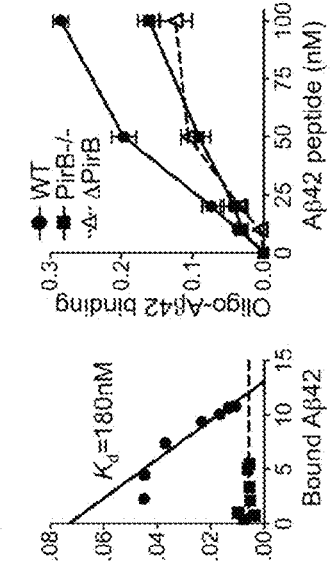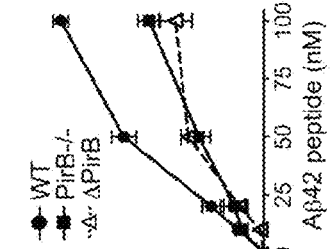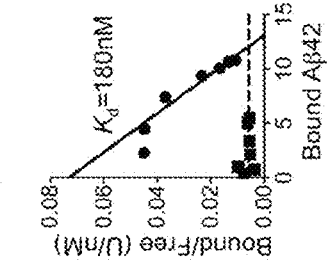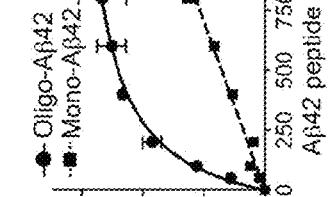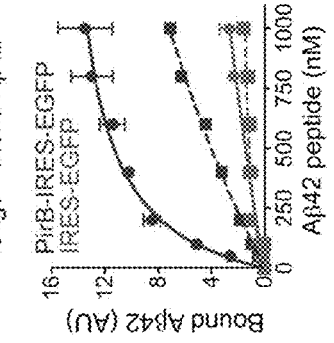

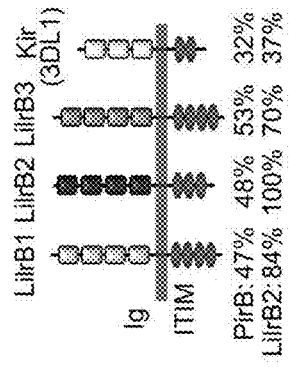

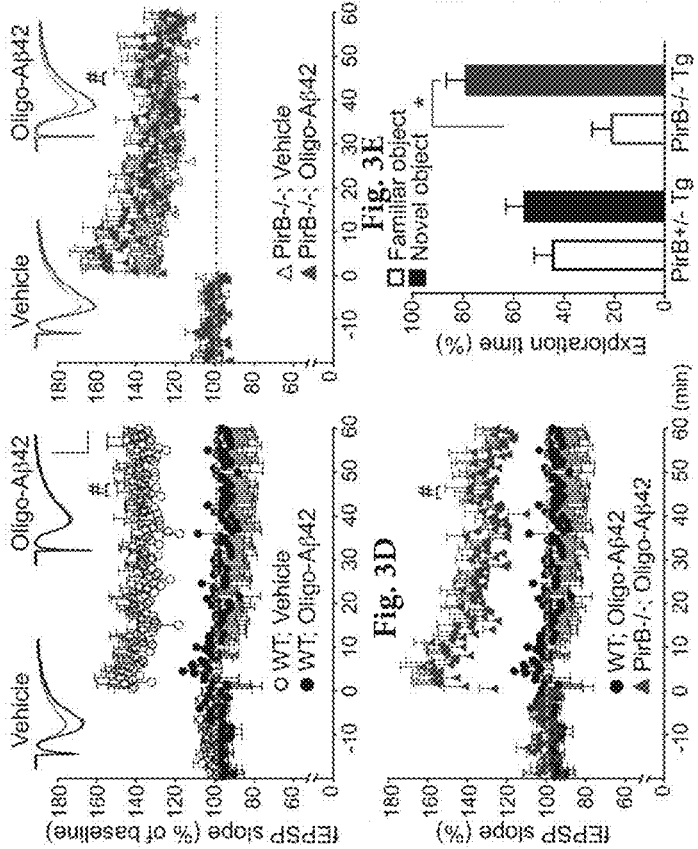

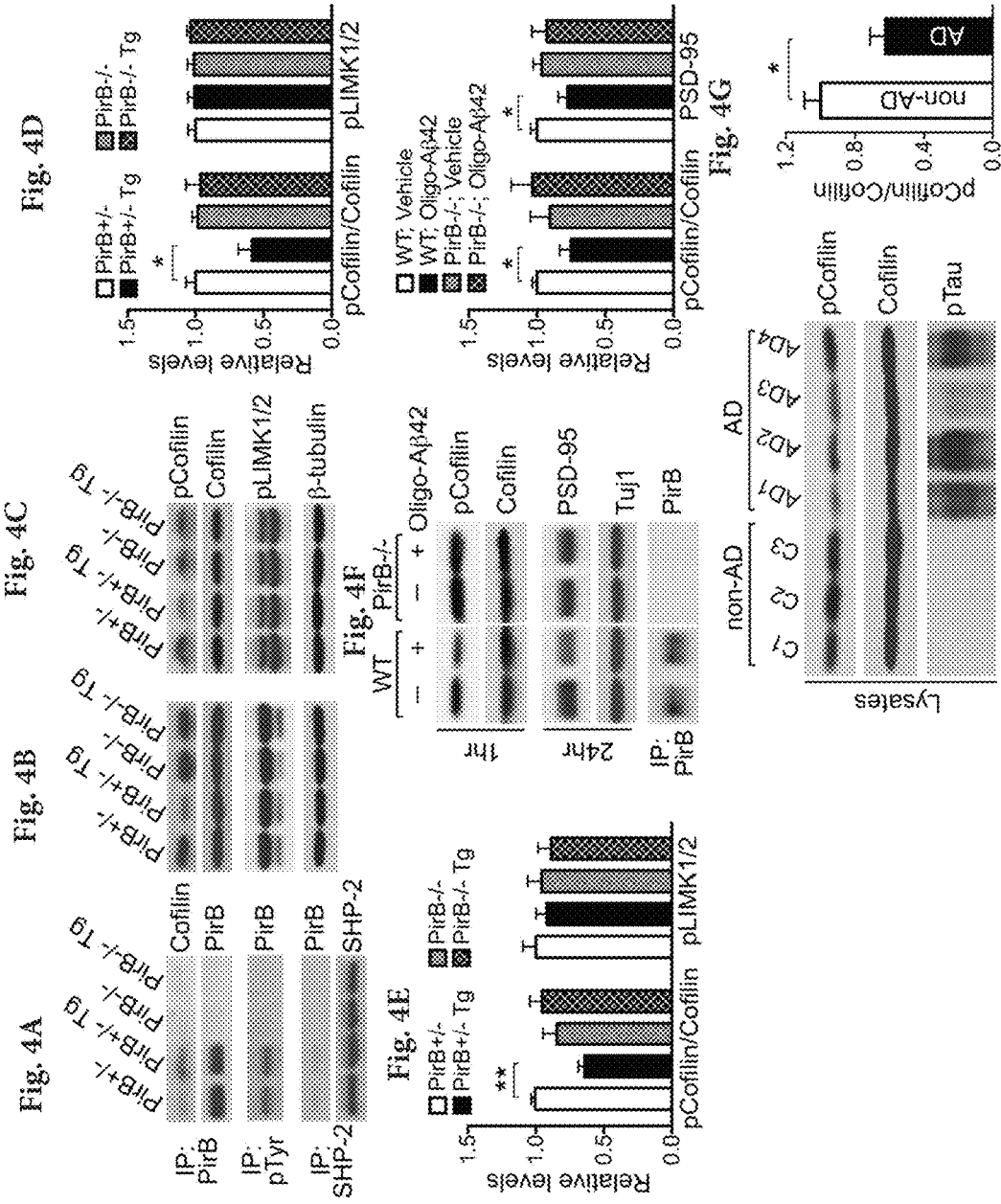

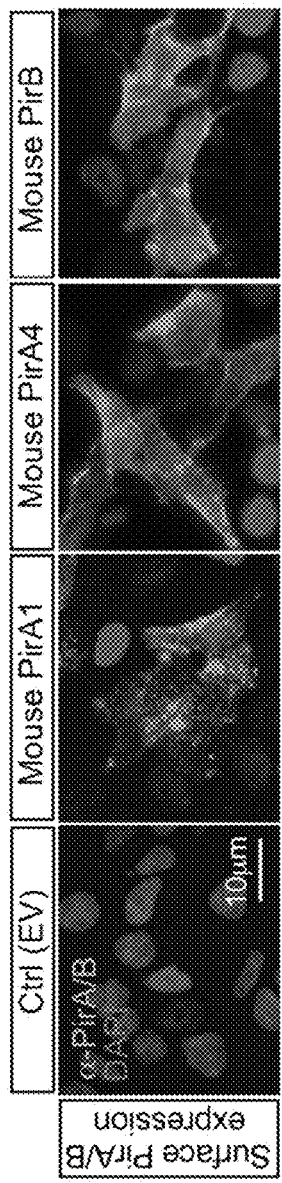
Fig. 7A
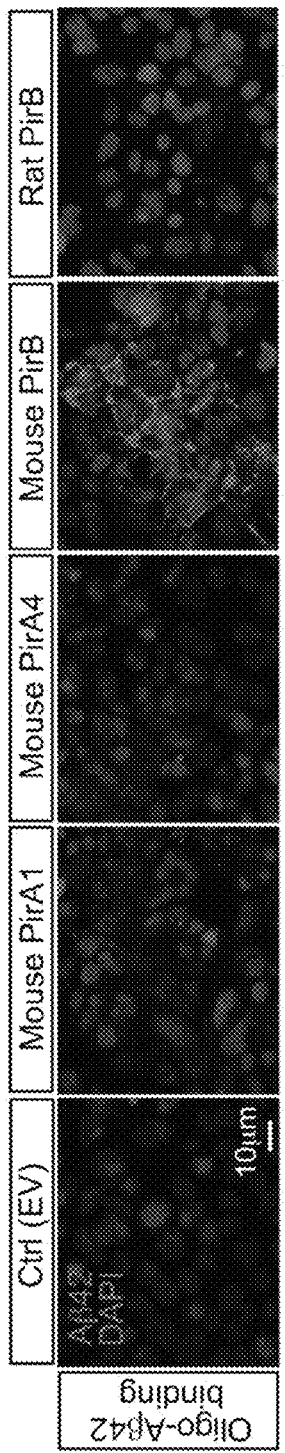
Figure 7B
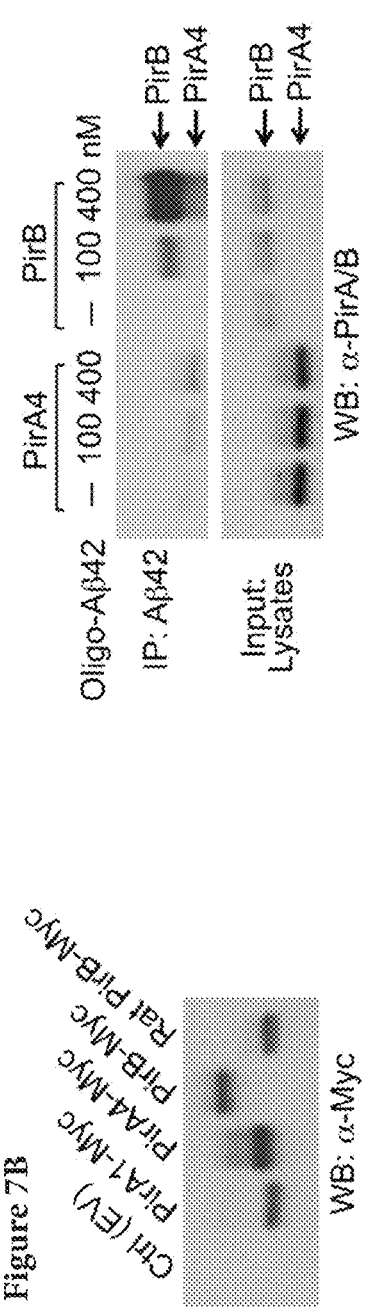
Fig. 7C
Figure 7D

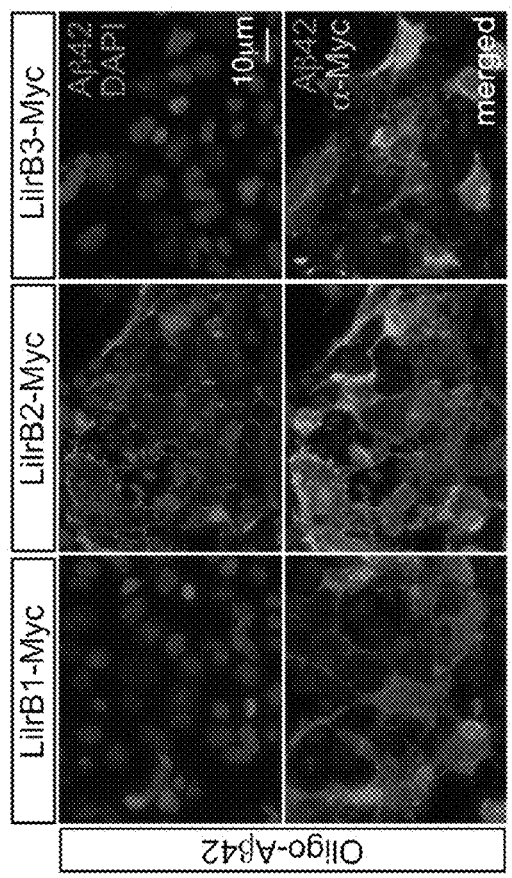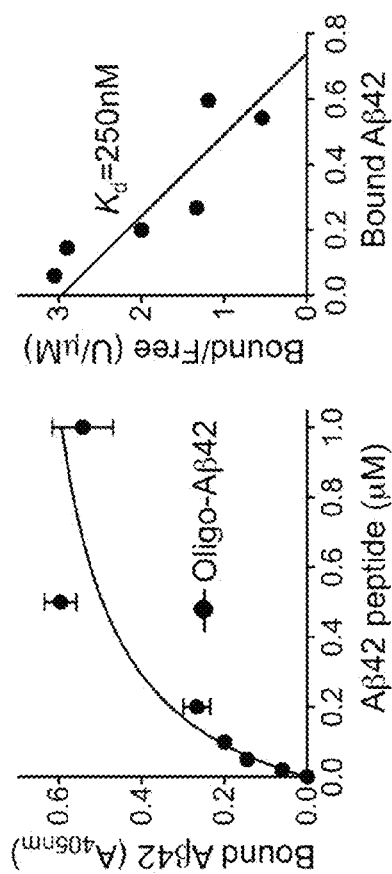
Fig. 9A
Fig. 9B
Fig. 9C

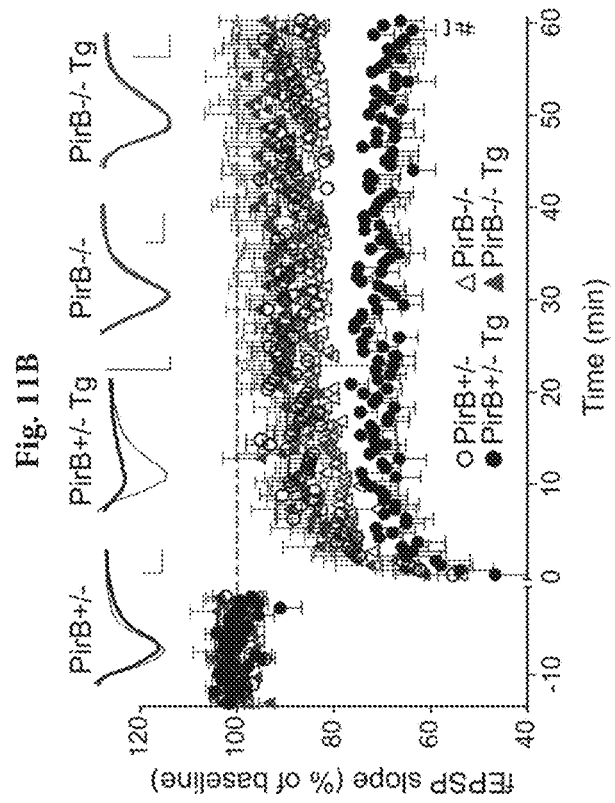
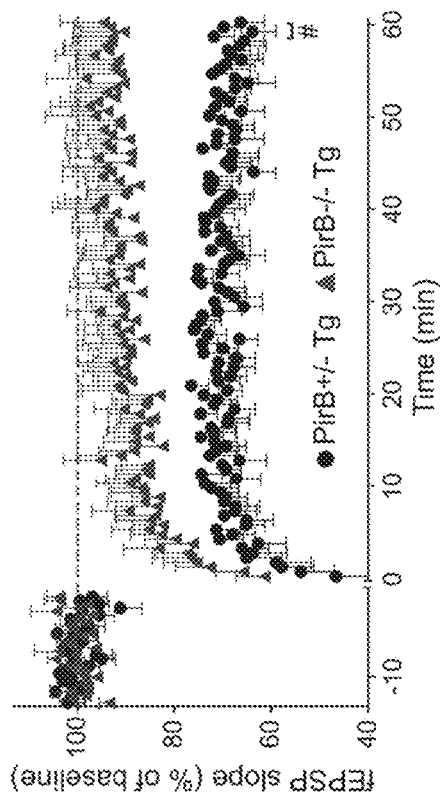
Fig. 11B
Fig. 11D
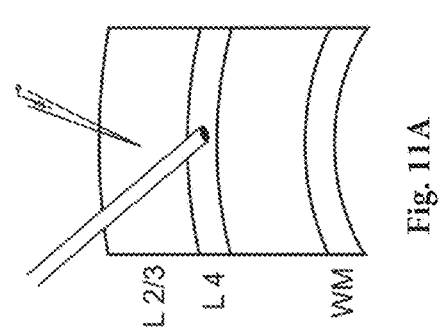
Fig. 11A
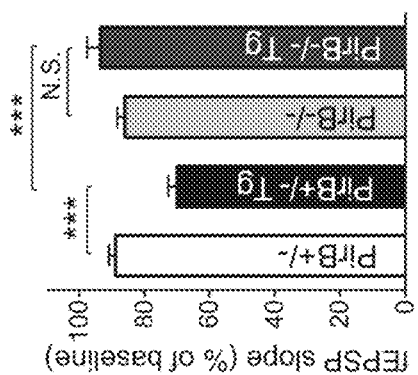
Fig. 11C

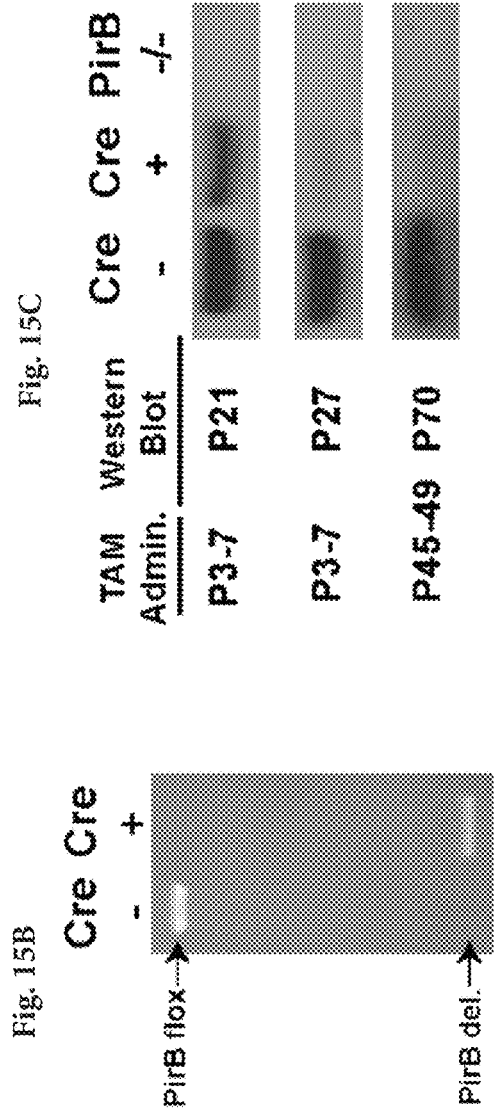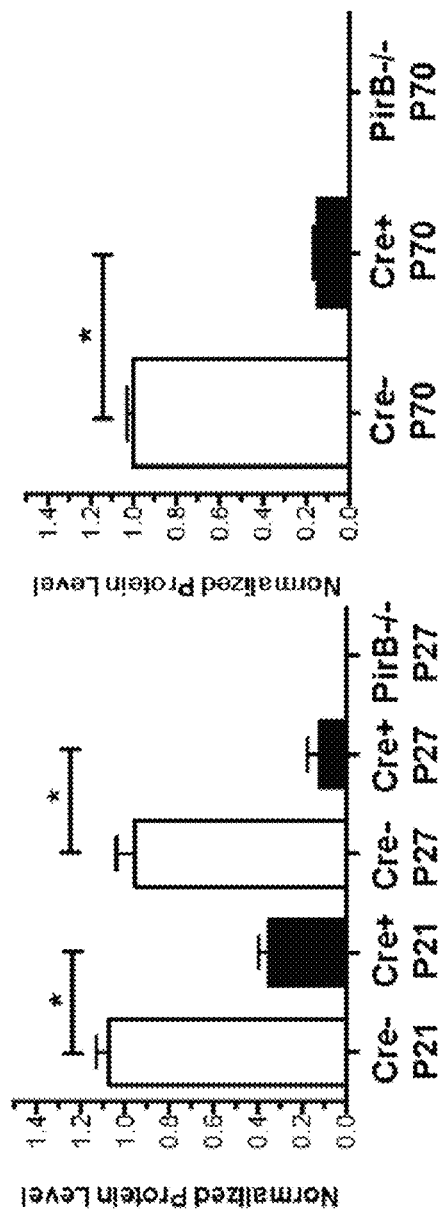

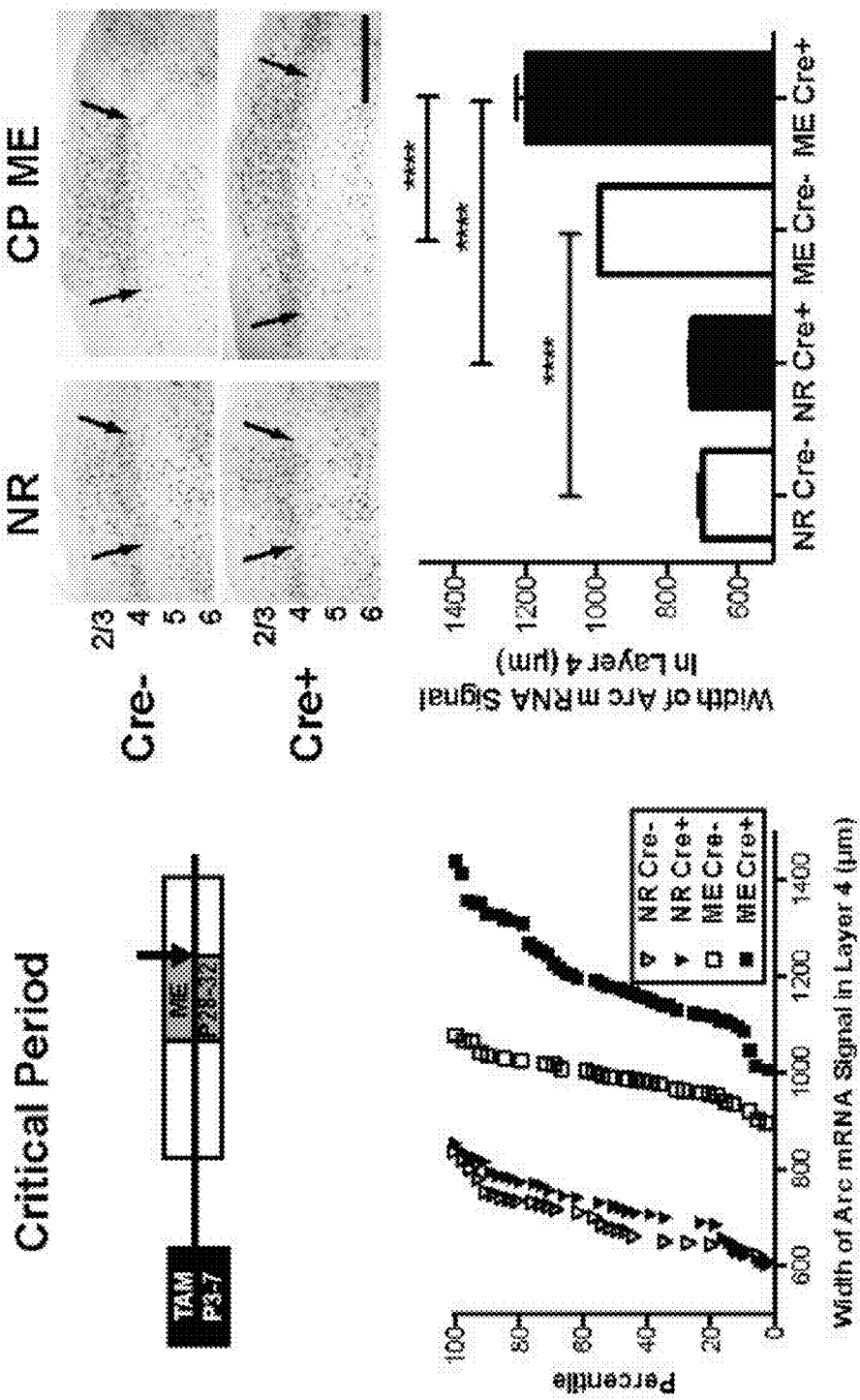
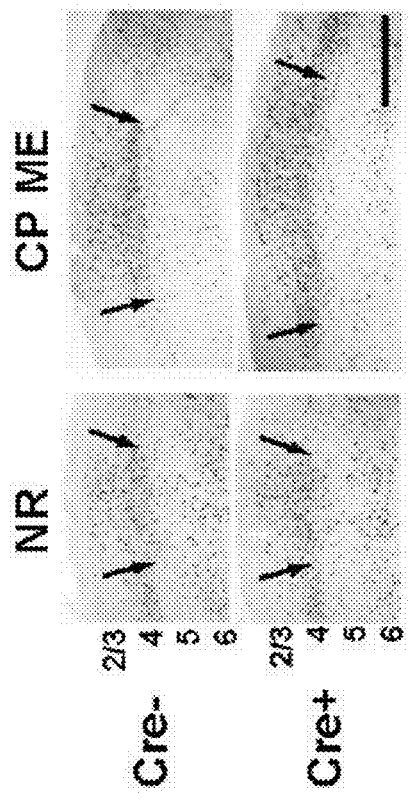
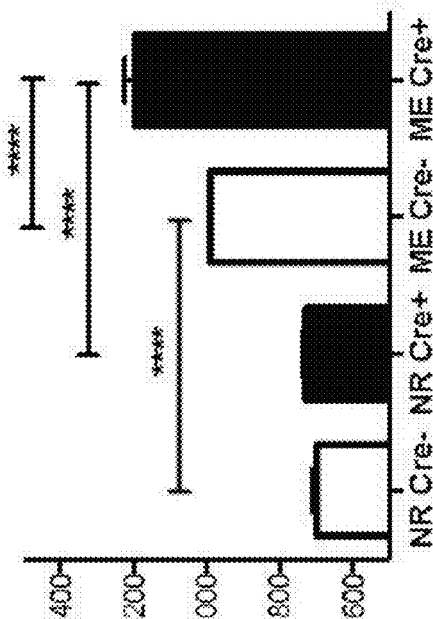
Fig. 16A
Fig. 16B
Fig. 16C
Fig. 16D

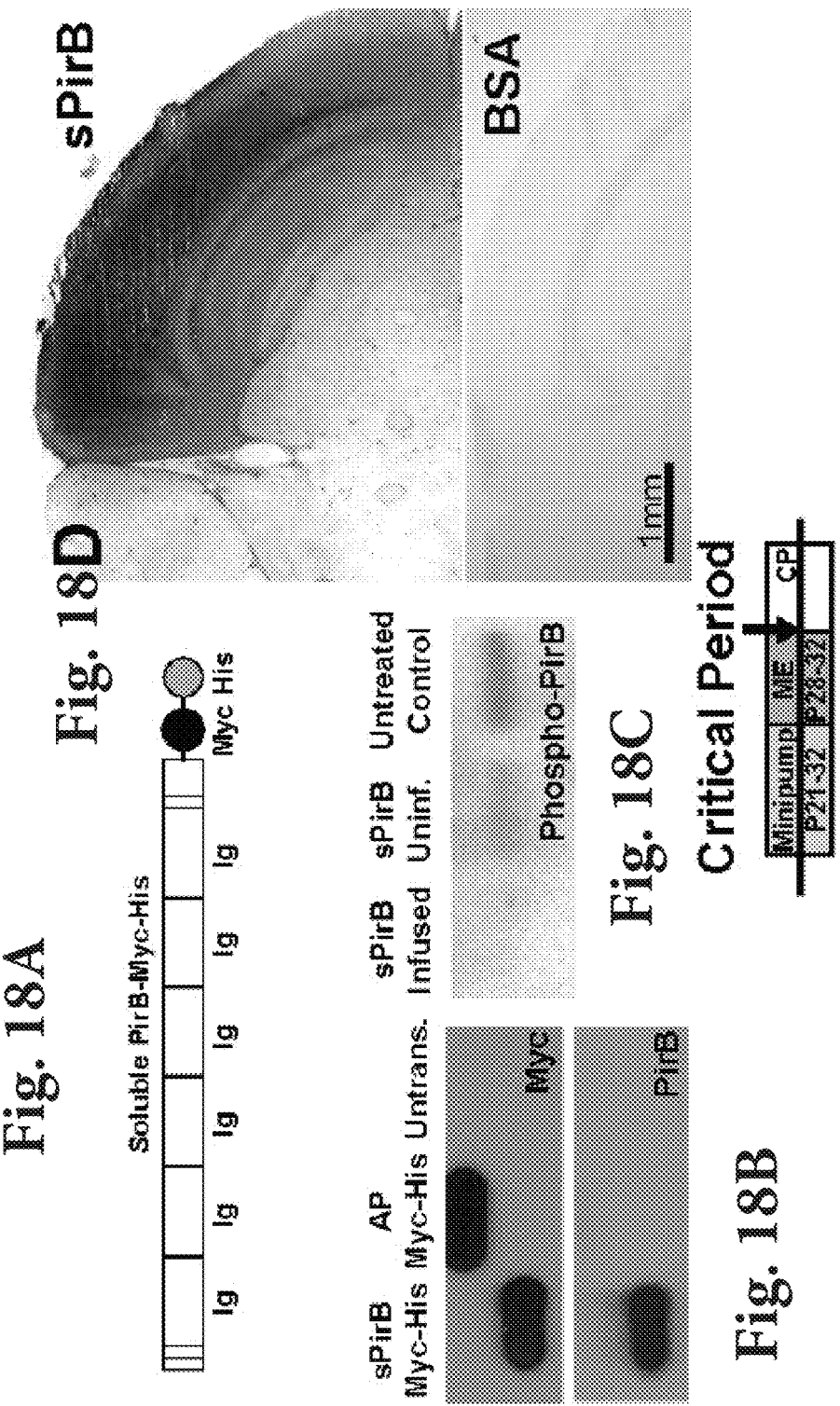

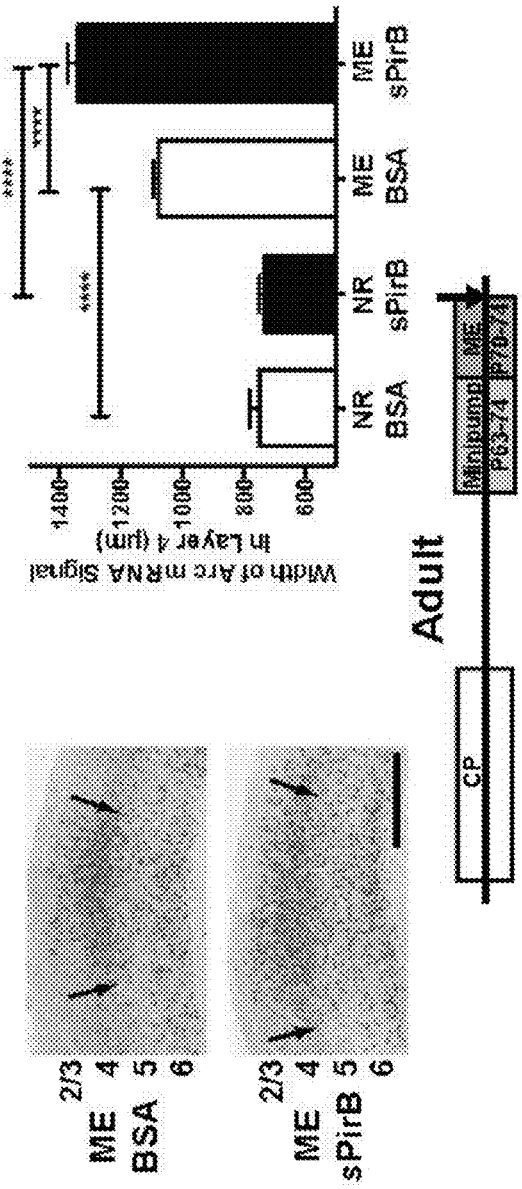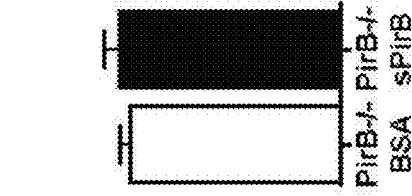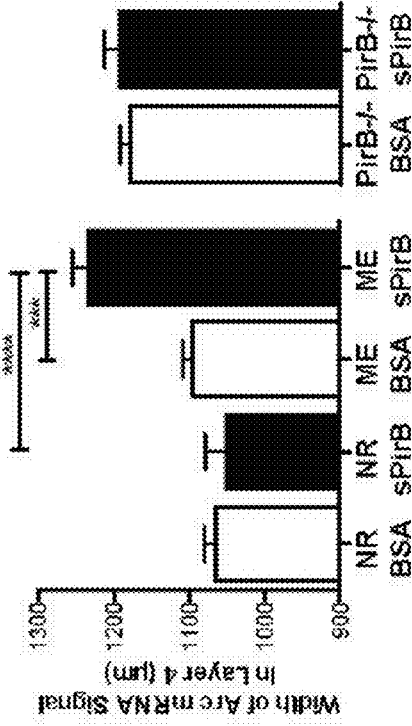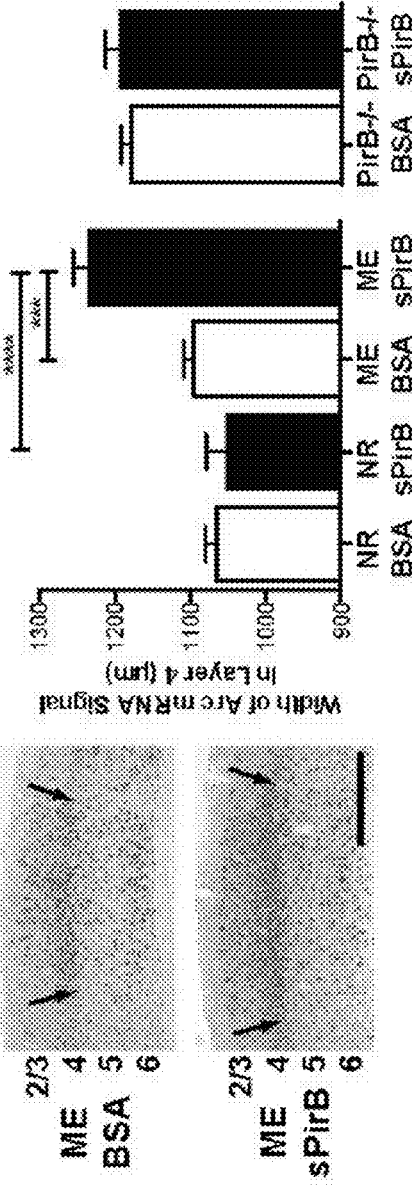

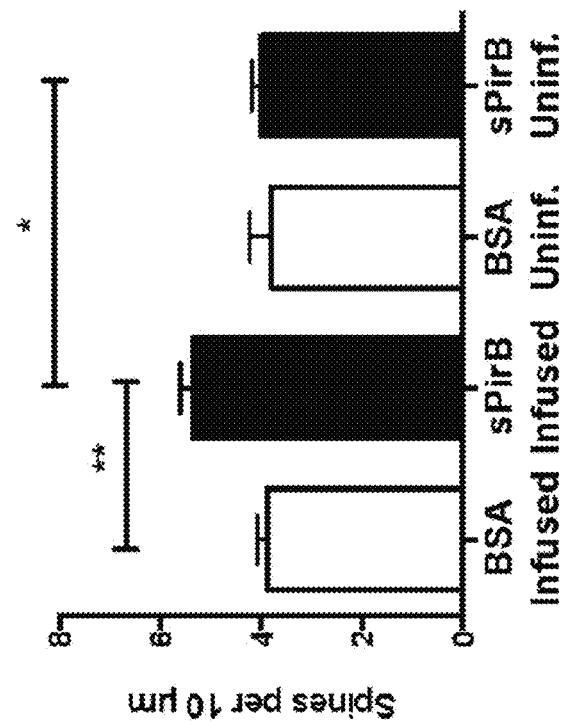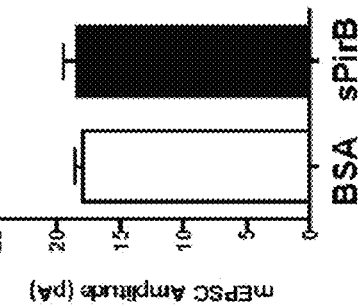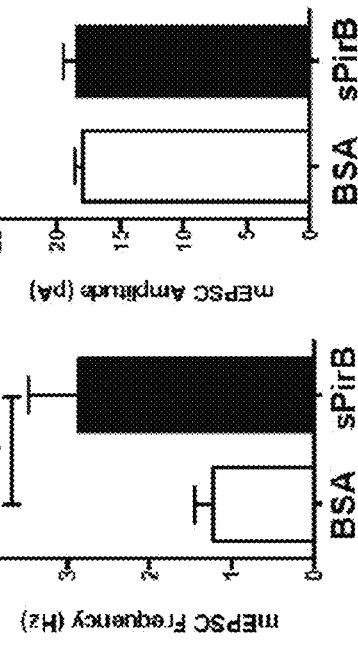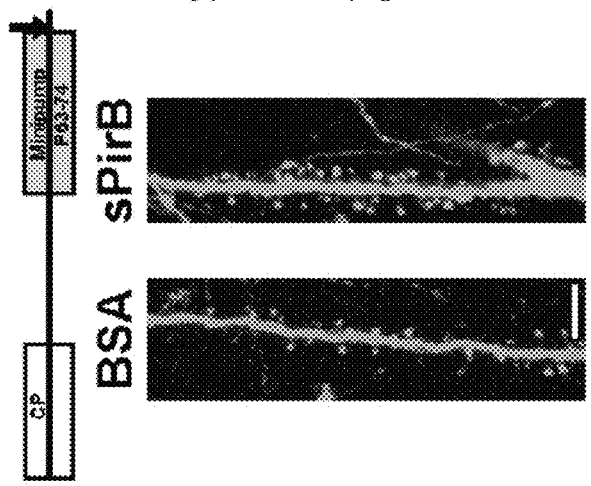

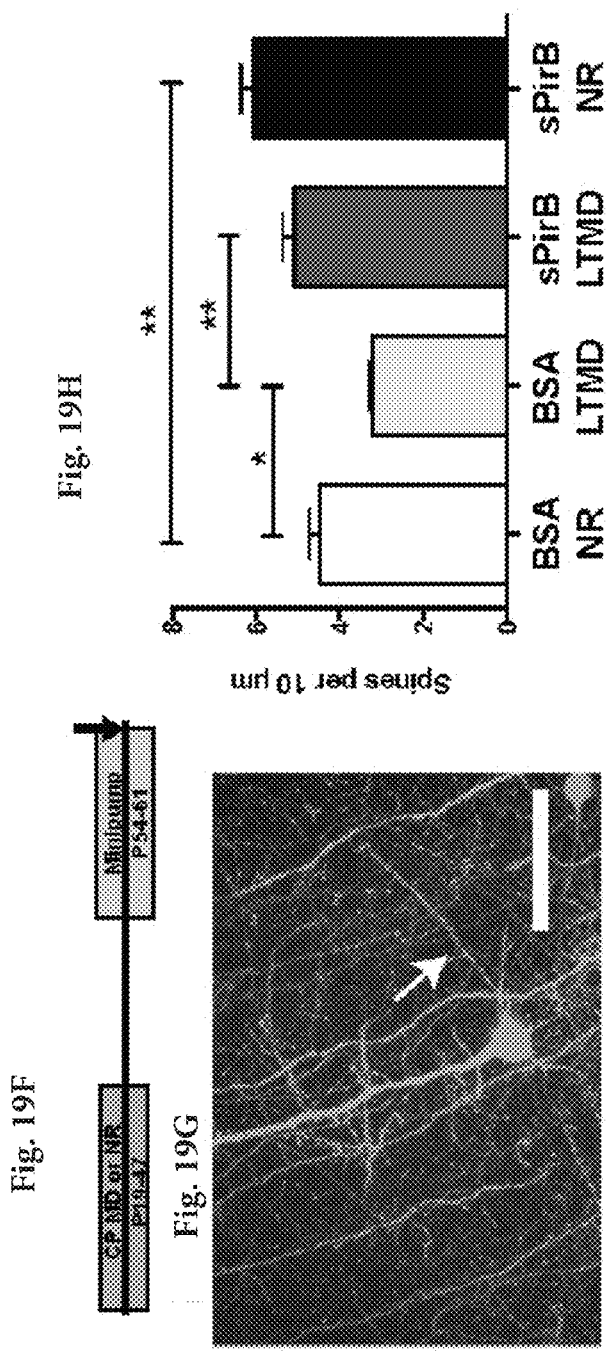

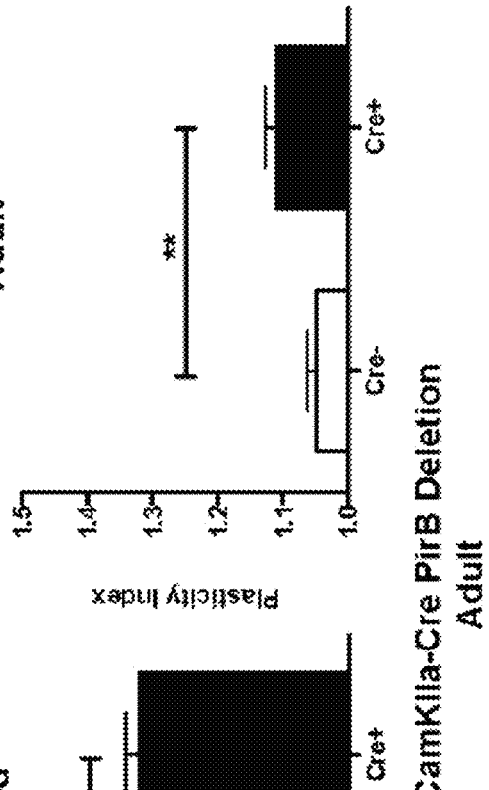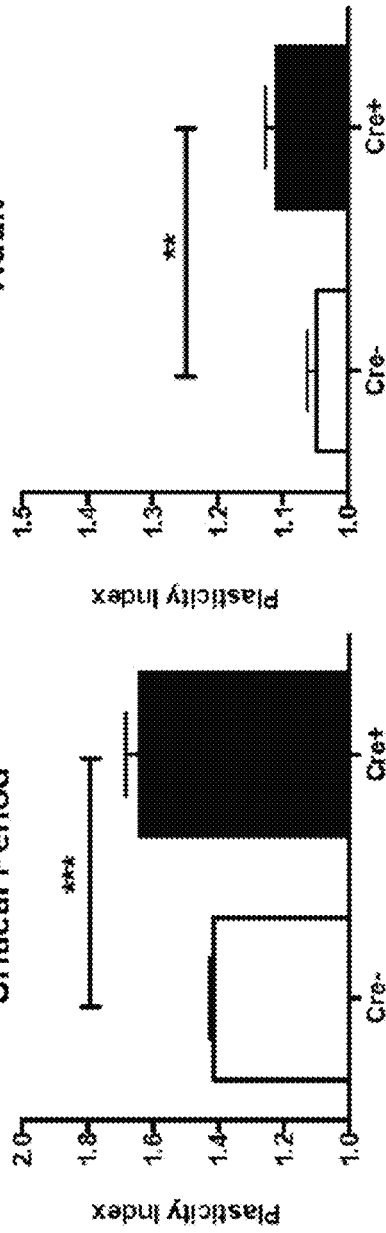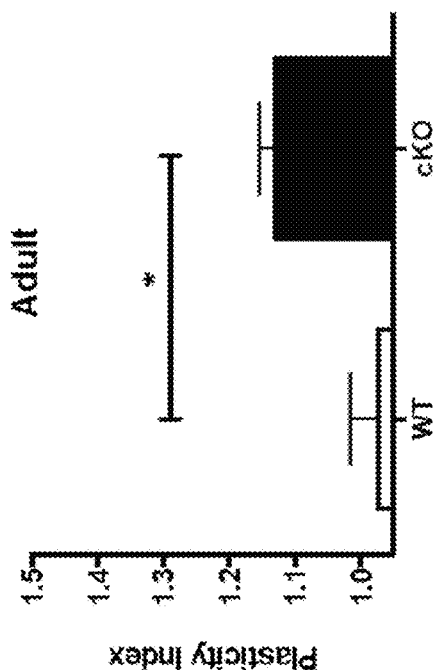
Fig. 20A Inducible PirB Deletion Critical Period
Fig. 20B Inducible PirB Deletion Adult
Fig. 20C CamKIIa-Cre PirB Deletion Adult

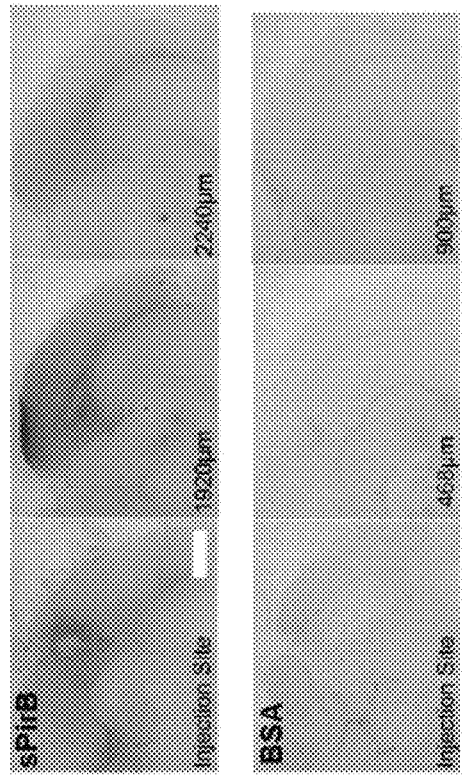
Fig. 21B
Fig. 21C
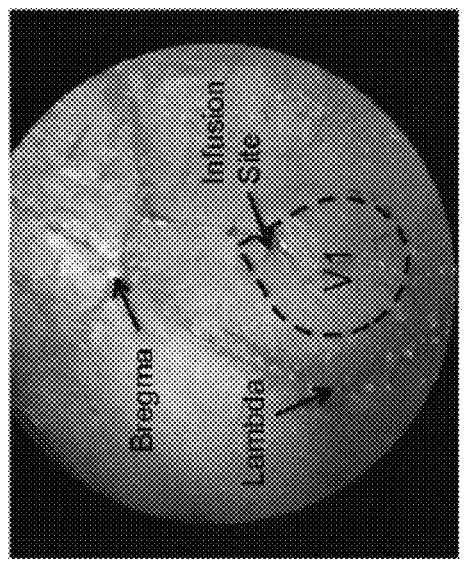
Fig. 21A
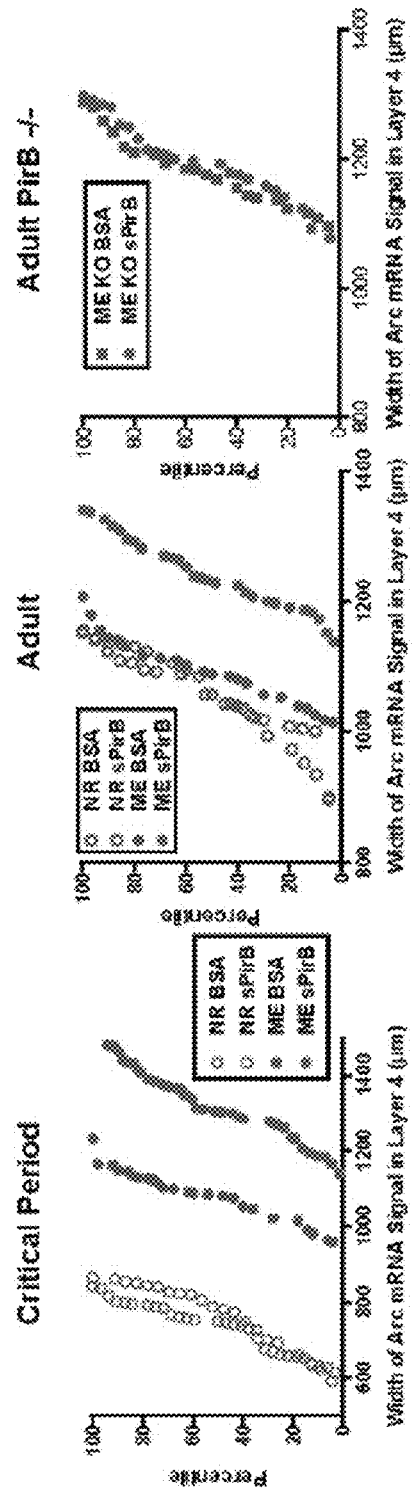
Fig. 21D
Fig. 21E
Fig. 21F

SEQUENCE LISTING

```
<160> NUMBER OF SEQ ID NOS: 28

<210> SEQ ID NO 1
<211> LENGTH: 841
<212> TYPE: PRT
<213> ORGANISM: Mus musculus

<400> SEQUENCE: 1

Met Ser Cys Thr Phe Thr Ala Leu Leu Arg Leu Gly Leu Thr Leu Ser
1               5                   10                  15

Leu Trp Ile Pro Val Leu Thr Gly Ser Leu Pro Lys Pro Ile Leu Arg
                20                  25                  30

Val Gln Pro Asp Ser Val Val Ser Arg Arg Thr Lys Val Thr Phe Leu
            35                  40                  45

Cys Glu Glu Thr Ile Gly Ala Asn Glu Tyr Arg Leu Tyr Lys Asp Gly
        50                  55                  60

Lys Leu Tyr Lys Thr Val Thr Lys Asn Lys Gln Lys Pro Glu Asn Lys
65                  70                  75                  80

Ala Glu Phe Ser Phe Ser Asn Val Asp Leu Ser Asn Ala Gly Gln Tyr
                85                  90                  95

Arg Cys Ser Tyr Ser Thr Gln Tyr Lys Ser Ser Gly Tyr Ser Asp Leu
            100                 105                 110

Leu Glu Leu Val Val Thr Gly His Tyr Trp Thr Pro Ser Leu Leu Ala
        115                 120                 125

Gln Ala Ser Pro Val Val Thr Ser Gly Gly Tyr Val Thr Leu Gln Cys
    130                 135                 140
```

-continued

Glu Ser Trp His Asn Asp His Lys Phe Ile Leu Thr Val Glu Gly Pro
145                 150                 155                 160

Gln Lys Leu Ser Trp Thr Gln Asp Ser Gln Tyr Asn Tyr Ser Thr Arg
            165                 170                 175

Lys Tyr His Ala Leu Phe Ser Val Gly Pro Val Thr Pro Asn Gln Arg
        180                 185                 190

Trp Ile Cys Arg Cys Tyr Ser Tyr Asp Arg Asn Arg Pro Tyr Val Trp
    195                 200                 205

Ser Pro Pro Ser Glu Ser Val Glu Leu Leu Val Ser Gly Asn Leu Gln
210                 215                 220

Lys Pro Thr Ile Lys Ala Glu Pro Gly Ser Val Ile Thr Ser Lys Arg
225                 230                 235                 240

Ala Met Thr Ile Trp Cys Gln Gly Asn Leu Asp Ala Glu Val Tyr Phe
                245                 250                 255

Leu His Asn Glu Lys Ser Gln Lys Thr Gln Ser Thr Gln Thr Leu Gln
            260                 265                 270

Glu Pro Gly Asn Lys Gly Lys Phe Phe Ile Pro Ser Val Thr Leu Gln
        275                 280                 285

His Ala Gly Gln Tyr Arg Cys Tyr Cys Tyr Gly Ser Ala Gly Trp Ser
290                 295                 300

Gln Pro Ser Asp Thr Leu Glu Leu Val Val Thr Gly Ile Tyr Glu Tyr
305                 310                 315                 320

Tyr Glu Pro Arg Leu Ser Val Leu Pro Ser Pro Val Val Thr Ala Gly
                325                 330                 335

Gly Asn Met Thr Leu His Cys Ala Ser Asp Phe Pro Tyr Asp Lys Phe
            340                 345                 350

Ile Leu Thr Lys Glu Asp Lys Lys Phe Gly Asn Ser Leu Asp Thr Glu
        355                 360                 365

His Ile Ser Ser Ser Gly Gln Tyr Arg Ala Leu Phe Ile Ile Gly Pro
370                 375                 380

Thr Thr Pro Thr His Thr Gly Ala Phe Arg Cys Tyr Gly Tyr Tyr Lys
385                 390                 395                 400

Asn Ala Pro Gln Leu Trp Ser Val Pro Ser Ala Leu Gln Gln Ile Leu
                405                 410                 415

Ile Ser Gly Leu Ser Lys Lys Pro Ser Leu Leu Thr His Gln Gly His
            420                 425                 430

Ile Leu Asp Pro Gly Met Thr Leu Thr Leu Gln Cys Phe Ser Asp Ile
        435                 440                 445

Asn Tyr Asp Arg Phe Ala Leu His Lys Val Gly Gly Ala Asp Ile Met
450                 455                 460

Gln His Ser Ser Gln Gln Thr Asp Thr Gly Phe Ser Val Ala Asn Phe
465                 470                 475                 480

Thr Leu Gly Tyr Val Ser Ser Ser Thr Gly Gly Gln Tyr Arg Cys Tyr
                485                 490                 495

Gly Ala His Asn Leu Ser Ser Glu Trp Ser Ala Ser Ser Glu Pro Leu
            500                 505                 510

Asp Ile Leu Ile Thr Gly Gln Leu Pro Leu Thr Pro Ser Leu Ser Val
        515                 520                 525

Gln Pro Asn His Thr Val His Ser Gly Glu Thr Val Ser Leu Leu Cys
530                 535                 540

Trp Ser Met Asp Ser Val Asp Thr Phe Ile Leu Ser Lys Glu Gly Ser
545                 550                 555                 560

```
Ala Gln Gln Pro Leu Arg Leu Lys Ser Lys Ser His Asp Gln Gln Ser
                565                 570                 575

Gln Ala Glu Phe Ser Met Ser Ala Val Thr Ser His Leu Ser Gly Thr
            580                 585                 590

Tyr Arg Cys Tyr Gly Ala Gln Asp Ser Ser Phe Tyr Leu Leu Ser Ser
        595                 600                 605

Ala Ser Ala Pro Val Glu Leu Thr Val Ser Gly Pro Ile Glu Thr Ser
    610                 615                 620

Thr Pro Pro Thr Met Ser Met Pro Leu Gly Leu His Met Tyr
625                 630                 635                 640

Leu Lys Ala Leu Ile Gly Val Ser Val Ala Phe Ile Leu Phe Leu Phe
                645                 650                 655

Ile Phe Ile Phe Ile Leu Leu Arg Arg Arg His Arg Gly Lys Phe Arg
            660                 665                 670

Lys Asp Val Gln Lys Glu Lys Asp Leu Gln Leu Ser Ser Gly Ala Glu
        675                 680                 685

Glu Pro Ile Thr Arg Lys Gly Glu Leu Gln Lys Arg Pro Asn Pro Ala
    690                 695                 700

Ala Ala Thr Gln Glu Glu Ser Leu Tyr Ala Ser Val Glu Asp Met Gln
705                 710                 715                 720

Thr Glu Asp Gly Val Glu Leu Asn Ser Trp Thr Pro Pro Glu Glu Asp
                725                 730                 735

Pro Gln Gly Glu Thr Tyr Ala Gln Val Lys Pro Ser Arg Leu Arg Lys
            740                 745                 750

Ala Gly His Val Ser Pro Ser Val Met Ser Arg Glu Gln Leu Asn Thr
        755                 760                 765

Glu Tyr Glu Gln Ala Glu Glu Gly Gln Gly Ala Asn Asn Gln Ala Ala
    770                 775                 780

Glu Ser Gly Glu Ser Gln Asp Val Thr Tyr Ala Gln Leu Cys Ser Arg
785                 790                 795                 800

Thr Leu Arg Gln Gly Ala Ala Ala Ser Pro Leu Ser Gln Ala Gly Glu
                805                 810                 815

Ala Pro Glu Glu Pro Ser Val Tyr Ala Thr Leu Ala Ala Ala Arg Pro
            820                 825                 830

Glu Ala Val Pro Lys Asp Met Glu Gln
        835                 840

<210> SEQ ID NO 2
<211> LENGTH: 2728
<212> TYPE: DNA
<213> ORGANISM: Mus musculus

<400> SEQUENCE: 2
gaaaggctct gtagctctgc ccttgagcac agttgcagcc actgagggga gatgccatgt      60
cctgcacctt cacagccctg ctccgtcttg gactgactct gagcctctgg atcccagtgc     120
tgacagggtc cctccctaag cctatcctca gagtacagcc agactctgtg gtctccagga     180
ggactaaggt gaccttcttg tgtgaagaga caattggagc caatgagtac cgcctctata     240
aagatggaaa gctatataaa accgtaacaa gaacaaaaca gaagccagaa aacaaggctg     300
aattctcatt ctcaaatgta gacctgagta atgcaggtca atatcgatgt tcctacagca     360
cccagtataa atcatcaggc tacagtgacc tcctggagct ggtggtgaca ggacactact     420
ggacacccag cctttttagcc caagccagcc ctgtggtaac ttcaggaggg tatgtcaccc     480
tccagtgtga gtcctggcac aacgatcaca agttcattct gactgtagaa ggaccacaga     540
```

| | |
|---|---|
| agctctcgtg gacacaagac tcacagtata attactctac aaggaagtac cacgccctgt | 600 |
| tctctgtggg ccctgtgacc cccaaccaga gatggatatg cagatgttac agttatgaca | 660 |
| ggaacagacc atatgtgtgg tcacctccaa gtgaatccgt ggagctcctg gtctcaggta | 720 |
| atctccaaaa accaaccatc aaggctgaac caggatctgt gatcacctcc aaaagagcaa | 780 |
| tgaccatctg gtgtcagggg aacctggatg cagaagtata ttttctgcat aatgagaaaa | 840 |
| gccaaaaaac acagagcaca cagaccctac aggagcctgg gaacaagggc aagttcttca | 900 |
| tcccttctgt gacactacaa catgcagggc aatatcgctg ttattgttac ggctcagctg | 960 |
| gttggtcaca gcccagtgac accctggagc tggtggtgac aggaatctat gaatactatg | 1020 |
| aacccaggct gtcagtactg cccagccctg tggtgacagc tggagggaac atgacactcc | 1080 |
| actgtgcctc agactttccc tacgataaat tcattctcac caaggaagat aagaaattcg | 1140 |
| gcaactcact ggacacagag catatatctt ctagtggaca gtaccgagcc tgtttattta | 1200 |
| taggacccac aaccccaacc catacagggg cattcagatg ttacggttac tacaagaatg | 1260 |
| ccccacagct gtggtcagta cctagtgctc tccaacaaat actcatctca gggctgtcca | 1320 |
| agaagccctc tctgctgact caccaaggcc atatcctgga ccctggaatg accctcaccc | 1380 |
| tgcagtgttt ctctgacatc aactatgaca gatttgctct gcacaaggtg gggggagctg | 1440 |
| acatcatgca gcactctagc cagcagactg acactggctt ctctgtggcc aacttcacac | 1500 |
| tgggctatgt gagtagctcc actggaggcc aatacagatg ctatggtgca cacaaccctct | 1560 |
| cctctgagtg gtcagcctcc agtgagcccc tggacatcct gatcacagga cagctccctc | 1620 |
| tcactccttc cctctcagtg cagcctaacc acacagtgca ctcaggagag accgtgagcc | 1680 |
| tgctgtgttg gtcaatggac tctgtggata ctttcattct gtccaaggag ggatcagccc | 1740 |
| agcaaccccct gcgactaaaa tcaaagtccc atgatcagca gtcccaggca gaattctcca | 1800 |
| tgagtgctgt gacctcccat ctctcaggca cctacaggtg ctatggagct caagactcat | 1860 |
| ctttctacct cttgtcatct gccagtgccc ctgtggagct cacagtctca ggacccatcg | 1920 |
| aaacctctac cccgccaccc acaatgtcca tgccactagg tggactgcat atgtacctga | 1980 |
| aggctctcat tggagtgtct gtggccttca tcctgttcct cttcatcttc atcttcattc | 2040 |
| ttcttcgacg aagacatcgg ggaaaattca ggaaagatgt ccagaaagag aaagacttgc | 2100 |
| aactttcttc aggagctgaa gagcccataa ccaggaaagg agaactccag aagaggccca | 2160 |
| acccagctgc tgccacccag gaagaaagcc tatatgcttc agtggaggac atgcaaactg | 2220 |
| aggatggagt ggagctgaac agctggacac cacctgagga agatcccag ggagagactt | 2280 |
| atgcccaggt gaaaccctcc aggctcagga aggcaggaca tgtctcacct tctgtcatgt | 2340 |
| caagggaaca actgaacaca gaatatgaac aagcagaaga gggccaagga gcaaacaatc | 2400 |
| aggctgccga atctggggag tcccaggatg tgacctatgc ccagctgtgc agcaggacac | 2460 |
| tcagacaggg ggcagctgca tctcctctct cccaggcagg gaagccccca gaggagccca | 2520 |
| gtgtatatgc tactctggcg gctgctcgtc cagaggctgt tcccaaggac atggagcaat | 2580 |
| gaccccctgc ctgccaggat gcctagcaga gacctccaag ggactctggg aacttttgga | 2640 |
| aacgtgactg cactttaagt aacatcagag tttggaaata aagctagaga tttctcaata | 2700 |
| atcaagtgaa atgagaaatg aaatggaa | 2728 |

<210> SEQ ID NO 3
<211> LENGTH: 598
<212> TYPE: PRT
<213> ORGANISM: Homo sapiens

<400> SEQUENCE: 3

```
Met Thr Pro Ile Val Thr Val Leu Ile Cys Leu Gly Leu Ser Leu Gly
1               5                   10                  15

Pro Arg Thr His Val Gln Thr Gly Thr Ile Pro Lys Pro Thr Leu Trp
                20                  25                  30

Ala Glu Pro Asp Ser Val Ile Thr Gln Gly Ser Pro Val Thr Leu Ser
            35                  40                  45

Cys Gln Gly Ser Leu Glu Ala Gln Glu Tyr Arg Leu Tyr Arg Glu Lys
        50                  55                  60

Lys Ser Ala Ser Trp Ile Thr Arg Ile Arg Pro Glu Leu Val Lys Asn
65                  70                  75                  80

Gly Gln Phe His Ile Pro Ser Ile Thr Trp Glu His Thr Gly Arg Tyr
                85                  90                  95

Gly Cys Gln Tyr Tyr Ser Arg Ala Arg Trp Ser Glu Leu Ser Asp Pro
            100                 105                 110

Leu Val Leu Val Met Thr Gly Ala Tyr Pro Lys Pro Thr Leu Ser Ala
        115                 120                 125

Gln Pro Ser Pro Val Val Thr Ser Gly Gly Arg Val Thr Leu Gln Cys
    130                 135                 140

Glu Ser Gln Val Ala Phe Gly Gly Phe Ile Leu Cys Lys Glu Gly Glu
145                 150                 155                 160

Glu Glu His Pro Gln Cys Leu Asn Ser Gln Pro His Ala Arg Gly Ser
                165                 170                 175

Ser Arg Ala Ile Phe Ser Val Gly Pro Val Ser Pro Asn Arg Arg Trp
            180                 185                 190

Ser His Arg Cys Tyr Gly Tyr Asp Leu Asn Ser Pro Tyr Val Trp Ser
        195                 200                 205

Ser Pro Ser Asp Leu Leu Glu Leu Leu Val Pro Gly Val Ser Lys Lys
    210                 215                 220

Pro Ser Leu Ser Val Gln Pro Gly Pro Val Val Ala Pro Gly Glu Ser
225                 230                 235                 240

Leu Thr Leu Gln Cys Val Ser Asp Val Gly Tyr Asp Arg Phe Val Leu
                245                 250                 255

Tyr Lys Glu Gly Glu Arg Asp Leu Arg Gln Leu Pro Gly Arg Gln Pro
            260                 265                 270

Gln Ala Gly Leu Ser Gln Ala Asn Phe Thr Leu Gly Pro Val Ser Arg
        275                 280                 285

Ser Tyr Gly Gly Gln Tyr Arg Cys Tyr Gly Ala His Asn Leu Ser Ser
    290                 295                 300

Glu Cys Ser Ala Pro Ser Asp Pro Leu Asp Ile Leu Ile Thr Gly Gln
305                 310                 315                 320

Ile Arg Gly Thr Pro Phe Ile Ser Val Gln Pro Gly Pro Thr Val Ala
                325                 330                 335

Ser Gly Glu Asn Val Thr Leu Leu Cys Gln Ser Trp Arg Gln Phe His
            340                 345                 350

Thr Phe Leu Leu Thr Lys Ala Gly Ala Ala Asp Ala Pro Leu Arg Leu
        355                 360                 365

Arg Ser Ile His Glu Tyr Pro Lys Tyr Gln Ala Glu Phe Pro Met Ser
    370                 375                 380

Pro Val Thr Ser Ala His Ala Gly Thr Tyr Arg Cys Tyr Gly Ser Leu
385                 390                 395                 400

Asn Ser Asp Pro Tyr Leu Leu Ser His Pro Ser Glu Pro Leu Glu Leu
                405                 410                 415
```

| | | | | | | | | | | | |
|---|---|---|---|---|---|---|---|---|---|---|---|
|Val|Val|Ser|Gly|Pro|Ser|Met|Gly|Ser|Ser|Pro|Pro|Thr|Gly|Pro|
| | | |420| | |425| | | |430| |

| | | | | | | | | | | | |
|---|---|---|---|---|---|---|---|---|---|---|---|
|Ile|Ser|Thr|Pro|Ala|Gly|Pro|Glu|Asp|Gln|Pro|Leu|Thr|Pro|Thr|Gly|
| | |435| | | |440| | | |445|

Ser Asp Pro Gln Ser Gly Leu Gly Arg His Leu Gly Val Val Ile Gly
         450                 455                 460

Ile Leu Val Ala Val Val Leu Leu Leu Leu Leu Leu Leu Leu Leu Phe
465                 470                 475                 480

Leu Ile Leu Arg His Arg Arg Gln Gly Lys His Trp Thr Ser Thr Gln
                 485                 490                 495

Arg Lys Ala Asp Phe Gln His Pro Ala Gly Ala Val Gly Pro Glu Pro
                 500                 505                 510

Thr Asp Arg Gly Leu Gln Trp Arg Ser Ser Pro Ala Ala Asp Ala Gln
                 515                 520                 525

Glu Glu Asn Leu Tyr Ala Ala Val Lys Asp Thr Gln Pro Glu Asp Gly
                 530                 535                 540

Val Glu Met Asp Thr Arg Ala Ala Ala Ser Glu Ala Pro Gln Asp Val
545                 550                 555                 560

Thr Tyr Ala Gln Leu His Ser Leu Thr Leu Arg Arg Lys Ala Thr Glu
                 565                 570                 575

Pro Pro Pro Ser Gln Glu Arg Glu Pro Pro Ala Glu Pro Ser Ile Tyr
                 580                 585                 590

Ala Thr Leu Ala Ile His
                 595

<210> SEQ ID NO 4
<211> LENGTH: 2940
<212> TYPE: DNA
<213> ORGANISM: Homo sapiens

<400> SEQUENCE: 4

```
atttggttga aagaaaaccc acaatccagt gtcaagaaag aagtcaactt ttcttcccct      60
acttccctgc atttctcctc tgtgctcact gccacacgca gctcaacctg gacggcacag     120
ccagaggcga gatgcttctc tgctgatctg agtctgcctg cagcatggac ctgggtcttc     180
cctgaagcat ctccagggct ggagggacga ctgccatgca ccgagggctc atccatccgc     240
agagcagggc agtgggagga gacgccatga ccccatcgt cacagtcctg atctgtctcg      300
ggctgagtct gggccccagg acccacgtgc agacagggac cattcccaag ccaccctgt      360
gggctgagcc agactctgtg atcacccagg ggagtcccgt cacctcagt tgtcagggga      420
gccttgaagc ccaggagtac cgtctatata gggagaaaaa atcagcatct tggattacac     480
ggatacgacc agagcttgtg aagaacggcc agttccacat cccatccatc acctgggaac     540
acacagggcg atatggctgt cagtattaca gccgcgctcg gtggtctgag ctcagtgacc     600
ccctggtgct ggtgatgaca ggagcctacc caaaacccac cctctcagcc cagcccagcc     660
ctgtggtgac ctcaggagga agggtgaccc tccagtgtga gtcacaggtg gcatttggcg     720
gcttcattct gtgtaaggaa ggagaagaag aacacccaca atgcctgaac tcccagcccc     780
atgcccgtgg gtcgtcccgc gccatcttct ccgtgggccc cgtgagcccg aatcgcaggt     840
ggtcgcacag gtgctatggt tatgacttga actctcccta tgtgtggtct tcacccagtg     900
atctcctgga gctcctggtc ccaggtgttt ctaagaagcc atcactctca gtgcagccgg     960
gtcctgtcgt ggcccctggg gaaagcctga cctccagtg tgtctctgat gtcggctatg    1020
acagatttgt tctgtacaag gagggggaac gtgaccttcg ccagctccct ggccggcagc    1080
```

-continued

```
cccaggctgg gctctcccag gccaacttca ccctgggccc tgtgagccgc tcctacgggg    1140
gccagtacag atgctacggt gcacacaacc tctcctctga gtgctcggcc ccagcgacc     1200
ccctggacat cctgatcaca ggacagatcc gtggcacacc cttcatctca gtgcagccag    1260
gccccacagt ggcctcagga gagaacgtga ccctgctgtg tcagtcatgg cggcagttcc    1320
acactttcct tctgaccaag gcgggagcag ctgatgcccc actccgtcta agatcaatac    1380
acgaatatcc taagtaccag gctgaattcc ccatgagtcc tgtgacctca gcccacgcgg    1440
ggacctacag gtgctacggc tcactcaact ccgaccccta cctgctgtct caccccagtg    1500
agccctgga gctcgtggtc tcaggaccct ccatgggttc cagcccccca ccaccggtc      1560
ccatctccac acctgcaggc cctgaggacc agcccctcac ccccactggg tcggatcccc    1620
aaagtggtct gggaaggcac ctgggggttg tgatcggcat cttggtggcc gtcgtcctac    1680
tgctcctcct cctcctcctc ctcttcctca tcctccgaca tcgacgtcag ggcaaacact    1740
ggacatcgac ccagagaaag gctgatttcc aacatcctgc aggggctgtg gggccagagc    1800
ccacagacag aggcctgcag tggaggtcca gcccagctgc cgacgcccag gaagaaaacc    1860
tctatgctgc cgtgaaggac acacagcctg aagatggggt ggagatggac actcgggctg    1920
ctgcatctga agcccccag gatgtgacct acgcccagct gcacagcttg accctcagac    1980
ggaaggcaac tgagcctcct ccatcccagg aaagggaacc tccagctgag cccagcatct    2040
acgccaccct ggccatccac tagcccggag ggtacgcaga ctccacactc agtagaagga    2100
gactcaggac tgctgaaggc acgggagctg cccccagtgg acaccaatga accccagtca    2160
gcctggaccc ctaacaaaga ccatgaggag atgctgggaa cttgggact cacttgattc     2220
tgcagtcgaa ataactaata tccctacatt ttttaattaa agcaacagac ttctcaataa    2280
tcaatgagtt aaccgagaaa actaaaatca gaagtaagaa tgtgctttaa actgaatcac    2340
aatataaata ttacacatca cacaatgaaa ttgaaaaagt acaaaccaca aatgaaaaaa    2400
gtagaaacga aaaaaaaaaa ctaggaaatg aatgacgttg gctttcgtat aaggaattta    2460
gaaaagaat aaccaattat tccaaatgaa ggtgtaagaa agggaataag aagaagaaga    2520
gttgctcatg aggaaaaacc aaaacttgaa aattcaacaa agccaatgaa gctcattctt    2580
gaaaatatta attacagtca taaatcctaa ctacattgag caagagaaag aaagagcagg    2640
cacgcatttc catatgggag tgagccagca gacagcccag cagatcctac acacattttc    2700
acaaactaac cccagaacag gctgcaaacc tataccaata tactagaaaa tgcagattaa    2760
atggatgaaa tattcaaaac tggagtttac ataatgaacg taagagtaat cagagaatct    2820
gactcatttt aaatgtgtgt gtatgtgtgt gtatatatat gtgtgtgtgt gtgtgtgtgt    2880
gtgtgtgtga aaaacattga ctgtaataaa aatgttccca tcgtaaaaaa aaaaaaaaaa    2940
```

<210> SEQ ID NO 5
<211> LENGTH: 642
<212> TYPE: PRT
<213> ORGANISM: Mus musculus

<400> SEQUENCE: 5

```
Met Ser Cys Thr Phe Thr Ala Leu Leu Arg Leu Gly Leu Thr Leu Ser
1               5                   10                  15

Leu Trp Ile Pro Val Leu Thr Gly Ser Leu Pro Lys Pro Ile Leu Arg
            20                  25                  30

Val Gln Pro Asp Ser Val Val Ser Arg Arg Thr Lys Val Thr Phe Leu
        35                  40                  45
```

-continued

Cys Glu Glu Thr Ile Gly Ala Asn Glu Tyr Arg Leu Tyr Lys Asp Gly
    50                  55                  60

Lys Leu Tyr Lys Thr Val Thr Lys Asn Lys Gln Lys Pro Glu Asn Lys
 65                  70                  75                  80

Ala Glu Phe Ser Phe Ser Asn Val Asp Leu Ser Asn Ala Gly Gln Tyr
                 85                  90                  95

Arg Cys Ser Tyr Ser Thr Gln Tyr Lys Ser Ser Gly Tyr Ser Asp Leu
            100                 105                 110

Leu Glu Leu Val Val Thr Gly His Tyr Trp Thr Pro Ser Leu Leu Ala
        115                 120                 125

Gln Ala Ser Pro Val Val Thr Ser Gly Gly Tyr Val Thr Leu Gln Cys
130                 135                 140

Glu Ser Trp His Asn Asp His Lys Phe Ile Leu Thr Val Glu Gly Pro
145                 150                 155                 160

Gln Lys Leu Ser Trp Thr Gln Asp Ser Gln Tyr Asn Tyr Ser Thr Arg
                165                 170                 175

Lys Tyr His Ala Leu Phe Ser Val Gly Pro Val Thr Pro Asn Gln Arg
            180                 185                 190

Trp Ile Cys Arg Cys Tyr Ser Tyr Asp Arg Asn Arg Pro Tyr Val Trp
        195                 200                 205

Ser Pro Pro Ser Glu Ser Val Glu Leu Leu Val Ser Gly Asn Leu Gln
210                 215                 220

Lys Pro Thr Ile Lys Ala Glu Pro Gly Ser Val Ile Thr Ser Lys Arg
225                 230                 235                 240

Ala Met Thr Ile Trp Cys Gln Gly Asn Leu Asp Ala Glu Val Tyr Phe
                245                 250                 255

Leu His Asn Glu Lys Ser Gln Lys Thr Gln Ser Thr Gln Thr Leu Gln
            260                 265                 270

Glu Pro Gly Asn Lys Gly Lys Phe Phe Ile Pro Ser Val Thr Leu Gln
        275                 280                 285

His Ala Gly Gln Tyr Arg Cys Tyr Cys Tyr Gly Ser Ala Gly Trp Ser
290                 295                 300

Gln Pro Ser Asp Thr Leu Glu Leu Val Val Thr Gly Ile Tyr Glu Tyr
305                 310                 315                 320

Tyr Glu Pro Arg Leu Ser Val Leu Pro Ser Pro Val Val Thr Ala Gly
                325                 330                 335

Gly Asn Met Thr Leu His Cys Ala Ser Asp Phe Pro Tyr Asp Lys Phe
            340                 345                 350

Ile Leu Thr Lys Glu Asp Lys Lys Phe Gly Asn Ser Leu Asp Thr Glu
        355                 360                 365

His Ile Ser Ser Ser Gly Gln Tyr Arg Ala Leu Phe Ile Ile Gly Pro
370                 375                 380

Thr Thr Pro Thr His Thr Gly Ala Phe Arg Cys Tyr Gly Tyr Tyr Lys
385                 390                 395                 400

Asn Ala Pro Gln Leu Trp Ser Val Pro Ser Ala Leu Gln Gln Ile Leu
                405                 410                 415

Ile Ser Gly Leu Ser Lys Lys Pro Ser Leu Leu Thr His Gln Gly His
            420                 425                 430

Ile Leu Asp Pro Gly Met Thr Leu Thr Leu Gln Cys Phe Ser Asp Ile
        435                 440                 445

Asn Tyr Asp Arg Phe Ala Leu His Lys Val Gly Gly Ala Asp Ile Met
450                 455                 460

```
Gln His Ser Ser Gln Gln Thr Asp Thr Gly Phe Ser Val Ala Asn Phe
465                 470                 475                 480

Thr Leu Gly Tyr Val Ser Ser Thr Gly Gly Gln Tyr Arg Cys Tyr
            485                 490                 495

Gly Ala His Asn Leu Ser Ser Glu Trp Ser Ala Ser Ser Glu Pro Leu
            500                 505                 510

Asp Ile Leu Ile Thr Gly Gln Leu Pro Leu Thr Pro Ser Leu Ser Val
            515                 520                 525

Gln Pro Asn His Thr Val His Ser Gly Glu Thr Val Ser Leu Leu Cys
            530                 535                 540

Trp Ser Met Asp Ser Val Asp Thr Phe Ile Leu Ser Lys Glu Gly Ser
545                 550                 555                 560

Ala Gln Gln Pro Leu Arg Leu Lys Ser Lys Ser His Asp Gln Gln Ser
            565                 570                 575

Gln Ala Glu Phe Ser Met Ser Ala Val Thr Ser His Leu Ser Gly Thr
            580                 585                 590

Tyr Arg Cys Tyr Gly Ala Gln Asp Ser Ser Phe Tyr Leu Leu Ser Ser
            595                 600                 605

Ala Ser Ala Pro Val Glu Leu Thr Val Ser Gly Pro Ile Glu Thr Ser
            610                 615                 620

Thr Pro Pro Pro Thr Met Ser Met Pro Leu Gly Gly Leu His Met Tyr
625                 630                 635                 640

Leu Lys

<210> SEQ ID NO 6
<211> LENGTH: 458
<212> TYPE: PRT
<213> ORGANISM: Homo sapiens

<400> SEQUENCE: 6

Met Thr Pro Ile Val Thr Val Leu Ile Cys Leu Gly Leu Ser Leu Gly
1               5                   10                  15

Pro Arg Thr His Val Gln Thr Gly Thr Ile Pro Lys Pro Thr Leu Trp
            20                  25                  30

Ala Glu Pro Asp Ser Val Ile Thr Gln Gly Ser Pro Val Thr Leu Ser
            35                  40                  45

Cys Gln Gly Ser Leu Glu Ala Gln Glu Tyr Arg Leu Tyr Arg Glu Lys
        50                  55                  60

Lys Ser Ala Ser Trp Ile Thr Arg Ile Arg Pro Glu Leu Val Lys Asn
65                  70                  75                  80

Gly Gln Phe His Ile Pro Ser Ile Thr Trp Glu His Thr Gly Arg Tyr
            85                  90                  95

Gly Cys Gln Tyr Tyr Ser Arg Ala Arg Trp Ser Glu Leu Ser Asp Pro
            100                 105                 110

Leu Val Leu Val Met Thr Gly Ala Tyr Pro Lys Pro Thr Leu Ser Ala
            115                 120                 125

Gln Pro Ser Pro Val Val Thr Ser Gly Gly Arg Val Thr Leu Gln Cys
            130                 135                 140

Glu Ser Gln Val Ala Phe Gly Gly Phe Ile Leu Cys Lys Glu Gly Glu
145                 150                 155                 160

Glu Glu His Pro Gln Cys Leu Asn Ser Gln Pro His Ala Arg Gly Ser
            165                 170                 175
```

Ser Arg Ala Ile Phe Ser Val Gly Pro Val Ser Pro Asn Arg Arg Trp
            180                 185                 190

Ser His Arg Cys Tyr Gly Tyr Asp Leu Asn Ser Pro Tyr Val Trp Ser
        195                 200                 205

Ser Pro Ser Asp Leu Leu Glu Leu Leu Val Pro Gly Val Ser Lys Lys
    210                 215                 220

Pro Ser Leu Ser Val Gln Pro Gly Pro Val Val Ala Pro Gly Glu Ser
225                 230                 235                 240

Leu Thr Leu Gln Cys Val Ser Asp Val Gly Tyr Asp Arg Phe Val Leu
                245                 250                 255

Tyr Lys Glu Gly Glu Arg Asp Leu Arg Gln Leu Pro Gly Arg Gln Pro
            260                 265                 270

Gln Ala Gly Leu Ser Gln Ala Asn Phe Thr Leu Gly Pro Val Ser Arg
        275                 280                 285

Ser Tyr Gly Gly Gln Tyr Arg Cys Tyr Gly Ala His Asn Leu Ser Ser
    290                 295                 300

Glu Cys Ser Ala Pro Ser Asp Pro Leu Asp Ile Leu Ile Thr Gly Gln
305                 310                 315                 320

Ile Arg Gly Thr Pro Phe Ile Ser Val Gln Pro Gly Pro Thr Val Ala
                325                 330                 335

Ser Gly Glu Asn Val Thr Leu Leu Cys Gln Ser Trp Arg Gln Phe His
            340                 345                 350

Thr Phe Leu Leu Thr Lys Ala Gly Ala Ala Asp Ala Pro Leu Arg Leu
        355                 360                 365

Arg Ser Ile His Glu Tyr Pro Lys Tyr Gln Ala Glu Phe Pro Met Ser
    370                 375                 380

Pro Val Thr Ser Ala His Ala Gly Thr Tyr Arg Cys Tyr Gly Ser Leu
385                 390                 395                 400

Asn Ser Asp Pro Tyr Leu Leu Ser His Pro Ser Glu Pro Leu Glu Leu
                405                 410                 415

Val Val Ser Gly Pro Ser Met Gly Ser Ser Pro Pro Thr Gly Pro
            420                 425                 430

Ile Ser Thr Pro Ala Gly Pro Glu Asp Gln Pro Leu Thr Pro Thr Gly
        435                 440                 445

Ser Asp Pro Gln Ser Gly Leu Gly Arg His
    450                 455

<210> SEQ ID NO 7
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 7
ggccatgggg tccctcccta agcctatcct caga                                34

<210> SEQ ID NO 8
<211> LENGTH: 38
<212> TYPE: DNA
<213> ORGANISM: Artificial sequence
<220> FEATURE:
<223> OTHER INFORMATION: synthetic oligonucleotide

<400> SEQUENCE: 8
ccagatctag ccttcaggta catatgcagt ccacctag                            38

```
<210> SEQ ID NO 9
<211> LENGTH: 36
<212> TYPE: DNA
<213> ORGANISM: Artificial sequence
<220> FEATURE:
<223> OTHER INFORMATION: synthetic oligonucleotide

<400> SEQUENCE: 9
ggccatgggt aatctccaaa aaccaaccat caaggc                              36

<210> SEQ ID NO 10
<211> LENGTH: 38
<212> TYPE: DNA
<213> ORGANISM: Artificial sequence
<220> FEATURE:
<223> OTHER INFORMATION: synthetic oligonucleotide

<400> SEQUENCE: 10
ccagatctag ccttcaggta catatgcagt ccacctag                            38

<210> SEQ ID NO 11
<211> LENGTH: 31
<212> TYPE: DNA
<213> ORGANISM: Artificial sequence
<220> FEATURE:
<223> OTHER INFORMATION: synthetic oligonucleotide

<400> SEQUENCE: 11
ggccatgggg ctgtccaaga agccctctct g                                   31

<210> SEQ ID NO 12
<211> LENGTH: 38
<212> TYPE: DNA
<213> ORGANISM: Artificial sequence
<220> FEATURE:
<223> OTHER INFORMATION: synthetic oligonucleotide

<400> SEQUENCE: 12
ccagatctag ccttcaggta catatgcagt ccacctag                            38

<210> SEQ ID NO 13
<211> LENGTH: 31
<212> TYPE: DNA
<213> ORGANISM: Artificial sequence
<220> FEATURE:
<223> OTHER INFORMATION: synthetic oligonucleotide

<400> SEQUENCE: 13
ggccatgggg ctgtccaaga agccctctct g                                   31

<210> SEQ ID NO 14
<211> LENGTH: 36
<212> TYPE: DNA
<213> ORGANISM: Artificial sequence
<220> FEATURE:
<223> OTHER INFORMATION: synthetic oligonucleotide

<400> SEQUENCE: 14 ccagatctt ggagattacc tgagaccagg agctcc                               36

<210> SEQ ID NO 15
<211> LENGTH: 31
<212> TYPE: DNA
<213> ORGANISM: Artificial sequence
<220> FEATURE:
<223> OTHER INFORMATION: synthetic oligonucleotide
```

<400> SEQUENCE: 15
ggccatgggg ctgtccaaga agccctctct g                                      31

<210> SEQ ID NO 16
<211> LENGTH: 38
<212> TYPE: DNA
<213> ORGANISM: Artificial sequence
<220> FEATURE:
<223> OTHER INFORMATION: synthetic oligonucleotide

<400> SEQUENCE: 16
ccagatctct tggacagccc tgagatgagt atttgttg                               38

<210> SEQ ID NO 17
<211> LENGTH: 36
<212> TYPE: DNA
<213> ORGANISM: Artificial sequence
<220> FEATURE:
<223> OTHER INFORMATION: synthetic oligonucleotide

<400> SEQUENCE: 17
ggccatgggt aatctccaaa aaccaaccat caaggc                                 36

<210> SEQ ID NO 18
<211> LENGTH: 38
<212> TYPE: DNA
<213> ORGANISM: Artificial sequence
<220> FEATURE:
<223> OTHER INFORMATION: synthetic oligonucleotide

<400> SEQUENCE: 18
ccagatctct tggacagccc tgagatgagt atttgttg                               38

<210> SEQ ID NO 19
<211> LENGTH: 32
<212> TYPE: DNA
<213> ORGANISM: Artificial sequence
<220> FEATURE:
<223> OTHER INFORMATION: synthetic oligonucleotide

<400> SEQUENCE: 19
ccgatatcag ggaccatccc caagcccacc ct                                     32

<210> SEQ ID NO 20
<211> LENGTH: 32
<212> TYPE: DNA
<213> ORGANISM: Artificial sequence
<220> FEATURE:
<223> OTHER INFORMATION: synthetic oligonucleotide

<400> SEQUENCE: 20
ccagatctgt gccttcccag accactttgg gg                                     32

<210> SEQ ID NO 21
<211> LENGTH: 40
<212> TYPE: DNA
<213> ORGANISM: Artificial sequence
<220> FEATURE:
<223> OTHER INFORMATION: synthetic oligonucleotide

<400> SEQUENCE: 21
ccgatatcac caggtgtttc taagaagcca tcactctcag                             40

```
<210> SEQ ID NO 22
<211> LENGTH: 32
<212> TYPE: DNA
<213> ORGANISM: Artificial sequence
<220> FEATURE:
<223> OTHER INFORMATION: synthetic oligonucleotide

<400> SEQUENCE: 22
ccagatctgt gccttcccag accactttgg gg                                    32

<210> SEQ ID NO 23
<211> LENGTH: 32
<212> TYPE: DNA
<213> ORGANISM: Artificial sequence
<220> FEATURE:
<223> OTHER INFORMATION: synthetic oligonucleotide

<400> SEQUENCE: 23
ccgatatcag ggaccatccc caagcccacc ct                                    32

<210> SEQ ID NO 24
<211> LENGTH: 36
<212> TYPE: DNA
<213> ORGANISM: Artificial sequence
<220> FEATURE:
<223> OTHER INFORMATION: synthetic oligonucleotide

<400> SEQUENCE: 24
ccagatctct tagaaacacc tgggaccagg agctcc                                36

<210> SEQ ID NO 25
<211> LENGTH: 35
<212> TYPE: DNA
<213> ORGANISM: Artificial sequence
<220> FEATURE:
<223> OTHER INFORMATION: synthetic oligonucleotide

<400> SEQUENCE: 25
ccgatatcag gagcctaccc aaaacccacc ctctc                                 35

<210> SEQ ID NO 26
<211> LENGTH: 36
<212> TYPE: DNA
<213> ORGANISM: Artificial sequence
<220> FEATURE:
<223> OTHER INFORMATION: synthetic oligonucleotide

<400> SEQUENCE: 26
ccagatctgc catggatctg tcctgtgatc aggatg                                36

<210> SEQ ID NO 27
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 27
ctgccctcat gtcttaactt                                                  20

<210> SEQ ID NO 28
<211> LENGTH: 20
<212> TYPE: DNA
<213> ORGANISM: Artificial sequence
<220> FEATURE:
<223> OTHER INFORMATION: synthetic oligonucleotide
```

```
<400> SEQUENCE: 28
gagaatcacc agacacatgc                                              20
```

METHODS AND COMPOSITIONS FOR INHIBITING THE EFFECTS OF AMYLOID BETA OLIGOMERS

CROSS REFERENCE TO RELATED APPLICATIONS

This application is a 371 of International Application No. PCT/US2014/022674 filed Mar. 10, 2014, which claims priority to the filing date of the U.S. Provisional Patent Application Ser. No. 61/777,835 filed Mar. 12, 2013; the full disclosure of which is herein incorporated by reference.

FIELD OF THE INVENTION

This invention pertains to methods of inhibiting the effects of Aβ oligomers on cells and in individuals with Aβ-associated diseases.

BACKGROUND OF THE INVENTION

Soluble oligomeric species of amyloid-β (Aβ) are thought to be key mediators of cognitive dysfunction in Alzheimer's disease (AD) (M. Sheng, et al. (2012) Cold Spring Herb Perspect Biol 4; J. J. Palop et al. (2010) Nat Neurosci 13, 812). Neuritic plaques, a hallmark of Alzheimer's Disease, are accumulations of aggregated, or oligomerized, amyloid beta (Aβ) peptides, including Aβ1-40 (Aβ40) and Aβ1-42 (Aβ42) that are derived from the processing of amyloid precursor protein (APP) by β- and γ-secretases. The vast majority of autosomal familial AD (FAD)-linked mutations are associated with increased levels of Aβ1-42. Transgenic mice expressing elevated levels of human Aβ experience memory loss and synaptic regression (M. Faizi et al., (2012) Brain Behav 2, 142; C. Perez-Cruz et al., (2011) J Neurosci 31, 3926; S. Knafo et al., (2009) Cereb Cortex 19, 586; M. Cisse et al., (2011) Nature 469, 47). Aβ production is thought to be activity-dependent (F. Kamenetz et al., (2003) Neuron 37, 925; J. Wu et al., (2011) Cell 147, 615), and even in wild type mice addition of soluble Aβ oligomers to hippocampal slices or cultures induces loss of long-term 2 potentiation (LTP), increases long-term depression (LTD) and decreases dendritic spine density (G. M. Shankar et al., (2007) J Neurosci 27, 2866; G. M. Shankar et al., (2008) Nat Med 14, 837; H. Hsieh et al., (2006) Neuron 52, 831). There are currently no effective therapies for arresting or reversing the impairment of cognitive function that characterizes AD.

Aβ oligomer levels are also elevated by about 200-300% in Down syndrome (DS) patients throughout life (reviewed in Head and Lott (2004) Curr Opin Neurol 17(2):95-100). The use of a γ-secretase inhibitor to lower β-amyloid levels in young mice that model DS corrected learning deficits characteristic of these mice, suggesting that therapies that interfere with Aβ oligomers will improve cognitive function in young DS patients as well (Netzer W J, et al. (2010) PLoS One 5:e10943).

Recent evidence suggests that Aβ oligomers also contribute to the development of glaucoma, by promoting retinal ganglion cell (RGC) synapse loss and RGC apoptosis. As such, it is expected that targeting the Aβ pathway will provide a therapeutic avenue for glaucoma management (Guo et al. (2007) Proc Natl Acad Sci USA. 104(33):13444-9; Ning et al. (2008) Invest. Ophthalmol. Vis. Sci. 49(11): 5136-5143).

Thus, there is a need in the art for effective therapies for treating Aβ-associated diseases and disorders. The present invention addresses these issues.

SUMMARY OF THE INVENTION

Methods and compositions are provided for reducing the effects of amyloid beta (Aβ) oligomers on a cell. Aspects of the methods generally include providing an agent that prevents Aβ oligomer activation of PirB/LILRB2 protein on cells, or providing a PirB/LILRB2 polypeptide composition to cells to prevent the Aβ oligomer activation of cells mediated by non-PirB/LILRB2 receptors. These methods find many uses, for example, in treating the decline in CNS function in individuals suffering from an Aβ-associated disease or disorder, and for screening candidate agents to identify new therapeutics that interfere with these toxic effects of Aβ in individuals having an Aβ-associated disease or disorder.

In some aspects of the invention, methods for inhibiting synapse loss in the presence of Aβ oligomers in an individual, methods for promoting synaptic plasticity in the presence of Aβ oligomers in an individual, methods of treating an Aβ oligomer-associated nervous system disease or disorder in an individual, or methods treating cognitive decline associated with the presence of Aβ oligomers in an individual, are provided.

In some embodiments, the methods comprise administering to the individual an effective amount of an agent to inhibit Aβ oligomer activation of PirB/LILRB2. In some embodiments, the agent inhibits Aβ oligomer activation of PirB/LILRB2 by inhibiting Aβ oligomer binding to PirB/LILRB2. In some embodiments, the agent comprises a PirB/LILRB2 polypeptide. In some embodiments, the PirB/LILRB2 polypeptide comprises the first two Ig-like domains of PirB or LILRB2. In some embodiments, the PirB/LILRB2 polypeptide consists essentially of the first two Ig-like domains of PirB or LILRB2. In some embodiments, the agent comprises a dimer of PirB/LILRB2 polypeptides. In some embodiments, each PirB/LILRB2 polypeptide of the dimer is fused to an Fc domain. In some embodiments, each PirB/LILRB2 polypeptide of the dimer comprises the first two Ig-like domains of PirB or LILRB2. In some embodiments, each PirB/LILRB2 polypeptide of the dimer consists essentially of the first two Ig-like domains of PirB or LILRB2. In some embodiments, the agent is an antibody that binds to amino acid residues within the first or second Ig-like domain of PirB or LILRB2. In other embodiments, the agent inhibits Aβ oligomer activation of PirB/LILRB2 by inhibiting Aβ oligomer-induced PirB/LILRB2 activation of downstream proteins. In some embodiments, the downstream protein is cofilin, PP2A, PP2B or PP2C.

In some embodiments, the methods comprise administering to the subject an effective amount of a PirB/LILRB2 polypeptide to block Aβ oligomer binding to non-PirB/LILRB2 receptors of Aβ. In some embodiments, the PirB/LILRB2 polypeptide comprises the first two Ig-like domains of PirB or LILRB2. In some embodiments, the PirB/LILRB2 polypeptide consists essentially of the first two Ig-like domains of PirB or LILRB2. In some embodiments, the agent comprises a dimer of PirB/LILRB2 polypeptides. In some embodiments, each PirB/LILRB2 polypeptide of the dimer is fused to an Fc domain. In some embodiments, each PirB/LILRB2 polypeptide of the dimer comprises the first two Ig-like domains of PirB or LILRB2.

In some embodiments, the disease or disorder is Alzheimer's Disease or Down syndrome. In some such embodiments, the method further comprises measuring cognition in the subject. In some embodiments, the disease or disorder is glaucoma. In some such embodiments, the method further comprises measuring visual acuity in the subject.

In some aspects of the invention, compositions are provided, the compositions finding use in the methods of the invention. In some embodiments, the composition comprises a PirB/LILRB2 polypeptide consisting essentially of the first two Ig-like domains of PirB or LilRB2. In some embodiments, the composition comprises a dimer of polypeptides, the dimer comprising a first polypeptide comprises a dimerizing Fc domain fused to a PirB/LILRB2 polypeptide consisting essentially of the first two Ig-like domains of PirB or LILRB2, and a second polypeptide comprises a dimerizing Fc domain fused to a PirB/LILRB2 polypeptide consisting essentially of the first two Ig-like domains of PirB or LILRB2. In some embodiments, the dimerizing Fc domain is human IgG1-Fc.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

The patent or application file contains at least one drawing executed in color. Copies of this patent or patent application publication with color drawing(s) will be provided by the Office upon request and payment of the necessary fee.

FIG. 1A-1K demonstrates that PirB is a receptor for oligomeric Aβ. Monomeric (mono) or oligomerized (oligo) synthetic human Aβ42 peptides (FIG. 5A) (21, 22) were analyzed by (FIG. 1A) size exclusion column chromatography (arrows indicate monomeric form, V0: void volume) and (FIG. 1B) by Western blotting with anti-Aβ antibody (4G8; detects Aβ17-24). (FIG. 1C) PirBIRES-EGFP (top) or control IRES-EGFP (bottom) transfected HEK293 cells (green) were treated with mono- or oligo-Aβ42 (100 nM total peptide, monomer equivalent), and bound Aβ42 (red) was visualized. See also FIG. 5. (FIG. 1D) Quantification of Aβ42 binding represented in (FIG. 1C). AU: average signal/pixel; Mean±SEM; PirB-IRES-EGFP (n=5), IRES-EGFP (n=4). (FIG. 1E) PirB-expressing cells were treated with oligo-Aβ42 (100 nM) and immunostained for Aβ and PirB. Co-localization is observed particularly at cell membrane (i.e. arrowheads). (FIG. 1F) Schematic of mouse PirB and highly related mouse PirA1 and PirA4, or a rat PirB isoform (23). Amino acid sequence similarities to mouse PirB (% Score, ClustalW) are indicated at bottom. (FIG. 1G) Relative oligo-Aβ42 (200 nM) binding to mouse PirB-PirA1- and PirA4- or to rat PirB-expressing HEK293 cells; see also FIG. 7. Mean±SEM (n=4-5). (FIG. 1H to 1J) Dose-dependent binding of mono (squares) or oligo (circles)-Aβ42 to control-(IRES-EGFP; green) or PirB (PirB-IRESEGFP; red)-expressing HEK293 cells, assessed as a function of Aβ42 total concentration (FIG. 1H). Values from control cells were subtracted (ΔPirB=PirB-IRES-EGFP minus IRE-SEGFP) to measure specific binding and saturation curves (FIG. 1I), and scatchard plots (FIG. 1J) were drawn. Mean±SEM (n=4). Calculated Kd=180±52 nM; see also FIG. 8A-8B. (FIG. 1K) Binding of oligo-Aβ42 to cultured cortical neurons (DIV21) is diminished ~50% by deletion of PirB (PirB-/-), as assessed by alkaline phosphatase assay (Mean±SEM, n=6). Estimated Kd for neuronal PirB (dashed line: ΔPirB=WT minus PirB-/-) is 110 nM.

FIG. 2A-2H provides evidence that LilrB2 is a PirB ortholog present in human brain and acts as a receptor for Aβ oligomers via D1D2 domain. (FIG. 2A) Schematic of LilrB1, 2, 3 and Kir (3DL1), human homologs of mouse PirB. Amino acid sequence homologies (% Score, ClustalW) to PirB or to LilrB2 are given at bottom. (FIG. 2B) Aβ42 oligomer (200 nM) selectively binds to LilrB2-expressing HEK293 cells but not to LilrB1-, LilrB3- or to Kir-expressing cells (AU); see FIG. 9A. Similar LilrB1-3 expression levels were verified by Western blotting (inset) with anti-Myc antibodies. Data are mean±SEM (n=5). (FIGS. 2C and 2D) Dose dependence of monomeric (squares) or oligomeric (circles) Aβ42 binding to LilrB2 expressed in HEK293 cells (ΔLilrB2); Mean±SEM (n=4). Kd=206±65 nM; see also FIGS. 9A, 9B and 9C. (FIG. 2E) LilrB2 is expressed in frontal lobe of specimens from 3 adult humans (non-AD; C1-C3) and from 4 Alzheimer's patients (AD1-AD4) (Table 1). Protein extracts from fresh frozen frontal lobe were immunoprecipitated with control IgG or LilrB2-specific antibodies followed by Western blot analysis. (FIG. 2F) Quantitation of LilrB2 protein levels shown in (FIG. 2E). Mean±SEM. (FIG. 2G) Deletion of the D1D2 domain abrogates binding of Aβ42 oligomers to PirB and LilrB2. Top: schematic of PirB and LilrB2 ectodomain constructs: full-length or IgG domain deleted-fused to human IgG-Fc (hIgG-Fc). Bottom: bar graphs of average band intensities±SEM from experiments such as that shown in FIG. 10C (n=3; see also FIG. 2H). Note that sequence analysis using pairwise alignment indicates that the D1D2 domain of LilrB2 aligns closely with the D1D2 domain of PirB (28). (FIG. 2H) PirB- or LilrB2-Fc binds predominantly to high-n oligomeric forms of Aβ42. Oligomerized Aβ42 (input; also contains low-n oligomers and monomeric Aβ42) were subjected to immunoprecipitation with full-length or truncated soluble PirB- or LilrB2-Fc proteins followed by Western blot analysis. Aβ oligomer binding domain-deficient PirB (D5D6)-Fc treatment was used as negative controls (lane 1). Top, right: Western blot with anti-Aβ antibodies specific for oligomeric forms (OMAB; see FIG. 10D); Bottom, left: quantification of Aβ42 binding. Normalized average band intensities±SEM (n=3).

FIG. 3A-3I demonstrates that PirB deletion rescues synaptic plasticity and behavioral deficits in AD models. (FIG. 3A) Acute application of oligo-Aβ42 inhibits LTP in WT hippocampal slices. Field excitatory postsynaptic potentials (fEPSPs) were recorded from stratum radiatum in the CA1 region of hippocampal slices from 4-5 month old WT mice with or without addition of oligo-Aβ42 (200 nM total peptide). Top panels show example fEPSP traces immediately before (light traces) and 45 min after (heavy traces) TBS; each is an average of 5 individual consecutive traces. Calibration bar=0.5 mV/5 ms. The slope of the fEPSP following TBS, relative to baseline, is plotted as a function of time in lower panel. Vehicle (n=7 animals; 9 slices), Aβ42 oligomer (n=6; 9 slices). (FIG. 3B) Aβ42 oligomer does not block LTP in PirB-/- slices. Vehicle (n=5 animals; 8 slices), Aβ42 oligomer (n=4; 6 slices). (FIG. 3C) Histograms of fEPSP slope measured at 45 min after TBS. Each is a 2 min average of recordings taken from all slices of a given condition at time marked "#" in (FIG. 3A) and (FIG. 3B); all data are Mean±SEM, *** P<0.0001, t-test. (FIG. 3D) Comparison of Aβ42 oligomer effects on hippocampal LTP from WT vs PirB-/- mice; replotted from (FIG. 3A) and (FIG. 3B). (FIG. 3E) Novel object recognition memory of 9-month-old mice was evaluated by measuring % of time mice spent exploring a novel vs familiar object during a 10-min test session. (FIG. 3F) Novel place recognition memory (9-month-old) reflects % time mice spent exploring familiar objects whose locations were or were not changed. Values are mean±SEM, * P<0.05, paired t-test. PirB+/−;

APP/PS1 (PirB+/− Tg, n=6), PirB−/−; APP/PS1 (PirB−/− Tg, n=5). (FIG. 3G) Schematic of mouse visual system showing connections from eyes to lateral geniculate nucleus (LGN) to visual cortex. Cortical binocular zone (BZ) receives inputs from both eyes via the LGN. (FIG. 3H) In situ hybridization for Arc mRNA (digoxigenin labeled antisense riboprobe) in visual cortex BZ of PirB; APP/PS1 littermates. At P22, one eye was removed; 10-days later (P32) induction of mRNA for the immediate early gene Arc at P32 was used to monitor width of territory receiving functional input from the open (ipsilateral) eye. Note that high Arc mRNA expression in layer 2/3 neurons within dashed lines, denoting domain of Arc induction in visual cortex. Scale bar, 500 μm. (FIG. 3I) Quantification of expansion in width of Arc mRNA signal in L2/3 visual cortex shown in (FIG. 3H). Data are mean±SEM; *** P<0.001, t-test; PirB+/− (n=14 animals), PirB+/− Tg (n=7), PirB−/− (n=14), PirB−/− Tg (n=10).

FIG. 4A-4I shows that Cofilin is recruited and activated by PirB in an Aβ-dependent manner in vivo and in vitro and is altered in Human AD frontal cortex. (FIG. 4A) PirB interacts with cofilin in vivo in PirB+/− Tg mice (P30, forebrain), assessed by immunoprecipitation for PirB. Other known PirB-proximal signaling and interactions such as tyrosine phosphorylation of PirB and SHP-2 recruitment to PirB are not altered in PirB+/− vs PirB+/− Tg mice. Representative data are shown (n>2). (FIG. 4B and FIG. 4C) Cofilin phosphorylation is reduced in both (FIG. 4B) juvenile (P30, forebrain) and (C) adult (P200, hippocampal synaptosomes) PirB+/−; APP/PS1 (PirB+/− Tg) mice compared to PirB+/− mice, and this reduction is rescued by PirB deletion (PirB−/− Tg). No significant alterations in LIM kinase (LIMK) 1/2 phosphorylation (Thr508/Thr505) were detected. (FIG. 4D and FIG. 4E) Quantificaton of cofilin phosphorylation (left, expressed as pCofilin/total Cofilin) and pLIMK levels (right) represented in (B) and (FIG. 4C). (FIG. 4D) Mean±SEM from 4 independent experiments (13 animals/genotype) shown in (B). * P<0.05, U-test. (FIG. 4E) Mean±SEM (n=3; ** P<0.01, t-test) shown in (FIG. 4C). (FIG. 4F) Cortical neurons (DIV18-22) isolated from WT or PirB−/− embryos (E16) were treated with oligo-Aβ42 (100 nM) for 1 hr (top panels) or 24 hr (middle panels) and cofilin signaling or PSD-95 levels were analyzed by Western blotting. Anti-Tuj1 (βIII-tubulin) antibodies detect neuronal tubulin. Bottom panels: expression of PirB in these neurons detected by PirB immunoprecipitation. (FIG. 4G) Summary of cofilin phosphorylation (Left; * P<0.05, U-test, n=7) or PSD-95 levels (Right; * P<0.05, U-test, n=6) represented in (FIG. 4F). (FIG. 4H) Increased cofilin activity and Tau phosphorylation (Ser396) in human frontal cortex specimens from Alzheimer's patients (AD1-4) compared to non-AD adults (C1-3) (Table 1), assessed by Western blot analysis. (FIG. 4I) Summary of cofilin phosphorylation cases represented in (FIG. 4H). Mean±SEM,* P<0.05, t-test.

(FIG. 5A) Preparation of mono- and oligo-Aβ42. Freshly prepared monomeric Aβ42 peptides (total peptides, 100%) were oligomerized as described in materials and methods, and precipitates were discarded by centrifugation; Aβ42 oligomers remaining in solution (supernatant, 40-50%) were used as oligo-Aβ42 in this study (see also FIGS. 1A and 1B). (FIG. 5B and FIG. 5C) PirB or control empty vector (EV)-transfected HEK293 cells were treated with biotinylated mono- or oligo-Aβ42 (100 nM total peptide), or vehicle and Aβ binding to PirB was assessed by immunoprecipitation for PirB (FIG. 5B) using anti-PirB (4730) antibodies, or Aβ (FIG. 5C) using streptavidin-agarose beads followed by Western blot analysis. PirB interacts preferentially with oligomeric forms of Aβ42.

FIG. 7A-7D Oligo-Aβ42 selectively binds to PirB. (FIG. 7A) PirB or closely related PirA1 and PirA4, or control vector was transfected to HEK293 cells and the expression of these receptors on the cell surface were visualized by immunostaining with anti-PirA/B antibodies in a membrane non-permeabilized condition (T. Kim et al. (2009) "NRH2 is a trafficking switch to regulate sortilin localization and permit proneurotrophin-induced cell death." Embo J 28, 1612). (FIG. 7B) Oligo-Aβ42 (200 nM) selectively binds to HEK293 cells expressing mouse PirB. Minimal binding is seen in mouse PirA1- and PirA4- or rat PirB-expressing cells (see also FIG. 1F and FIG. 1G). (FIG. 7C) Expression levels of mouse PirA1, PirA4 and PirB, or rat PirB in heterologous cells were assessed by Western blotting with anti-Myc antibodies. (FIG. 7D) PirB- or PirA4-expressing HEK293 cells were treated with 0, 100 or 400 nM Aβ42 oligomers, and cell lysates were immunoprecipitated for Aβ42 followed by Western blotting for PirA/B. Dose-dependent binding is observed with PirB but not with PirA4.

(FIG. 8A) Aβ42 oligomer binding to PirB-expressing HEK293 cells was assessed by alkaline phosphatase assay. To measure specific binding, values from corresponding control cells (empty vector-transfected) were subtracted and saturation curves were plotted with GraphPad Prism software. Data are mean±SEM (n=4). (FIG. 8B) Scatchard plot analysis of (FIG. 8A). Calculated Kd for Aβ42 oligomer is 160±31 nM.

FIG. 9A-9C demonstrates that oligo-Aβ42 selectively binds to LilrB2. (FIG. 9A) Aβ42 oligomers (200 nM) binds to LilrB2-expressing HEK293 cells but not to closely related LilrB1- or LilrB3-expressing cells. Expression levels for each construct were similar as verified by co-staining with anti-Myc antibodies (LilrB1-3 constructs each contain C-terminal Myc-tag). (FIGS. 9B and 9C) Dose-dependency of Aβ42 oligomer binding to LilrB2-expressing HEK293 cells, assessed by alkaline phosphatase assay (Mean±SEM, n=4). Calculated Kd is 250±67 nM.

(FIG. 10A) Aβ42 oligomers primarily bind to dimeric PirB. Control (EV) or PirB-expressing HEK293 cells were treated with biotinylated Aβ42 oligomer and cell lysates were subjected to immunoprecipitation with streptavidin-beads. Aliquots of samples were either partially reduced in β-mercaptoethanol (β-ME)-deficient Laemmli buffer without boiling (top), or fully reduced by boiling in β-ME plus Laemmli buffer (bottom), followed by Western blot analysis for PirB. In the partially reduced condition, dimeric PirB (~240 kDa) is detected as a dominant form associated with Aβ oligomers (top), in comparison to monomeric PirB (~120 kDa), which is the predominant form detected in the fully reduced condition (bottom). (FIG. 10B) Schematic of PirB ectodomain fused to human IgG-Fc protein. (FIG. 10C) The D1D2 domain of PirB is critical for Aβ42 oligomer binding. Synthetic Aβ42 oligomers were immunoprecipitated using full-length or deleted PirB-Fc proteins followed by Western blot analysis in the fully reduced condition. Bottom, expression levels of PirB-Fc proteins, detected by reprobing with antibody against human IgG-Fc. Right, input oligomerized Aβ42 detected in the fully reduced condition. Note that monomeric Aβ42 is present in the input samples but not in PirB-Fc immunocomplexes. (FIG. 10D) Oligomer-specific antibody, OMAB (M. Lindhagen-Persson (2010) "Amyloid-beta oligomer specificity mediated by the IgM isotype—implications for a specific protective mechanism exerted by endogenous auto-antibodies." PLoS One 5, e13928) detects Aβ42 oligomers but not monomer, assessed by Western blotting in the partially reduced condition.

FIG. 11A-11D illustrates how PirB deletion rescues excessive LTD in juvenile visual cortex of APP/PS1 mice. (FIG. 11A) Schematic of LTD recording configuration in visual cortex slice. Stimulating electrode is in layer 4; recording electrode is positioned in layer 2/3. (FIG. 11B) LTD at L4 to L2/3 synapses in visual cortex slices (P28-P32) was measured as a decrease in fEPSP slope, relative to baseline, following 3 series of 900 pulses at 1 Hz (LFS), spaced 25 min apart. PirB+/− mice (n=5 animals; 11 slices), PirB+/−; APP/PS1 (PirB+/− Tg; n=5; 11 slices), PirB−/− (n=6; 12 slices), PirB−/−; APP/PS1 (PirB−/− Tg; n=4; 12 slices). Top panels: example fEPSP traces immediately before, (light traces) and 60 min after start of LTD induction (heavy traces; each is average of 5 individual traces). Calibration bar=0.5 mV/2 ms. (FIG. 11C) Histograms of fEPSP slope measured at 60 min. Each is a 2 min average recordings taken from all slices of a given condition at time marked "#" in (FIG. 11B) and (FIG. 11D); *** P<0.0001, t-test. (FIG. 11D) Comparison of LTD in visual cortex of APP/PS1 mice in the presence (PirB+/− Tg) vs absence (PirB−/− Tg) of PirB; replotted from (FIG. 11B).

FIG. 15A-15E demonstrates a Cre-ER-dependent strategy for deletion of PirB with temporal control. (FIG. 15A): Cartoon of PirB Protein structure (top) and floxed PirB allele (bottom) before and after Cremediated excision. (FIG. 15B) Daily tamoxifen given via nursing mother (P3-7) induces deletion of the floxed region at P21 as detected by PCR. (FIG. 15C) Western Blots for PirB protein in forebrain at ages of tamoxifen administration and western blotting as indicated at left. (FIG. 15D) Quantification of PirB protein in forebrain after tamoxifen induction via maternal injection from P3-7, normalized to average Cre− levels across all ages assayed: Cre− P21: n=4 mice vs. Cre+P21: n=5, p=0.02, Utest. Cre− P27: n=5 vs. Cre+P27: n=4, p=0.02, U-test. E: Quantification of PirB protein in forebrain at P70 (adult) after tamoxifen injection from P45-9. Cre− P70: n=4 mice vs. Cre+P70: n=4. p=0.03, U-test. * p<0.05

FIG. 16A-16H shows that timed genetic deletion of PirB enhances OD plasticity. (FIG. 16A) Timeline of inducible knockout of PirB and assessment of OD plasticity via Arc mRNA induction. (FIG. 16B) Example micrographs of Arc mRNA in situ hybridizations at P32. Black signal corresponds to neurons hybridized with digoxigenin-labeled Arc antisense mRNA probe in region of visual cortex activated by stimulation of the ipsilateral eye. NR=Normally Reared, ME=Monocular Enucleated, Cre−=PirB flox/flox, Cre+ =UbC-CreERT2; PirB flox/flox. Width of Arc signal in layer 4 (between arrows) was measured. Cortical layers indicated at left; scale bar 500 μm. (FIG. 16C) Cumulative histograms of width of Arc mRNA signal by individual section. NR Cre−: n=41 sections; NR Cre+: n=44; ME Cre−: n=39; ME Cre+: n=52. (FIG. 16D) Graph of data in C, with mean and SEM by animal. Deletion of PirB during the CP enhances OD plasticity, as shown by expansion in width of Arc mRNA signal over that in NR mice. NR Cre−: n=7 mice vs. NR Cre+: n=7, p=0.65; ME Cre−: n=7 vs. ME Cre+: n=7, **** indicates p<0.0001, One-way ANOVA with Tukey post-hoc test. (FIG. 16E) Timeline of inducible deletion of PirB and assessment of OD plasticity in adults. (F) Example Arc mRNA in situ hybridization micrographs from P74 animals, as in B. (FIG. 16G) Cumulative histograms of width of Arc mRNA induction from individual sections. NR Cre−: n=23 sections; NR Cre+: n=20; ME Cre−: n=41; ME Cre+: n=51. (FIG. 16H) Graph of data shown in G with mean and SEM by animal. Deletion of PirB in adulthood enhances OD plasticity. NR Cre−: n=5 mice vs NR Cre+: n=5, p=0.99; ME Cre−: 7 vs ME Cre+: n=8, p=0.013; ME Cre− vs NR Cre−: p=0.18; ME Cre+ vs NR Cre+: p=0.0004, by One-Way ANOVA with Tukey post-test. * p<0.05, *** p<0.001.

(FIG. 17A) Genotyping of samples from ear and cortex from P100 CamKIIa-Cre; PirB flox/flox (cKO) or CamKIIa-Cre; PirBWT (WT), showing deletion of floxed PirB in cerebral cortex but not ear at P100 (FIG. 17B) CamKIIa-Cre; PirB flox/+ breeders were crossed with the Ai14 TdTomato reporter line, generating red fluorescence in the presence of Cre. Sagittal section through visual cortex (layers indicated at right) and hippocampus of a P30 mouse shows Cre present in pyramidal neurons of cortex and hippocampus. (FIG. 17C) Graphs of width of area activated by stimulation of ipsilateral (open) eye in layer 4 of visual cortex, assessed using Arc mRNA induction. Deletion of PirB from excitatory neurons of the forebrain increases open eye expansion in adult mice after ME from P100-110. NR WT: n=5 mice vs. NR cKO: n=4 mice, p=0.91. ME WT: n=8 mice vs. ME cKO: n=5, p=0.006. NR vs. ME WT: p=0.39, NR vs. ME cKO: p=0.0002, by One-way ANOVA with Tukey post-hoc test.  $p<0.01$, * $p<0.001$ FIG. 18A-18I demonstrates that pharmacological blockade of PirB binding either during or after the critical period enhances OD plasticity in WT visual cortex. (FIG. 18A) Schematic of soluble PirB-Myc-His (sPirB) fusion protein, indicating extracellular Ig-like domains plus Myc and His tags. (FIG. 18B) Western blot of culture supernatant from sPirB-transfected HEK293 cells, detecting Myc tag and PirB ectodomain; Myc-His tagged alkaline phosphatase (AP-Myc-His) is a positive control. (FIG. 18C) PirB phosphorylation is decreased after 7 days (P21-28) of sPirB infusion into WT mouse cortex, as shown by phospho-tyrosine IP and PirB western blot of cortical lysates from infused (sPirB Infused), uninfused (sPirB Uninf) hemisphere, or untreated littermate controls. (FIG. 18D) Section of visual cortex immunostained with anti-Myc antibody after 11 day (P21-32) sPirB or BSA infusion (1 mg/mL). Scale bar=1 mm. E-F: Minipump infusions during Critical Period (CP). Timeline as shown. (FIG. 18E) Example Arc mRNA in situ hybridization micrographs of visual cortex after BSA (top), or sPirB (bottom) treatment. Scale bar=500 μm. (FIG. 18F) Graphs comparing width of Arc mRNA signal in layer 4 following open-eye stimulation. Width of territory activated by open-eye stimulation following ME is greater following sPirB infusion than with BSA. NR BSA: n=4 mice, NR sPirB: n=4, ME BSA: n=5 vs. ME sPirB: n=6, $p<0.0001$ by One-Way ANOVA and Tukey post-hoc test for all comparisons indicated. FIG. 18G-18I: sPirB infusions into adult WT visual cortex, timeline as shown. (FIG. 18G) Example in situ hybridization micrographs at P74. (FIG. 18H) Graphs comparing width of Arc mRNA signal in layer 4 following stimulation of the ipsilateral (open) eye. sPirB infusion from P63-74 enhances openeye expansion following ME. NR BSA: n=4 mice vs. NR sPirB: n=4 p=0.99. ME BSA: n=4 vs. ME sPirB: n=5, p=0.0004. NR vs. ME BSA: p=0.88, NR vs. ME sPirB: $p<0.0001$. FIG. 18I: sPirB infusion has no effect on OD plasticity when infused into visual cortex of PirB−/− mice. ME PirB−/− BSA: n=5 mice vs. ME PirB−/− sPirB: n=5, p=0.95, ME PirB−/− BSA vs. ME WT BSA: p=0.034. * $p<0.001$, ** $p<0.0001$ by One-Way ANOVA and Tukey post-hoc test.

FIG. 19A-19H demonstrates that minipump infusion of sPirB increases spine density and functional synapses on L5 pyramidal neurons, and restores spine density following LTMD. (FIG. 19A) Timeline of minipump infusions (1 mg/mL BSA or sPirB from P63-74) and example dendrites of YFP-labeled L5 pyramidal neurons in binocular zone of WT Thy1-YFP-H visual cortex. Scale bar=10 μm. (FIG. 19B) Graphs of spine density on apical tufts of L5 neurons in sPirB infused, but not uninfused (Unif.) contralateral hemisphere or in BSA controls: BSA Infused: n=5 mice vs. sPirB Infused: n=5, p=0.01, 1-2 cells/animal. BSA Uninf.: n=5 vs. sPirB Uninf.: n=5, p=0.96, BSA Inf. vs. Uninf.: p=0.99, sPirB Inf. vs. Uninf.: p=0.016 by One-Way ANOVA and Tukey post-hoc test. (FIG. 19C) Example traces of mEPSC responses recorded from layer 5 pyramidal neurons in BSA and sPirB-treated mice as in A. (FIG. 19D) Increased mEPSC frequency with sPirB infusion: BSA: n=12 neurons vs. sPirB n=13, p=0.046 by Mann-Whitney U Test. (FIG. 19E) No change in mEPSC amplitude: BSA: n=12 neurons vs. sPirB n=13, p=0.70 by Mann-Whitney U Test. FIG. 19F: Timeline of LTMD, recovery, and minipump infusion experiment. (FIG. 19G) Image of a representative cell soma and basolateral dendrites. Scale bar=50 μm. (FIG. 19H) Acute infusion of sPirB enhances basolateral dendritic spine density both at baseline, and after LTMD. (BSA NR: n=5 mice vs. BSA LTMD: n=4, p=0.02. sPirB LTMD: n=5, sPirB vs. BSA LTMD, p=0.001, sPirB NR: n=5 animals, 1-2 cells per animal, sPirB vs. BSA NR: p=0.003. * $p<0.05$, ** $p<0.01$ by One-Way ANOVA and Tukey post-hoc test.

FIG. 20A-20E provides the plasticity Indices for genetic or pharmacological disruption of PirB function. Data from all Arc Induction Experiments, presented as a plasticity index, calculated as width of layer 4 Arc mRNA signal following ME/width of Arc mRNA signal in NR. Index is a measure of the degree to which cortical territory functionally connected to the ipsilateral (open) eye expands following ME over that present in normally reared controls. (FIG. 20A) Inducible Cre-mediated PirB deletion during the critical period plus ME from P28-32 (p=0.001). (FIG. 20B) Inducible Cremediated PirB deletion in adulthood plus ME from P70-74 (p=0.001). (FIG. 20C) CamKIIa-Cre; PirBflox conditional deletion in excitatory neurons of the forebrain plus ME from P100-110. (FIG. 20D) Minipump infusion of sPirB vs BSA in WT mice during the critical period at P21, plus ME from P28-32 (p=0.004). (FIG. 20E) Minipump infusion of sPirB vs BSA in WT mice from P63-74, plus ME from P70-74 (p=0.016). All comparisons made via Mann-Whitney U Test.

FIG. 21A-21F provides a characterization of sPirB minipump infusion area and effect on OD plasticity. (FIG. 21A) Example minipump implantation site located 2.5 mm lateral and 3 mm posterior to bregma, at anterior tip of V1. (FIG. 21B) Anti-Myc immunostain in serial cryosections (16 μm thick) from a P32 mouse after sPirB osmotic minipump infusion, showing diffusion of sPirB caudally into undamaged tissue 2 mm from injection site. (FIG. 21C) No Myc immunostaining evident at the injection site or further caudal in BSA-treated controls. Scale bar=1 mm. (FIG. 21D) Cumulative histograms of width of Arc mRNA induction in layer 4 data by individual section from critical period sPirB minipump experiment shown in FIG. 18E, 18F. sPirB or BSA was infused from P21-32 and ME was performed from P28-32. NR BSA: 4 animals/23 sections, NR sPirB: 4 animals/32 sections, ME BSA: 5 animals/50 sections, ME sPirB: 6 animals/68 section. (FIG. 21E) Cumulative histograms of width of Arc mRNA induction by individual section from adult sPirB experiment shown in FIG. 18F. sPirB or BSA was infused from P63-74 and mice were either normally reared (NR) or received ME from P70-74. NR BSA: 4 animals/20 sections, NR sPirB: 4 animals/21 sections, ME BSA: 4 animals/30 sections, ME sPirB: 5 animals/35 sections. (FIG. 21F) Cumulative histograms of width of Arc mRNA induction by individual section from experiment shown in FIG. 18G in which sPirB or BSA was infused in visual cortex of PirB−/−(KO) mice from P63-74, coupled with ME from P70-74. BSA infusions: n=5 animals/25 sections; sPirB infusions: 5 animals/28 sections.

(FIG. 22A) Spine density data shown by individual cell from experiment shown in FIG. 19B. Changes in spine density resulting from minipump infusions of sPirB or BSA (1 mg/mL) from P63-74 on L5 apical tufts studied in Thy-1 YFP-H WT visual cortex (from FIG. 19B). Data shows spine density on an individual cell basis. See FIG. 19G for analysis per animal. Uninf=uninfused hemisphere contralateral to minipump implantation.  indicates p<0.01; * indicates p<0.001 by one-way ANOVA with Tukey post-test. n=5, 5, 9, 10 YFP-labeled cells. (FIG. 22B) Breakdown by spine type: 11 days of sPirB infusion does not alter distribution of spine types. Data is same experiment as in FIG. 22A. (FIG. 22C) Spine density changes by cell on L5 basolateral dendrites after normal rearing (NR) or long-term monocular deprivation (LTMD) plus subsequent minipump infusion of sPirB or BSA (from FIG. 19E-19G).  indicates p<0.01, * indicates P<0.001, and **** indicates P<0.0001 by one-way ANOVA with Tukey post-test. n=9, 9, 9, 10 cells. (FIG. 22D) 7 days of sPirB infusion has no effect on spine morphology on basolateral dendrites of L5 pyramidal neurons after LTMD; same sample as in FIG. 22C.

DETAILED DESCRIPTION OF THE INVENTION

Figures 5A, 5B, 5C:
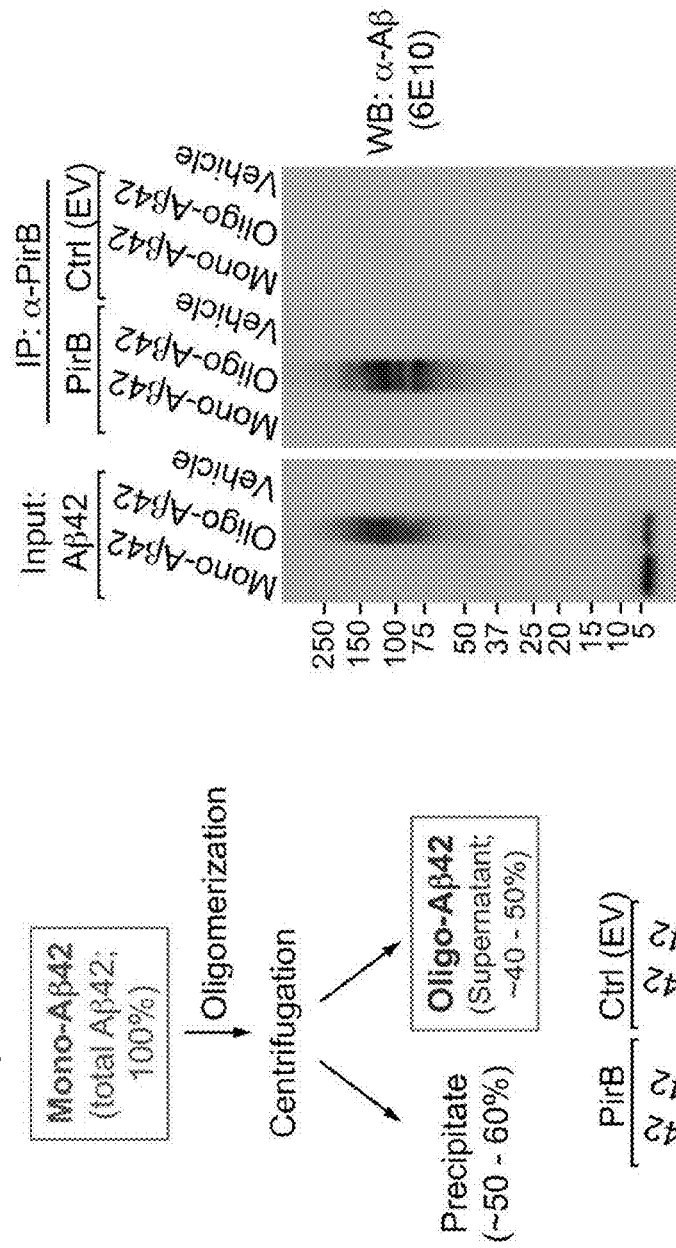
FIG. 5A-5C demonstrates that PirB interacts with oligomeric Aβ42.

Methods and compositions are provided for reducing the effects of amyloid beta (Aβ) oligomers on a cell. Aspects of the methods generally include providing an agent that prevents Aβ oligomer activation of PirB/LILRB2 protein on cells, or providing a PirB/LILRB2 polypeptide composition to cells to prevent the Aβ oligomer activation of cells mediated by non-PirB/LILRB2 receptors. These methods find many uses, for example, in treating the decline in CNS function in individuals suffering from an Aβ-associated disease or disorder, and for screening candidate agents to identify new therapeutics that interfere with these toxic effects of Aβ in individuals having an Aβ-associated disease or disorder. These and other objects, advantages, and features of the invention will become apparent to those persons skilled in the art upon reading the details of the compositions and methods as more fully described below.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention.

Further, the dates of publication provided may be different from the actual publication dates which may need to be independently confirmed.

Compositions

In aspects of the invention compositions are provided for inhibiting the effects of Aβ oligomers on cells. By Aβ, or "amyloid beta", or "amyloid β", it is meant a peptide of 36-43 amino acids that is derived from the processing of amyloid precursor protein (APP) by β- and γ-secretases. By "Aβ oligomers", "amyloid β oligomers", or "amyloid beta oligomers" it is meant aggregates of Aβ peptide. Aβ is the main component of deposits, called amyloid plaques, found in the brains of patients with Alzheimer's disease (AD) and cerebral amyloid angiopathy (CAA); it also associated with retinal ganglion cells in patients having glaucoma. Two major variants, $A\beta_{1-40}$ ("Aβ40") (DAEFRHDSGYEVH-HQKLVFFAEDVGSNKGAIIGLMVGGVV) and $A\beta_{1-42}$ ("Aβ42") (DAEFRHDSGYEVHHQKLVFAAEDVGSNK-GAIIGLMVGGVVIA), are produced by alternative carboxy-terminal truncation of APP (Selkoe et al. (1988) *Proc. Natl. Acad. Sci. USA* 85:7341-7345; Selkoe, (1993) *Trends Neurosci* 16:403-409). $A\beta_{1-42}$ is the more fibrillogenic and more abundant of the two peptides in amyloid deposits of both AD and CAA. Other naturally occurring variants include, e.g., $A\beta_{1-28}$ (DAEFRHDSGYEVHHQAAVFAAE-DVGSNK), Aβ12-28 (VHHQKLVFFAEDVGSNKC), $A\beta_{1-37}$ (DAEFRHDSGYEVHHQKLVFFAEDVGSNK-GAIIGLMVG), $A\beta_{1-38}$ (DAEFRHDSGYEVHHQKLVF-FAEDVGSNKGAIIGLMVGG), $A\beta_{1-39}$ (DAEFRHDS-GYEVHHQKLVFFAEDVGSNKGAIIGLMVGGV), $A\beta_{1-43}$ (DAEFRHDSGYEVHHQKLVFFAEDVGSNK-GAIIGLMVGGVVIAT), $A\beta_{1-44}$ (DAEFRHDSGYEVH-HQKLVFFAEDVGSNKGAIIGLMVGGVVIATV), $A\beta_{1-45}$ (DAEFRHDSGYEVHHQKLVFFAEDVGSNKGAIIGLMVGGVVIATVI), $A\beta_{1-46}$ (DAEFRHDSGYEVHHQKLVFFAEDVGSNKGAIIGLMVGGVVIATVIV), $A\beta_{1-47}$ (DAEFRHDSGYEVHHQKLVFFAEDVGSNKGAIIGLMVGGVVIATVIVI), $A\beta_{1-48}$ (DAEFRHDSGYEVHHQKLVFFAEDVGSNKGAIIGLMVGGVVIATVIVIT), $A\beta_{1-49}$ (DAEFRHDSGYEVHHQKLVFFAEDVGSNKGAIIGLMVGGVVIATVIVITL), $A\beta_{1-55}$ (DAEFRHDSGYEVHHQKLVFFAEDVGSNKGAIIGLMVGGVVIATVIVITLVMLKKK), $A\beta_{2-40}$ (AEFRHDSGYEVHHQKLVFFAEDVGSNKGAIIGLMVGGVV), and $A\beta_{3-40}$ (EFRHDSGYEVHHQKLVFFAEDVGSNKGAIIGLMVGGVV), as well as derivatives of the above peptides comprising a naturally occurring substitution, e.g. $A\beta_{1-42}$ H13R, $A\beta_{1-42}$ V18A, $A\beta_{1-42}$ F19P, $A\beta_{1-42}$ E22D, $A\beta_{1-42}$ E22V, $A\beta_{1-42}$ E22A, $A\beta_{1-42}$ D23A, $A\beta_{1-42}$ G25A, $A\beta_{1-42}$ N27A, $A\beta_{1-42}$ K28A, $A\beta_{1-42}$ G29A, $A\beta_{1-42}$ I31A, $A\beta_{1-42}$ G37A, the English Mutation, the Iowa Mutation, the Tottori-Japanese Mutation, the Flemish Mutation, the Arctic Mutation, the Italian Mutation, etc. In addition to the amyloid deposits that may occur in, for example, CNS tissue, amyloid deposition may occur in the vascular walls (Hardy (1997); Haan et al. (1990); Vinters (1987); Itoh et al. (1993); Yamada et al. (1993); Greenberg et al. (1993); Levy et al. (1990)). These vascular lesions are the hallmark of CAA, which can exist in the absence of AD.

Aβ oligomers are known in the art to have a number of effects on cells. These include, for example, reducing cell viability, and reducing synaptic plasticity, promoting synapse loss in neurons. By a "synapse" it is meant the structure on a neuron that permits the neuron to pass an electrical or chemical signal to another cell. By "synaptic plasticity" it is meant the ability of the synapse to change in strength, i.e. to become stronger or weaker, in response to either use or disuse, respectively, of transmission over that synaptic pathway. Such a change in strength is typically evident by one or more of the following structural changes: a change in the number of presynaptic vesicles, a change in the amount of neurotransmitter loaded per vesicle, a change in the number of dendritic spines, and/or a change in the number of neurotransmitter receptors positioned on the postsynaptic neuron. Reductions or enhancements in synaptic plasticity may be observed by assessing the ability of a postsynaptic neuron to evoke a long-term enhancement ("long term potentiation", LTP) or long-term depression (LTD) in the activity of a presynaptic neuron, and/or by assaying for the subsequent changes in synaptic strength, e.g. by detecting one or more of the above-mentioned structural changes. By "enhanced synaptic plasticity" it is meant greater synaptic strengthening (LTP), more stable synapses and a failure to remove synapses and the spines that carry synapses. By "reduced synaptic plasticity" it is meant enhanced synaptic weakening (LTD), less stable synapses, and fewer spines and synapses. By "synapse loss" it is meant a decrease in the number of synapses, for example, a loss in the connection between two neurons or, in instances in which multiple synapses exist between two neurons, in the loss of one or more of these synapses. As is well known in the art, synaptic activity and the change in the strength and number of synapses is central to almost all neurobiological processes, including learning, memory, and neuronal development. In further describing aspects of the invention, the following description focuses on the effects of Aβ oligomers on neurons. However, the subject methods and compositions also find use in inhibiting the effects of Aβ oligomers on other types of cells as well, for example, microglia.

The subject compositions find use in inhibiting the effects of Aβ oligomers on cells, e.g. neurons, and on tissue function, e.g. central nervous system function. By inhibiting the effects of Aβ oligomers on a cell, it is meant decreasing, reducing, mitigating, suppressing, or otherwise antagonizing one or more effects of the Aβ oligomers on the cell, e.g. the reduction in synaptic plasticity, the loss of synapses, the loss of viability etc. that occurs in neurons in the presence of Aβ oligomers. By inhibiting the effects of Aβ oligomers on CNS function, it is meant decreasing, reducing, mitigating, suppressing, or otherwise antagonizing one or more effects of the Aβ oligomers on the function of the CNS, e.g. the cognitive or visual decline, the impaired cognitive or visual function, etc. that occurs in the presence of Aβ oligomers.

In some instances, the subject compositions may be employed to reduce the effects of Aβ oligomers on cells and/or tissue function, e.g., CNS function by 20% or more, e.g. by 30% or more, by 40% or more, or by 50% or more, in some instances by 60% or more, by 70% or more, by 80% or more, or by 90% or more, in some cases by about 100%, i.e. to negligible amounts. In some instances, the subject compositions may be used to reverse one or more of the effects of Aβ oligomers on neurons, or one or more of the adverse effects of Aβ oligomers on an individual's neuronal function. Put another way, the subject compositions may be administered to prevent synapse loss and permit synapse formation in the presence of Aβ oligomers, and to decrease the rate of cognitive or visual decline, stabilize cognitive or visual function, and in some instances improve cognition or vision in an individual suffering from an Aβ-associated disease or disorder.

Without wishing to be bound by theory, as demonstrated by the working examples below, the present inventors have discovered that Aβ oligomers exert their effects on neurons and, hence, CNS function, at least in part by binding to and activating PirB and PirB-related orthologs on neurons. By antagonizing Aβ oligomer—PirB/LilrB2 signaling, synapse loss may be mitigated and synaptic plasticity restored, thereby permitting and even promoting the formation of new synapses in the presence of Aβ oligomers. Accordingly, in some embodiments, the subject compositions inhibit binding of Aβ oligomers to PirB/LILRB2 on the surface of a cell, such that the cell's PirB/LILRB2 receptors do not become activated by the Aβ oligomers. In some embodiments, the compositions inhibit signaling by PirB/LILRB2 in the cell, such that the cell cannot become activated by PirB/LILRB2.

Additionally, because PirB/LILRB2 polypeptides bind Aβ oligomers, soluble PirB/LILRB2 polypeptides may be used to block the binding of Aβ oligomers to other Aβ receptors, e.g. the NMDA receptor (Snyder et al. (2005) Nat Neurosci. 8(8):1051-8), cellular prion protein (Laurén J, et al. (2009) Nature 457(7233):1128-32), the receptor tyrosine kinase EphB2 (Cissé M, et al. (2011) Nature 469(7328):47-52), the receptor for advanced glycation end products ("RAGE", Origlia N, et al. (2008) J Neurosci. 28(13):3521-30), metabotropic glutamate receptor 5 (Um J W, et al. (2013) Neuron 79(5):887-902), and the immune cell receptor FcγRIIb (Kam T, et al. J Clin Invest. 2013 Jun. 10), so as to antagonize the toxic effects of Aβ oligomers that are mediated by these other receptors. Accordingly, in some embodiments, the subject compositions inhibit binding of Aβ oligomers to a cell, such that cell does not become activated by the Aβ oligomers.

Thus, in some embodiments, the subject compositions inhibit binding of Aβ oligomers to a cell, such that cell does not become activated by the Aβ oligomers. In certain such embodiments, the compositions inhibit binding of Aβ oligomers to PirB/LILRB2 on a cell, such that the cell's PirB/LILRB2 receptors do not become activated by the Aβ oligomers. In some embodiments, the subject compositions inhibit signaling by PirB/LILRB2 in the cell, such that the cell cannot become activated by PirB/LILRB2.

PirB was first described by Kubagawa et al., Proc. Nat. Acad. Sci. USA 94:5261-6 (1997). Mouse PirB has several human orthologs, which are members of the leukocyte immunoglobulin-like receptor, subfamily B (LILRB), and are also referred to as "immunoglobulin-like transcripts" (ILTs). The human orthologs show significant homology to the murine sequence, from highest to lowest in the following order: LILRB3/ILT5, LILRB1/ILT2, LILRB5/ILT3, LILRB2/ILT4. LILRB3/ILT5 (Genbank Accession No. NP_006855) and LILRB1/ILT2 (Genbank Accession No. NP_006660) were first described by Samaridis and Colonna, Eur. J. Immunol. 27(3):660-665 (1997). LILRB5/ILT3 (Genbank Accession No. NP_006831) was identified by Borges et al., J. Immunol. 159(11):5192-5196 (1997). LILRB2/ILT4/MIR10 (Genbank Accession Nos. NM_005874 (variant 1) and NM_001080978.2 (variant 2)), was identified by Colonna et al., J. Exp. Med. 186:1809-18 (1997). PirB and its human orthologs show a great degree of structural variability.

As known in the art, PirB/LILRB polypeptides are MHC Class I (MHCI) inhibitory receptors, and are known for their role in regulating immune cell activation (Kubagawa et al., supra; Hayami et al., J. Biol. Chem. 272:7320 (1997); Takai et al., Immunology 115:433 (2005); Takai et al., Immunol. Rev. 181:215 (2001); Nakamura et al. Nat. Immunol. 5:623 (2004); Liang et al., Eur. J. Immunol. 32:2418 (2002)). Additionally, PirB is expressed in subsets of neurons throughout the brain. In mutant mice lacking functional PirB, cortical ocular dominance (OD) plasticity is significantly enhanced at all ages, suggesting PirB's play a role in restricting activity-dependent plasticity in visual cortex (Syken et al. (2006) Science 313:1795-800).

The terms "paired-immunoglobulin-like receptor B" and "PirB" are used herein interchangeably, and refer to a native-sequence, 841-amino acid mouse inhibitory protein of GenBank Acccession No. NP_035225, and its native-sequence homologues in rat and other non-human mammals, including all naturally occurring variants, such as alternatively spliced and allelic variants and isoforms, as well as soluble forms thereof. For further details see, Kubagawa et al., Proc Natl Acad Sci USA 94, 5261 (1997). The terms "PirB gene product", "PirB polypeptide", "PirB peptide", and "PirB protein" are used interchangeably herein to refer to native PirB polypeptides, PirB polypeptide variants, PirB polypeptide fragments and chimeric PirB polypeptides.

The terms "LILRB," "ILT" and "MIR," are used herein interchangeably, and refer to all members of the human "leukocyte immunoglobulin-like receptor, subfamily B", including all naturally occurring variants, such as alternatively spliced and allelic variants and isoforms, as well as soluble forms thereof. Individual members within this B-type sub-family of LILR receptors are designated by numbers following the acronym, such as, for example, LILRB3/ILT5, LILRB1/ILT2, LILRB5/ILT3, and LILRB2/ILT4, where a reference to any individual member, unless otherwise noted, also includes reference to all naturally occurring variants, such as alternatively spliced and allelic variants and isoforms, as well as soluble forms thereof. Thus, for example, "LILRB2," "LIR2," and "MIR10" are used herein interchangeably and refer to the 598-amino acid polypeptide of Genbank Accession No. NM_005874, and its naturally occurring variants such as alternatively spliced and allelic variants and isoforms, e.g. Genbank Accession No. NM_001080978.2, as well as soluble forms thereof. For further details, see Martin et al., Trends Immunol. 23, 81 (2002). The terms "LILRB gene product", "LILRB polypeptide", "LILRB peptide", and "LILRB protein" are used interchangeably herein to refer to native LILRB polypeptides, LILRB polypeptide variants, LILRB polypeptide fragments and chimeric LILRB polypeptides.

By "native polypeptide" it is meant a polypeptide found in nature. For example, native PirB polypeptides includes mouse PirB, the sequence for which may be found at GenBank Accession No. NP_035225, as well as PirB homologs that naturally occur in other non-human mammals and naturally occurring PirB variants, e.g. isoforms. Likewise, native LILRB polypeptides include LILRB2, the sequence for which may be found at GenBank Accession No. NP_005865, as well as LILRB2 homologs that naturally occur in humans and naturally occurring LILRB2 variants, e.g. isoforms. By "variant" it is meant a mutant of the native polypeptide having less than 100% sequence identity with the native sequence. For example, a variant may be a polypeptide having 60% sequence identity or more with a full length native PirB, e.g. 65%, 70%, 75%, or 80% or more identity, such as 85%, 90%, or 95% or more identity, for example, 98% or 99% identity with the full length native PirB. Variants also include fragments of a native PirB polypeptide that interact with Aβ oligomers, e.g. a fragment comprising residues 24-224 of PirB or the comparable sequence in a PirB homolog or ortholog. Variants also include polypeptides that have Aβ oligomer binding activity and 60% sequence identity or more with a fragment of a native PirB polypeptide, e.g. 65%, 70%, 75%, or 80% or more identity, such as 85%, 90%, or 95% or more sequence identity, for example, 98% or 99% identity with the comparable fragment of the native PirB polypeptide.

The term "PirB/LILRB" is used herein to jointly refer to the corresponding mouse and human proteins and native sequence homologues in other non-human mammals, including all naturally occurring variants, such as alternatively spliced and allelic variants and isoforms, as well as soluble forms thereof. The term "PirB/LILRB2" is used herein to jointly refer to the mouse PirB protein (GenBank Accession Nos. NM_011095.2 and NP_035225, SEQ ID NO:1 (protein), SEQ ID NO:2 (cDNA)), the human LILRB2 protein (GenBank Accession Nos. NM_005874 and NP_005865; SEQ ID NO:3 (protein) and SEQ ID NO:4 (cDNA)), and the corresponding PirB protein in other non-human mammals, including all naturally occurring variants, such as alternatively spliced and allelic variants and isoforms, as well as soluble forms thereof.

As demonstrated in the working examples below, Aβ oligomers, e.g. aggregates of $A\beta_{1-40}$ (Aβ40), $A\beta_{1-42}$ (Aβ42), etc. bind to PirB/LILRB2 in vitro and in vivo. More particular, Aβ oligomers bind to PirB polypeptide comprising the first two Ig-like domains of PirB, i.e. residues 24-224 of SEQ ID NO:1. In humans, Aβ oligomers bind to LILRB2, and more particularly to LILRB2 polypeptides comprising the first two Ig-like domains of LILRB2, i.e. residues 24-223 of SEQ ID NO:3. As such, in some aspects of the invention, the effects of Aβ oligomers on neurons and the impact of Aβ oligomers on CNS function, e.g. cognition or vision, in individuals is inhibited by providing an agent that inhibits PirB/LILRB2 signaling induced by Aβ oligomers, e.g. oligomers of Aβ40 or Aβ42, in PirB/LILRB2-expressing neurons.

Non-limiting examples of agents that inhibit Aβ oligomer-induced PirB/LILRB2 signaling that may be used in the subject compositions include those that inhibit the binding of Aβ oligomers to cellular PirB/LILRB2. By inhibiting the binding of Aβ oligomers to PirB/LILRB2 it is meant reducing, inhibiting, antagonizing, or blocking, the interaction between Aβ oligomers and PirB/LILRB2 by 20% or more, for example by 30% or more, by 40% or more, or by 50% or more, in some instances, by 60% or more, by 70% or more, by 80% or more, e.g. by 90% or more, by 95% or more, or by 100%, i.e. to negligible amounts. Any convenient agent that inhibits the binding of Aβ oligomers to PirB/LILRB2, e.g. as described herein, may be used. For example, Aβ oligomer binding to PirB/LILRB2 may be inhibited with PirB/LILRB2-specific antibodies, small molecules that bind to PirB/LILRB2 and inhibit binding of Aβ, or soluble PirB/LILRB2 polypeptides, e.g. PirB/LILRB2 polypeptide comprising the first two Ig-like domains of PirB (residues 24-224 of SEQ ID NO:1) or LILRB2 (residues 24-223 of SEQ ID NO:3) or variants thereof; PirB/LILRB2 polypeptide comprising the first three Ig-like domains of PirB (residues 24-322 of SEQ ID NO:1) or LILRB2 (residues 24-323 of SEQ ID NO:3) or variants thereof; PirB/LILRB2 polypeptide comprising the first four Ig-like domains of PirB (residues 24-422 of SEQ ID NO:1) or LILRB2 (residues 24-458 of SEQ ID NO:3) or variants thereof; PirB/LILRB2 polypeptide comprising the complete extracellular domain of PirB or LILRB2, for example a PirB/LILRB extracellular domain (ECD) polypeptide (SEQ ID NO 5, SEQ ID NO:6) or variants thereof, where an ECD polypeptide includes a polypeptide that does not include the PirB/LILRB2 transmembrane region or cytoplasmic domain, or a full-length PirB/LILRB polypeptide (SEQ ID NO:1, SEQ ID NO:3) or variant thereof.

In some instances, the polypeptide consists essentially of the ECD of PirB or LILRB2. In some instances, the polypeptide consists essentially of the first four Ig-like domains of PirB or LILRB2 or variants thereof. In some instances, the polypeptides consist essentially of the first three Ig-like domains of PirB or LILRB2 or variants thereof. In some instances, the polypeptides consist essentially of the first two Ig-like domains of PirB or LILRB2 or variants thereof.

By "comprising" it is meant that the recited elements are required in the composition, method, or kit, but other elements may be included to form the composition/method/kit etc. within the scope of the claim. For example, a polypeptide that comprises PirB/LILRB2 amino acid sequence corresponding to, e.g. residues 24-223 of SEQ ID NO:3 or, e.g., residues 24-458 of SEQ ID NO:3, may comprise LILRB2 amino acid sequence in addition to that sequence with the exception of any sequence recited by negative provisos. By "consisting essentially of", it is meant a limitation of the scope of composition or method described to the specified materials or steps that do not materially affect the basic and novel characteristic(s) of the subject invention. For example, a PirB/LILRB2 polypeptide "consisting essentially of" a disclosed sequence has the amino acid sequence of the disclosed sequence plus or minus about 5 amino acid residues at the boundaries of the sequence based upon the full length parent PirB/LILRB2 sequence from which it was derived, e.g. about 5 residues, 4 residues, 3 residues, 2 residues or about 1 residue less than the recited bounding amino acid residue, or about 1 residue, 2 residues, 3 residues, 4 residues, or 5 residues more than the recited bounding amino acid residue. By "consisting of", it is meant the exclusion from the composition, method, or kit of any element, step, or ingredient not specified in the claim. For example, a PirB/LILRB2 polypeptide "consisting of" a disclosed sequence consists only of the disclosed amino acid sequence. Compositions comprising a polypeptide "comprising", "consisting essentially of", or "consisting of" a disclosed PirB/LILRB2 sequence may comprise other elements in addition to the PirB/LILRB2 polypeptide(s), e.g. functional moieties such as polypeptides, small molecules, or nucleic acids bound, e.g. covalently bound, to the PirB/LILRB2 polypeptide; agents that promote the dimerization of the PirB/LILRB2 polypeptide; agents that promote the stability of the PirB/LILRB2 composition; agents that promote the solubility of the PirB/LILRB2 composition; adjuvants, etc. as will be readily understood in the art, with the exception of elements that are encompassed by any negative provisos.

Additional agents that inhibit binding of Aβ oligomers to PirB/LILRB2 may be readily identified using well-known techniques in the art or as described below for quantitatively or qualitatively detecting changes in Aβ—PirB/LILRB2 binding, for example, surface plasmon resonance (SPR), immunoprecipitation of PirB/LILRB2 and detection of Aβ oligomers by western blotting, etc.

Also included as non-limiting examples of agents that inhibit Aβ oligomer-induced PirB/LILRB2 signaling are those agents that suppress Aβ-induced PirB/LILRB2 activity, e.g. PirB activation/deactivation of downstream proteins (that is, proteins that are either directly or indirectly regulated by PirB/LILRB2 activity), and the activity of these downstream proteins. For example, Aβ oligomer-activated PirB/LILRB2 is shown herein to interact with cofilin and the Ser/Thr phosphatases PP2A, PP2B, and PP2C. By antagonizing Aβ-induced PirB/LILRB2 activity it is meant reducing Aβ oligomer-induced activation by PirB/LILRB2 of downstream proteins by 20% or more, for example by 30% or more, by 40% or more, or by 50% or more, in some instances, by 60% or more, by 70% or more, by 80% or more, e.g. by 90% or more, by 95% or more, or by 100%, i.e. to negligible amounts. Any convenient agent that inhibits PirB/LILRB2 activity in the presence of Aβ oligomers may be used, for example, PirB/LILRB2 intracellular peptides, e.g. residues 664-841 of NP_035225 (PirB) or residues 483-598 of NP_005865 (LILRB2) or fragments thereof; nucleic acids encoding residues 664-841 of NP_035225 (PirB) or residues 483-598 of NP_005865 (LILRB2) or fragments thereof; small molecules that interfere with binding of PirB/LILRB2 to cofilin and/or dephosphorylation of cofilin by PirB/LILRB2, PP2A, PP2B or PP2C, etc. Agents may be readily identified using any convenient technique for quantitatively or qualitatively detecting changes in PirB/LILRB2 signaling, for example, detecting the phosphorylation state of cofilin by Western blotting, flow cytometry or immunostaining; detecting the interaction of PirB/LILRB2 with cofilin, PP2A, PP2B, or PP2C by immunoprecipitation and Western blotting; assaying actin disassembly by immunohistochemistry, etc.

As indicated above, agents suitable for inhibiting Aβ oligomer-induced PirB/LILRB2 signaling in the subject compositions also include small molecule compounds. Naturally occurring or synthetic small molecule compounds of interest include numerous chemical classes, such as organic molecules, e.g., small organic compounds having a molecular weight of more than 50 and less than about 2,500 daltons. Candidate agents comprise functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Exemplary of pharmaceutical agents suitable for this invention are those described in, "The Pharmacological Basis of Therapeutics," Goodman and Gilman, McGraw-Hill, New York, N.Y., (1996), Ninth edition. Also included are toxins, and biological and chemical warfare agents, for example see Somani, S. M. (Ed.), "Chemical Warfare Agents," Academic Press, New York, 1992). Small molecule compounds can be provided directly to the medium in which the cells are being cultured, for example as a solution in DMSO or other solvent.

Agents suitable for inhibiting Aβ oligomer-induced PirB/LILRB2 signaling in the subject compositions also include polypeptides, for example, polypeptides that bind Aβ oligomers, e.g., PirB/LILRB2 polypeptides comprising the first two Ig-like domains of PirB (residues 24-224 of NP_035225) or LILRB2 (residues 24-223 of NP_005865) or variants thereof, polypeptides comprising the first three Ig-like domains of PirB or LILRB2 (residues 24-323 of NP_005865) or variants thereof, polypeptides comprising the first four Ig-like domains of PirB (residues 24-422 of NP_035225) or LILRB2 (residues 24-458 of NP_005865) or variants thereof, or polypeptides comprising the complete extracellular domain of PirB or LILRB2 and variants thereof. By an ECD polypeptide it is meant a polypeptide that does not include the transmembrane region or cytoplasmic domain. In some instances, the polypeptide consists essentially of the ECD of PirB or LILRB2. In some instances, the polypeptide consists essentially of the first four Ig-like domains of PirB or LILRB2 or variants thereof. In some instances, the polypeptides consist essentially of the first three Ig-like domains of PirB or LILRB2 or variants thereof. In some instances, the polypeptides consist essentially of the first two Ig-like domains of PirB or LILRB2 or variants thereof. Another example of polypeptides of interest as subject agents are PirB/LILRB2 polypeptides that bind cofilin or PP2, e.g. residues 664-841 of NP_035225 (PirB) or residues 483-598 of NP_005865 (LILRB2) or fragments thereof.

In some instances, the PirB/LILRB2 polypeptide or fragment thereof, e.g. as described above, is fused to an Fc domain, e.g. IgG (IgG1, IgG2, IgG3, IgG4), IgD, IgE. In other words, the subject agent is a polypeptide comprising, consisting essentially of, or consisting of a PirB/LILRB2 polypeptide or fragment thereof fused to an Fc domain, e.g human IgG1, IgG2, IgG3, IgG4. In some instances, e.g. when the Fc domain comprises a hinge region, the Fc domain promotes dimerization. In other instances, e.g. when the hinge region of the Fc domain is absent, the Fc domain does not promote dimerization.

Polypeptides for use as agents in the subject compositions may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like.

The polypeptide may be formulated for improved stability. For example, the peptides may be PEGylated, where the polyethyleneoxy group provides for enhanced lifetime in the blood stream. The polypeptide may be fused to another polypeptide to provide for added functionality, e.g. to increase the in vivo stability. Generally such fusion partners are a stable plasma protein, which may, for example, extend the in vivo plasma half-life of the polypeptide, e.g. greater than about 20 hours, when present as a fusion, in particular wherein such a stable plasma protein is an immunoglobulin constant domain. In most cases where the stable plasma protein is normally found in a multimeric form, e.g., immunoglobulins or lipoproteins, in which the same or different polypeptide chains are normally disulfide and/or noncovalently bound to form an assembled multichain polypeptide, the fusions herein containing the polypeptide also will be produced and employed as a multimer having substantially the same structure as the stable plasma protein precursor. These multimers will be homogeneous with respect to the polypeptide agent they comprise, or they may contain more than one polypeptide agent.

The polypeptide agent typically is fused to the plasma protein, e.g. IgG at the N-terminus of the plasma protein or fragment thereof which is capable of conferring an extended half-life upon the polypeptide. Increases of greater than about 100% on the plasma half-life of the polypeptide are satisfactory. Ordinarily, the polypeptide is fused C-terminally to the N-terminus of the constant region of immunoglobulins in place of the variable region(s) thereof, however N-terminal fusions may also find use. Typically, such fusions retain at least functionally active hinge, CH2 and CH3 domains of the constant region of an immunoglobulin heavy chain, which heavy chains may include IgG1, IgG2a, IgG2b, IgG3, IgG4, IgA, IgM, IgE, and IgD, usually one or a combination of proteins in the IgG class. Fusions are also made to the C-terminus of the Fc portion of a constant domain, or immediately N-terminal to the CH1 of the heavy chain or the corresponding region of the light chain. This ordinarily is accomplished by constructing the appropriate DNA sequence and expressing it in recombinant cell culture. Alternatively, the polypeptides may be synthesized according to known methods.

The site at which the fusion is made may be selected in order to optimize the biological activity, secretion or binding characteristics of the polypeptide. The optimal site will be determined by routine experimentation.

In some embodiments the hybrid immunoglobulins are assembled as monomers, or hetero- or homo-multimers, and particularly as dimers or tetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of basic four-chain units held together by disulfide bonds. IgA immunoglobulin, and occasionally IgG immunoglobulin, may also exist in a multimeric form in serum. In the case of multimers, each four chain unit may be the same or different.

The polypeptide agent for use in the subject compositions may be produced from eukaryotic produced by prokaryotic cells, it may be further processed by unfolding, e.g. heat denaturation, DTT reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

The subject polypeptides may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Another example of polypeptide agents suitable for inhibiting Aβ oligomer-induced PirB/LILRB2 signaling are antibodies, e.g. PirB-specific antibodies that bind to the extracellular domain of PirB, e.g. the PirB specific antibody disclosed in US Publication No. 2009/0285803, the disclosure of which is incorporated herein by reference. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. The specific or selective fit of a given structure and its specific epitope is sometimes referred to as a "lock and key" fit. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammal, chicken, other avians, etc., are considered to be "antibodies." The term "antibody" herein is used in the broadest sense and specifically covers intact antibodies, monoclonal antibodies, polyclonal antibodies, multispecific antibodies (e.g. bispecific antibodies) formed from at least two intact antibodies, and antibody fragments, so long as they exhibit the desired biological activity. Antibodies are typically provided in the media in which the cells are cultured.

Agents suitable for inhibiting Aβ oligomer-induced PirB/LILRB2 signaling in the subject compositions also include nucleic acids, for example, nucleic acids that encode siRNA, shRNA or antisense molecules of PirB or LILRB2, or nucleic acids that encode polypeptides, e.g. PirB/LILRB2 polypeptides comprising or consisting essentially of PirB/LILRB2 extracellular domain sequences that bind Aβ oligomers, e.g. PirB/LILRB2 cytoplasmic tail sequences that bind cofilin or Ser/Thr phosphatases, PP2A, PP2B or PP2C, e.g. nucleic acids encoding residues 664-841 of NP_035225 (PirB) or residues 483-598 of NP_005865 (LILRB2) or fragments thereof. Many vectors useful for transferring nucleic acids into target cells are available. The vectors may be maintained episomally, e.g. as plasmids, minicircle DNAs, virus-derived vectors such cytomegalovirus, adenovirus, etc., or they may be integrated into the target cell genome, through homologous recombination or random integration, e.g. retrovirus derived vectors such as MMLV, HIV-1, ALV, etc.

Nucleic acid may be provided directly to cells. In other words, the cells, e.g. neurons, are contacted with vectors comprising the nucleic acid of interest such that the vectors are taken up by the cells. Methods for contacting cells with nucleic acid vectors, such as electroporation, calcium chloride transfection, and lipofection, are well known in the art.

Alternatively, the nucleic acid of interest may be provided to the subject cells via a virus. In other words, the cells are contacted with viral particles comprising the nucleic acid of interest. Retroviruses, for example, lentiviruses, are particularly suitable to the method of the invention. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein to be incorporated into the capsid, this envelope protein determining the specificity of the viral particle for the cells. Envelope proteins are of at least three types, ecotropic, amphotropic and xenotropic. Retroviruses packaged with ecotropic envelope protein, e.g. MMLV, are capable of infecting most murine and rat cell types, and are generated by using ecotropic packaging cell lines such as BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse, and are generated by using amphotropic packaging cell lines such as PA12 (Miller et al. (1985) Mol. Cell. Biol. 5:431-437); PA317 (Miller et al. (1986) Mol. Cell. Biol. 6:2895-2902); GRIP (Danos et al. (1988) PNAS 85:6460-6464). Retroviruses packaged with xenotropic envelope protein, e.g. AKR env, are capable of infecting most mammalian cell types, except murine cells. The appropriate packaging cell line may be used to ensure that the subject CD33+ differentiated somatic cells are targeted by the packaged viral particles. Methods of introducing the retroviral vectors comprising the subject nucleic acid agent into packaging cell lines and of collecting the viral particles that are generated by the packaging lines are well known in the art.

Vectors used for providing nucleic acid of interest to cells will typically comprise suitable promoters for driving the expression, that is, transcriptional activation, of the nucleic acid of interest. In other words, the nucleic acid of interest will be operably linked to a promoter. This may include ubiquitously acting promoters, for example, the CMV-β-actin promoter, or inducible promoters, such as promoters that are active in particular cell populations or that respond to the presence of drugs such as tetracycline. By transcriptional activation, it is intended that transcription will be increased above basal levels in the target cell by at least about 10 fold, by at least about 100 fold, more usually by at least about 1000 fold. In addition, vectors used for providing the subject agent to cells may include nucleic acid sequences that encode for selectable markers in the target cells, so as to identify cells that have taken up the subject agent.

Agents may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

For inclusion in a medicament, the subject agent may be obtained from a suitable commercial source. As a general proposition, the total pharmaceutically effective amount of the subject agent administered parenterally per dose will be in a range that can be measured by a dose response curve.

Preparations of subject agent to be used for therapeutic administration must be sterile. Sterility is readily accomplished by filtration through sterile filtration membranes (e.g., 0.2 μm membranes). Therapeutic compositions generally are placed into a container having a sterile access port, for example, an intravenous solution bag or vial having a stopper pierceable by a hypodermic injection needle. The subject agent-based therapies may be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 1% (w/v) aqueous solution of compound, and the resulting mixture is lyophilized. The infusion solution is prepared by reconstituting the lyophilized compound using bacteriostatic Water-for-Injection.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringers solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The nucleic acids or polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

The subject agent can be incorporated into a variety of formulations. More particularly, the subject agent of the present invention can be formulated into pharmaceutical compositions by combination with appropriate pharmaceutically acceptable carriers or diluents.

Pharmaceutical preparations are compositions that include one or more targeted subject agents present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal. Such pharmaceutical vehicles can be lipids, e.g. liposomes, e.g. liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used. Pharmaceutical compositions may be formulated into preparations in solid, semi-solid, liquid or gaseous forms, such as tablets, capsules, powders, granules, ointments, solutions, suppositories, injections, inhalants, gels, microspheres, and aerosols. As such, administration of the subject agent can be achieved in various ways, including oral, buccal, rectal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation. The active agent may be formulated for immediate activity or it may be formulated for sustained release.

For some conditions, particularly central nervous system conditions, it may be necessary to formulate agents to cross the blood-brain barrier (BBB). One strategy for drug delivery through the blood-brain barrier (BBB) entails disruption of the BBB, either by osmotic means such as mannitol or leukotrienes, or biochemically by the use of vasoactive substances such as bradykinin. The potential for using BBB opening to target specific agents to brain tumors is also an option. A BBB disrupting agent can be co-administered with the therapeutic compositions of the invention when the compositions are administered by intravascular injection. Other strategies to go through the BBB may entail the use of endogenous transport systems, including Caveolin-1 mediated transcytosis, carrier-mediated transporters such as glucose and amino acid carriers, receptor-mediated transcytosis for insulin or transferrin, and active efflux transporters such as p-glycoprotein. Active transport moieties may also be conjugated to the therapeutic compounds for use in the invention to facilitate transport across the endothelial wall of the blood vessel. Alternatively, drug delivery of therapeutics agents behind the BBB may be by local delivery, for example by intrathecal delivery, e.g. through an Ommaya reservoir (see e.g. U.S. Pat. Nos. 5,222,982 and 5,385,582, incorporated herein by reference); by bolus injection, e.g. by a syringe, e.g. intravitreally or intracranially; by continuous infusion, e.g. by cannulation, e.g. with convection (see e.g. US Application No. 20070254842, incorporated here by reference); or by implanting a device upon which the agent has been reversably affixed (see e.g. US Application Nos. 20080081064 and 20090196903, incorporated herein by reference).

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred.

The data obtained from cell culture and/or animal studies can be used in formulating a range of dosages for humans. The dosage of the active ingredient typically lines within a range of circulating concentrations that include the ED50 with low toxicity. The dosage can vary within this range depending upon the dosage form employed and the route of administration utilized.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The effective amount of a therapeutic composition to be given to a particular patient will depend on a variety of factors, several of which will differ from patient to patient. A competent clinician will be able to determine an effective amount of a therapeutic agent to administer to a patient to halt or reverse the progression the disease condition as required. Utilizing LD50 animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

Methods

Also provided are methods for reducing the effects of amyloid beta (Aβ) oligomers on a cell, which find many uses in medicine and research, for example in reducing cognitive decline or visual decline in an individual suffering from Aβ-associated disease or disorder, and for screening candidate agents to identify new therapeutics that interfere with the toxic effects of Aβ in individuals with Aβ-associated diseases and disorders.

Cells of interest that may be protected from the effects of Aβ oliogomers using the subject compositions include cells that express PirB/LILRB2, e.g. PirB or LILRB2-positive cells. By a "PirB/LILRB2-expressing cell" it is meant a cell that transcribes and translates the PirB or LILRB2 gene. In other words, the cell is positive for PirB/LILRB2 expression. A cell may be readily identified as PirB/LILRB2 positive by detecting the expression of LilrB2. Should it be useful to detect PirB/LILRB on the surface of a cell, any convenient technique for detecting LilrB2 on the surface of a cell may be employed, for example, immunohistochemistry, flow cytometry, ELISA, Western blotting, in situ hybridization, etc. Examples of PirB/LILRB2 positive cells include neurons, e.g. retinal ganglion cells and projection neurons of the cerebral cortex, and microglia.

Cells of interest that may be protected from the effects of Aβ oliogomers using the subject compositions also include cells that do not express PirB/LILRB2, i.e. PirB/LILRB2-negative cells. For example, as discussed above, it is envisioned that the subject compositions, e.g. PirB/LILRB2 polypeptide mimetics, e.g. PirB/LILRB2 polypeptides and variants thereof as described elsewhere herein, may be administered to prevent Aβ oligomers from binding to other Aβ receptors, e.g. the NMDA receptor (Snyder et al. (2005) Nat Neurosci. 8(8):1051-8), cellular prion protein (Laurén J, et al. (2009) Nature 457(7233):1128-32), the receptor tyrosine kinase EphB2 (Cissé M, et al. (2011) Nature 469(7328): 47-52), the receptor for advanced glycation end products ("RAGE", Origlia N, et al. (2008) J Neurosci. 28(13):3521-30), metabotropic glutamate receptor 5 (Um J W, et al. (2013) Neuron 79(5):887-902), and the immune cell receptor FcγRIIb (Kam T, et al. J Clin Invest. 2013 Jun. 10), e.g. by binding to Aβ oligomers and hindering the binding of Aβ to other (i.e. non-PirB/LILRB2) Aβ receptors on the cell. Such cells may be readily identified by one of ordinary skill in the art, for example by using techniques in the art for detecting the expression of one or more of these other receptors, and/or for detecting the binding of Aβ oligomers to a cell.

In practicing the subject methods of the application, cells, i.e. in vivo or in vitro, are contacted with an effective amount of the agent to inhibit the effects of Aβ oligomers on cells and to the individual. Biochemically speaking, an "effective amount" or "effective dose" of an agent that inhibits the effects of Aβ oligomers on cells is an amount of agent that will inhibit, antagonize, decrease, reduce, or suppress by about 20% or more, e.g. by 30% or more, by 40% or more, or by 50% or more, in some instances by 60% or more, by 70% or more, by 80% or more, or by 90% or more, in some cases by about 100%, i.e. to negligible amounts, and in some instances reverse, the effects of Aβ oligomers on a cell. For example, an "effective amount" or "effective dose" of an agent that inhibits the effects of Aβ oligomers on cells is an amount of agent that will inhibit, antagonize, decrease, reduce, or suppress by about 20% or more, e.g. by 30% or more, by 40% or more, or by 50% or more, in some instances by 60% or more, by 70% or more, by 80% or more, or by 90% or more, in some cases by about 100%, i.e. to negligible amounts, the amount of cell death induced by Aβ oligomers. Methods for measuring cell viability and cell death are well known in the art, any of which may be used to determine an effective dose.

As another example, and "effective amount" or "effective dose" of an agent that inhibits the effects of Aβ oligomers on neurons is an amount of agent that will inhibit, antagonize, decrease, reduce, or suppress by about 20% or more, e.g. by 30% or more, by 40% or more, or by 50% or more, in some instances by 60% or more, by 70% or more, by 80% or more, or by 90% or more, in some cases by about 100%, i.e. to negligible amounts, the reduction in synaptic plasticity and loss of synapses that occurs in the presence of Aβ oligomers. In other words, cells contacted with an effective amount of the agent will become more responsive to cues, e.g. activity cues, which promote the formation and maintenance of synapses.

Methods for measuring synaptic plasticity in individuals are well known in the art, any of which may be used to determine an effective dose. These include, for example, observing the induction of LTP in neural circuits in awake individuals, e.g. by performing non-invasive stimulation techniques on awake individuals to induce LTP-like long-lasting changes in localized neural activity (Cooke S F, Bliss T V (2006) Plasticity in the human central nervous system. Brain. 129(Pt 7):1659-73); mapping plasticity and increased neural circuit activity in individuals, e.g. by using positron emission tomography, functional magnetic resonance imaging, and/or transcranial magnetic stimulation (Cramer and Bastings (2000) Mapping clinically relevant plasticity after stroke. Neuropharmacology. 39(5):842-51); and by detecting neural plasticity following learning, i.e. improvements in memory, e.g. by assaying retrieval-related brain activity (Buchmann A, et al. (2008) Prion protein M129V polymorphism affects retrieval-related brain activity. Neuropsychologia. 46(9):2389-402) or, e.g., by imaging brain tissue by functional magnetic resonance imaging (fMRI) following repetition priming with familiar and unfamiliar objects (Soldan A, et al. (2008) Global familiarity of visual stimuli affects repetition-related neural plasticity but not repetition priming. Neuroimage. 39(1):515-26; Soldan A, et al. (2008) Aging does not affect brain patterns of repetition effects associated with perceptual priming of novel objects. J Cogn Neurosci. 20(10):1762-76). In some aspects of the subject methods, the method further comprises the step of measuring one or more of these effects.

In a clinical sense, an effective amount, or dose, of an agent that inhibits the toxic effects of Aβ oligomers on cells is an amount of agent that, when administered for a suitable period of time, usually at least about one week, and maybe about two weeks, or more, up to a period of about 4 weeks, 8 weeks, or longer will evidence an alteration in the symptoms associated with reduced synaptic plasticity and synapse loss in an Aβ-associated disease, for example, cognitive impairment in an individual with Alzheimer's Disease, CAA, or Down syndrome relative to a healthy individual, visual impairment in an individual with glaucoma relative to a healthy individual, etc. For example, an effective dose is the dose that when administered for a suitable period of time, usually at least about one week, and maybe about two weeks, or more, up to a period of about 4 weeks, 8 weeks, or longer will slow e.g. by about 20% or more, e.g. by 30% or more, by 40% or more, or by 50% or more, in some instances by 60% or more, by 70% or more, by 80% or more, or by 90% or more, or halt cognitive decline, i.e. stabilize the cognitive abilities, in a patient suffering from Alzheimer's disease, CAA, or Down syndrome or halt visual decline, i.e. stabilize the visual abilities, in a patient suffering from glaucoma. In some embodiments, an effective amount or dose may not only slow or halt the progression of the disease condition but may also induce the reversal of the condition. For example, an effective dose is the dose that when administered for a suitable period of time, usually at least about one week, and maybe about two weeks, or more, up to a period of about 4 weeks, 8 weeks, or longer will improve the cognition in an individual with Alzheimer's Disease, CAA, or Down syndrome, or vision in an individual with glaucoma, by, for example 1.5-fold, 2-fold, 3-fold, 4-fold, 5-fold, in some instances 6-fold, 7-fold, 8-fold, 9-fold, or 10-fold or more. It will be understood by those of skill in the art that an initial dose may be administered for such periods of time, followed by maintenance doses, which, in some cases, will be at a reduced dosage.

Methods for measuring cognition or vision are also well known in the art, any of which may be used to determine an effective dose Examples include tests such as cognition tests and IQ test for measuring cognitive ability, e.g. attention and concentration, the ability to learn complex tasks and concepts, memory, information processing, visuospatial function, the ability to produce and understanding language, the ability to solve problems and make decisions, and the ability to perform executive functions; for example, the General Practitioner Assessment of Cognition (GPCOG) test, the Memory Impairment Screen, the Mini Mental State Examination (MMSE), the California Verbal Learning Test, Second Edition, Short Form, for memory, the Delis-Kaplan Executive Functioning System test, and the like. Examples of vision tests include, for example, visual acuity tests, fundoscopy, and the like.

The calculation of the effective amount or effective dose of agent to be administered is within the skill of one of ordinary skill in the art, and will be routine to those persons skilled in the art. Needless to say, the final amount to be administered will be dependent upon the route of administration and upon the nature of the disorder or condition that is to be treated.

The subject methods and compositions find use in reducing the effects of Aβ oligomers on cells both in vitro and in vivo. For example, and as described in greater detail in the Utility section below, the subject methods and compositions may be used in research, e.g. in in vitro screens to identify new therapies for the treatment of Aβ-associated diseases, e.g. Aβ-associated diseases of the central nervous system. As another example, the subject methods and compositions may be used in vivo for the treatment of Aβ-associated diseases and disorders, e.g. Alzheimer's Disease, CAA, Down's syndrome, and glaucoma.

Cells may be from any mammalian species, e.g. murine, rodent, canine, feline, equine, bovine, ovine, primate, human, etc. For in vitro studies, cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro.

If the cells are primary cells, they may be harvest from an individual by any convenient method. For example, cells, e.g. blood cells, e.g. leukocytes, may be harvested by apheresis, leukocytapheresis, density gradient separation, etc. As another example, cells from solid tissues, e.g. neurons, may be harvested by biopsy. An appropriate solution may be used for dispersion or suspension of the harvested cells. Such solution will generally be a balanced salt solution, e.g. normal saline, PBS, Hank's balanced salt solution, Iscoves, etc., conveniently supplemented with fetal calf serum and/or other factors, e.g. B27, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

In practicing the subject methods, the subject composition may be provided to the cells one or more times, e.g. one time, twice, three times, or more than three times, and the cells allowed to incubate with the subject agent for some amount of time following each contacting event e.g. 16-24 hours, after which time the media is replaced with fresh media and the cells are cultured further.

In cases in which two or more different subject agents are provided to the cell, i.e. a cocktail of agents, the agents may be provided simultaneously, e.g. as two polypeptides delivered simultaneously, as two nucleic acid vectors delivered simultaneously, or as a single nucleic acid vector comprising the coding sequences for both fusion polypeptides. Alternatively, they may be provided consecutively, e.g. the first subject agent being provided first, followed by the second subject agent, etc. or vice versa.

Contacting the cells with the subject agent in vitro may occur in any culture media and under any culture conditions that promote the survival of the cells. For example, cells may be suspended in any appropriate nutrient medium that is convenient, such as Iscove's modified DMEM or RPMI 1640, supplemented with serum, e.g. fetal calf serum, heat inactivated goat serum (about 5-10%) etc., or synthetic reagents that support growth, e.g. B27, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. Examples of mediums and reagents that find particular use in the culturing of neurons may be found in the Example section below.

As discussed above, the subject methods and compositions find use in reducing the effects of Aβ oligomers on cells in vivo as well. In these in vivo embodiments, the subject agent is administered directly to the individual. Any mammal may be administered with the subject agent to reduce the effects of Aβ oligomers, e.g. murine, rodent, canine, feline, equine, bovine, ovine, primate, human, etc. The subject agent may be administered by any of a number of well-known methods for the administration of polypeptides, peptides, small molecules or nucleic acids to a subject, e.g. as described herein or known in the art.

In some embodiments, the composition may be provided in conjunction with a second agent that modulates synapse maintenance and/or synaptic plasticity. In other words, an agent that reduces synapse loss or loss of synaptic plasticity, or that promotes synapse formation and/or promotes synaptic plasticity, may be provided in combination with the presently described agent that inhibits the effects of Aβ oligomers on cells. Any convenient second agent that modulates synapse maintenance and/or synaptic plasticity may be employed. For example, the agent may inhibit the activation of the complement pathway. Complement is a system of plasma proteins that interacts with the cell surfaces of pathogens or cells to mark them for destruction by phagocytes. The complement pathway has been implicated in promoting synapse loss and cognitive or visual decline in diseases such as Alzheimer's Disease and glaucoma, as well as in the cognitive decline associated with aging. Examples of therapeutic agents that inhibit complement signaling are provided in, for example, U.S. application Ser. No. 13/586,556, the full disclosure of which is incorporated herein by reference.

In some embodiments, the composition may be provided in conjunction with a second agent that has been demonstrated in the art to modulate Aβ oligomer effects on a cell. For example, an agent that reduces the amount of Aβ peptide produced, or that reduces the aggregation of Aβ peptides into oligomers, or that promotes the clearance of Aβ oligomers from the CNS, may be provided in combination with the presently described agent that inhibits the effects of Aβ oligomers on cells. Examples of such agents include β-secretase inhibitors, which block the first cleavage of APP outside of the cell; γ-Secretase inhibitors (e. g. semagacestat), which block the second cleavage of APP in the cell membrane to stop the subsequent formation of Aβ and its toxic fragments; selective Aβ42 lowering agents (e. g. tarenflurbil), which modulate γ-secretase to reduce Aβ42 production in favor of other (shorter) Aβ versions; immunotherapeutics which stimulate the host immune system to recognize and attack Aβ; and antibodies that either prevent plaque deposition or enhance clearance of plaques or Aβ oligomers. One such beta-amyloid vaccine that is currently in clinical trials is CAD106; and anti-aggregation agents such as apomorphine, which prevent Aβ fragments from aggregating or clear aggregates once they are formed.

In some embodiments, the composition may be provided in conjunction with a second agent that has been demonstrated in the art to treat a neurodegenerative disease or cognitive impairment. For example, a number of agents have been shown to have some efficacy in treating the cognitive symptoms of Alzheimer's disease (e.g., memory loss, confusion, and problems with thinking and reasoning), e.g. cholinesterase inhibitors (e.g. Donepezil, Rivastigmine, Galantamine, Tacrine), Memantine, and Vitamin E. As another example, a number of agents have been shown to have some efficacy in treating behavioral or psychiatric symptoms of Alzheimer's Disease, e.g. citalopram (Celexa), fluoxetine (Prozac), paroxeine (Paxil), sertraline (Zoloft), trazodone (Desyrel), lorazepam (Ativan), oxazepam (Serax), aripiprazole (Abilify), clozapine (Clozaril), haloperidol (Haldol), olanzapine (Zyprexa), quetiapine (Seroquel), risperidone (Risperdal), and ziprasidone (Geodon).

In some embodiments, the subject composition is provided before the second agent. In some embodiments, the subject composition is provided after the second agent. In some embodiments, the subject composition is provided concurrently with the second agent. In certain such embodiments, the subject composition comprises one or more of these additional agents.

In some aspects of the subject methods, the method further comprises the step of identify an individual in need of treatment by the subject methods, e.g diagnosing an individual as having a cognitive or visual impairment, diagnosing an individual as having an Aβ-associated disease or disorder, etc. Methods for measuring cognitive or visual function and identifying an individual having a cognitive or visual impairment are well known in the art, any of which may be used to identify an individual in need of treatment by the subject methods. For example, measuring a cognitive impairment may include administering a standardized learning task or IQ test, and comparing the results of the task/test with a reference, e.g. the results of the test at an earlier time in the individual's life, or the results of the test from a healthy, i.e. non-affected, individual. Cognition tests and IQ test for measuring cognitive ability and cognitive impairment, e.g. attention and concentration, the ability to learn complex tasks and concepts, memory, information processing, visuospatial function, the ability to produce and understanding language, the ability to solve problems and make decisions, and the ability to perform executive functions, are well known in the art, and include, for example, the General Practitioner Assessment of Cognition (GPCOG) test, the Memory Impairment Screen, the Mini Mental State Examination (MMSE), the California Verbal Learning Test, Second Edition, Short Form, for memory, the Delis-Kaplan Executive Functioning System test, and the like. As another example, measuring a visual impairment may include administering a visual acuity test, and comparing the results of the test with a reference, e.g. the results of the test at an earlier time in the individual's life, or the results of the test from a healthy, i.e. non-affected, individual.

In some aspects of the subject methods, the method further comprises the step of measuring cognitive ability, vision, synaptic plasticity, etc. after treatment, e.g. using the methods described herein or known in the art; and detecting a decreased rate of cognitive decline/visual decline/loss of synaptic plasticity, a stabilization of cognitive ability/visual ability/synaptic plasticity, and/or an increase in cognitive ability/visual ability/synaptic plasticity after administration of the subject compositions as compared to the cognitive ability/visual ability/synaptic plasticity of the individual before the subject composition was administered. In some instances, the determination is made by comparing the results of the cognition test, vision test or synaptic plasticity test to the results of the test performed on the same individual at an earlier time, e.g. 1 week earlier, 2 weeks earlier, 1 month earlier, 2 months earlier, 3 months earlier, 6 months earlier, 9 months earlier, 1 year earlier, 2 years earlier, 5 years earlier, or 10 years earlier, or more. In other instances, the determination is made by comparing the results of the cognition test, vision test, or synaptic plasticity test to the results of the test performed on a reference individual, e.g. a healthy individual that does not suffer from any greater cognitive or visual impairment than that associated with the natural aging process (a negative control), or, e.g. an individual that does suffer from Aβ-associated cognitive impairment.

Utility

The subject methods and compositions find a number of uses in research and medicine. For example, the subject methods and compositions may be used to treat, treat, i.e. slow, halt, and in some instance reverse, the cognitive or visual decline that is a symptom of Aβ-associated diseases and disorders of the nervous system, e.g. the central nervous system, and in improving cognition and vision in Aβ-associated CNS disorders associated with impaired cognitive or visual function.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease. The terms "individual," "subject," "host," and "patient," used interchangeably herein, refer to a mammal, including, but not limited to, murines, simians, humans, mammalian farm animals, mammalian sport animals, and mammalian pets.

By "cognition" it is meant the mental processes that include attention and concentration, learning complex tasks and concepts, memory (acquiring, retaining, and retrieving new information in the short and/or long term), information processing (dealing with information gathered by the five senses), visuospatial function (visual perception, depth perception, using mental imagery, copying drawings, constructing objects or shapes), producing and understanding language, verbal fluency (word-finding), solving problems, making decisions, and executive functions (planning and prioritizing). Cognition is a faculty for the processing of information, applying knowledge, and changing preferences. By "cognitive plasticity" it is meant the ability to learn, e.g., the ability to learn complex tasks and concepts, analogous to the ability to learn of an organism that is undifferentiated such as a newborn or juvenile, e.g., a human from the time of birth to pre-pubertal age of about 10 years. By "cognitive decline", it is meant a progressive decrease in cognition, as evidenced by, for example, a decline in one or more of, e.g., attention and concentration, learning complex tasks and concepts, memory (acquiring, retaining, and retrieving new information in the short and/or long term), information processing (dealing with information gathered by the five senses), visuospatial function (visual perception, depth perception, using mental imagery, copying drawings, constructing objects or shapes), producing and understanding language, verbal fluency (word-finding), solving problems, making decisions, and executive functions (planning and prioritizing). By "an impairment in cognitive ability", "reduced cognitive function", and "cognitive impairment", it is meant a reduction in cognitive ability relative to a healthy individual, e.g. an age-matched healthy individual, or relative to the ability of the individual at an earlier point in time, e.g. 2 weeks, 1 month, 2 months, 3 months, 6 months, 1 year, 2 years, 5 years, or 10 years or more previously. By "Aβ-associated cognitive decline" and "Aβ-associated cognitive impairment," it is meant decline or impairment in cognitive ability that is typically associated with the accumulation of Aβ in the nervous system.

In some instances, treatment by methods of the present disclosure slows, or reduces, the progression of the Aβ-associated cognitive decline. In other words, cognitive abilities in the individual decline more slowly following treatment by the disclosed methods than prior to or in the absence of treatment by the disclosed methods. In some instances, treatment by methods of the present disclosure stabilizes the cognitive abilities of an individual. For example, the progression of cognitive decline in an individual suffering from Aβ-associated cognitive decline is halted following treatment by the disclosed methods. In other words, no (further) cognitive impairment is observed. In some instances, treatment by methods of the present disclosure reduces, or reverses, cognitive impairment, e.g. as observed by improving cognitive abilities in an individual suffering from Aβ-associated cognitive decline. In other words, the cognitive abilities of the individual suffering from Aβ-associated cognitive decline following treatment by the disclosed methods are better than prior to treatment by the disclosed methods, i.e. they improve upon treatment. In some instances, treatment by methods of the present disclosure abrogates cognitive impairment. In other words, the cognitive abilities of the individual suffering from Aβ-associated cognitive decline are restored, e.g. to a level observed of the individual when the individual was about 40 years old or less, following treatment by the disclosed methods, e.g. as evidenced by improved cognitive abilities in an individual suffering from the Aβ-associated cognitive decline.

Methods for measuring cognitive function are well known in the art, any of which may be used to identify an individual in need of treatment by the subject methods and/or to measure the cognitive stabilization or improvement in an individual during/after treatment with the subject methods. These include, for example, administering a standardized learning task or IQ test to the individual, and comparing the results of the task/test with a reference. In some instances, the reference may be the results of the task/test performed by one or more age-matched individuals that either experience reduced cognitive function (i.e. positive controls) or do not experience reduced cognitive function (i.e. negative controls). In some instances, the reference may be the results of the task/test performed by the same individual at an earlier age, e.g. 1 week earlier, 1 month earlier, 3 months earlier, 6 months earlier, 9 months earlier, and the like, for example to determine if the individual is suffering from cognitive decline.

By "vision" it is meant the ability to see objects. By "visual decline", it is meant a progressive decrease over time in the acuity of an individual's vision, i.e. the sharpness of vision. By "reduced vision" or "reduced visual function" it is meant an impairment in vision relative to a healthy individual, e.g. an age-matched healthy individual. Methods for measuring visual acuity and visual function are also well known in the art, any of which may be used to identify an individual in need of treatment by the subject methods and/or responsiveness of an individual to treatment by the subject methods. These include, for example, measuring the ability of the individual to discern letters or numbers at a given distance according to a fixed standard. In some instances, the reference may be the results of a visual acuity test performed by one or more age-matched individuals that either experience reduced visual function (i.e. positive controls) or do not experience reduced visual function (i.e. negative controls). In some instances, the reference may be the results of the task performed by the same individual at an earlier age, e.g. 1 week earlier, 1 month earlier, 3 months earlier, 6 months earlier, 9 months earlier, and the like, for example to determine if the individual is suffering from visual decline.

The subject methods and compositions find use in treating any Aβ-associated disease or disorder. For example, the subject methods and compositions find use in treating Alzheimer's Disease, and more particularly, the cognitive decline and impairment associated with Alzheimer's Disease. The term "Alzheimer's Disease" (AD) refers to a progressive mental deterioration manifested by memory loss, confusion and disorientation beginning in late middle life and typically resulting in death in five to ten years. Soluble Aβ oligomers have been implicated in causing Alzheimer's disease, and Aβ is the main component of amyloid plaque deposits found in the brains of patients with Alzheimer's Disease. Methods for diagnosing Alzheimer's Disease are well known in the art. For example, the National Institute of Neurological and Communicative Disorders and Stroke-Alzheimer's Disease and the Alzheimer's Disease and Related Disorders Association (NINCDS-ADRDA) criteria can be used to diagnose Alzheimer's Disease (McKhann et al., 1984, Neurology 34:939-944). The patient's cognitive function and responsiveness to treatment using the subject methods and compositions can be assessed by the Alzheimer's Disease Assessment Scale-cognitive subscale (ADAS-cog; Rosen et al., 1984, Am. J. Psychiatry 141: 1356-1364).

As another example, the subject methods and compositions also find use in treating cerebral amyloid angiopathy. Cerebral amyloid angiopathy (CAA), also known as congophilic angiopathy, is a form of angiopathy in which amyloid deposits form in the walls of the blood vessels of the central nervous system. The term congophilic is used because the presence of the abnormal aggregations of amyloid can be demonstrated by microscopic examination of brain tissue after application of a special stain called Congo red. The amyloid material is only found in the brain and as such the disease is not related to other forms of amyloidosis.

As a third example, the subject methods a compositions also find use in treating Down syndrome (DS), or Down's syndrome, and more particularly, the cognitive impairment and decline associated with Down's syndrome. Down syndrome is a genetic condition in which a person has 47 chromosomes instead of the usual 46. In most cases, also called "trisomy 21", the genetic condition is caused by the presence of all or part of a third copy of chromosome 21. Down syndrome is typically associated with a delay in cognitive ability (mental retardation, or MR, i.e. an IQ below 70) and physical growth, and a particular set of facial characteristics. The average IQ of young adults with Down syndrome is around 50, compared to children without the condition with an IQ of 100. A large proportion of individuals with Down syndrome have a severe degree of impaired cognitive disability. Aβ oligomer levels are elevated in Down syndrome patients throughout life (reviewed in Head and Lott (2004) Curr Opin Neurol 17(2):95-100), and the administration of a γ-secretase inhibitor to lower β-amyloid levels in young mice that model DS has been demonstrated to correct learning deficits in these mice (Netzer W J, et al. (2010) Lowering beta-amyloid levels rescues learning and memory in a Down syndrome mouse model. PLoS One 5:e10943). Methods for diagnosing Down syndrome are well known in the art, as are methods for measuring IQ and the improvement in IQ that may be observed following treatment with the subject methods and compositions.

As a fourth example, the subject methods a compositions also find use in treating glaucoma, and more particularly, the visual impairments associated with glaucoma. Glaucoma is an eye disease in which the optic nerve is damaged in a characteristic pattern. This can permanently damage vision in the affected eye(s) and lead to blindness if left untreated. Glaucoma has historically been associated with increased fluid pressure in the eye (aqueous humour). Recent evidence suggests that Aβ aggregates contribute to the development of at least some forms of glaucoma by promoting retinal ganglion cell (RGC) synapse loss and RGC apoptosis, and that targeting the Aβ pathway will provide a therapeutic avenue for glaucoma management (Guo et al. (2007) Targeting amyloid-beta in glaucoma treatment. Proc Natl Acad Sci USA. 104(33):13444-9; Ning et al. (2008) Amyloid-β Deposits Lead to Retinal Degeneration in a Mouse Model of Alzheimer Disease. Invest. Ophthalmol. Vis. Sci. 49(11): 5136-5143). The term 'ocular hypertension' is used for people with consistently raised intraocular pressure (IOP) without any associated optic nerve damage. Conversely, the term 'normal tension' or 'low tension' glaucoma is used for those with optic nerve damage and associated visual field loss, but normal or low IOP. Methods for diagnosing glaucoma are well known in the art, and include, for example, visual acuity tests for gradually progressive visual field loss, testing for intraocular pressure via tonometry, examination of the anterior chamber angle (the angle in the eye where the iris meets the cornea) by gonioscopy, and examination of the optic nerve by fundoscopic examination to observe visible damage or increases in the cup-to-disc ratio. The patient's visual decline and responsiveness to treatment using the subject methods and compositions can be assessed by assaying for a stabilization or improvement in scoring on visual acuity tests and stabilization of optic nerve loss by fundoscopy.

Screening Methods

The methods described above provide a useful system for screening candidate agents for the ability to inhibit Aβ-associated synapse loss, loss of synaptic plasticity, and the associated cognitive or visual decline. For example, screening for candidate agents that prevent Aβ-induced loss of synapses and loss of synaptic plasticity in neurons that express PirB/LILRB2 should identify agents that will be useful in protecting those neurons from the effects of Aβ oligomers in vivo, which, in turn, will reduce, halt or even reverse cognitive or visual decline and reduced cognitive or visual function in patients with Aβ-associated conditions relative to untreated patients.

For example, in screening assays for biologically active agents, cells expressing PirB or LILRB2 are contacted with Aβ oligomers and a candidate agent of interest, and the effect of the candidate agent on modulating synapse numbers and synaptic plasticity is assessed by monitoring one or more output parameters. Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values. Thus, for example, one such method may comprise contacting a cell that expresses PirB or LILRB2 with the Aβ oligomers and a candidate agent; and comparing the parameter to the parameter in a cell that expresses the PirB or LILRB2 and that was contacted with the Aβ oligomers but was not contacted with the candidate agent, wherein a difference in the parameter in the cell contacted with the candidate agent indicates that the candidate agent will reduce cell sensitivity to the Aβ oligomers.

One example of an output parameter that may be quantified when screening for, e.g., agents that modulate cellular sensitivity to Aβ oligomers would be to assess the neurons for their ability to undergo long term potentiation (LTP) or long term depression (LTD). Other examples would include assessing the number of dendritic spines, the amount of neurotransmitter transcribed and translated after a given amount of time exposed to agent, or the number of neurotransmitter vesicles present at the synapse. For example, for synapse quantification, cultures would be fixed, blocked and washed, then stained with antibodies specific synaptic proteins, e.g. synaptotagmin, PSD-95, etc. and visualized with an appropriate reagent, as known in the art. Analysis of the staining may be performed microscopically. In one embodiment, digital images of the fluorescence emission are with a camera and image capture software, adjusted to remove unused portions of the pixel value range and the used pixel values adjusted to utilize the entire pixel value range. Corresponding channel images may be merged to create a color (RGB) image containing the two single-channel images as individual color channels. Co-localized puncta can be identified using a rolling ball background subtraction algorithm to remove low-frequency background from each image channel. Number, mean area, mean minimum and maximum pixel intensities, and mean pixel intensities for all synaptotagmin, PSD-95, and colocalized puncta in the image are recorded and saved to disk for analysis. Yet other output parameters could include the activation state of the PirB/LILRB2 protein, e.g. the extent of phosphorylation observed on the ITIM domains of the PirB/LILRB2 cytoplasmic tail, the extent of cofilin activation, or the extent to which actin fibers become disassembled in the presence of Aβ and the candidate agent, e.g. as when non-neuronal cells are employed. In some instances, one parameter is measured. In some instances, multiple parameters are measured.

Cells useful for screening include any cell that expresses PirB or LILRB2 on its surface. For example, the cell may be a neuron, e.g. retinal ganglion cells (RGCs), cortical projection neurons, etc. In one embodiment of the invention, the neurons are a primary culture, e.g. of RGCs or cortical neurons. The cells are cultured in suitable medium, which will usually comprise appropriate growth factors, e.g. CNTF; BDNF; etc. The neurons are cultured for a period of time sufficient allow robust process outgrowth and then cultured with a candidate agent for a period of about 1 day to 1 week. In some embodiments, the neurons are cultured on a live astrocyte cell feeder in order to induce signaling for synapse formation. Methods of culturing astrocyte feeder layers are known in the art. For example, cortical glia can be plated in a medium that does not allow neurons to survive, with removal of non-adherent cells. In other embodiments, the cell may be non-neural, e.g. a fibroblast, a cell line, etc.

In other examples of screening assays for biologically active agents, the screen is a cell-free system. For example, candidate agents may be screened for their ability to interfere with the binding of Aβ oligomer to a PirB/LILRB2 extracellular domain (ECD) polypeptide by, e.g. surface plasmon resonance. In one such design, PirB/LILRB2 ECD polypeptide is immobilized to sensor surface, Aβ oligomer and candidate agent are passed over the sensor surface, and the binding of the Aβ oligomer in the presence of candidate agent is detected as a change in refractive index at the interface between the surface and a solution flowing over the surface changes. Alternatively, Aβ oligomer may be immobilized to the sensor surface, PirB/LILRB2 ECD polypeptide and candidate agent may be passed over the sensor surface, and the binding of the PirB/LILRB2 ECD polypeptide and candidate agent may be detected. A change in the refractive index in the presence of candidate agent relative to in the absence of candidate agent indicates that the agent has an effect on binding of Aβ oligomer to PirB/LILRB2.

Candidate agents of interest for screening include known and unknown compounds that encompass numerous chemical classes, primarily organic molecules, which may include organometallic molecules, inorganic molecules, genetic sequences, etc. as described above. An important aspect of the invention is to evaluate candidate drugs, including toxicity testing; and the like. Candidate agents of interest for screening also include nucleic acids, for example, nucleic acids that encode siRNA, shRNA, antisense molecules, or miRNA, or nucleic acids that encode polypeptides. Many vectors useful for transferring nucleic acids into target cells are available. Methods of providing these vectors are well known in the art. Candidate agents of interest for screening also include polypeptides, e.g. antibodies. Candidate agents may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Candidate agents are screened for biological activity by adding the agent to at least one and usually a plurality of cell samples, usually in conjunction with cells not contacted with the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Example 1

Soluble amyloid-β (Aβ) oligomers impair synaptic plasticity and cause synaptic loss associated with Alzheimer's disease (AD). We report that murine Paired immunoglobulin-like receptor B (PirB) and its human ortholog Leukocyte immunoglobulin-like receptor B2 (LilrB2), present in human brain, are receptors for Aβ oligomers, with nanomolar affinity. The first two extracellular IgG domains of PirB and LilrB2 mediate this interaction, leading to enhanced cofilin signaling associated with AD. In mice, the deleterious effect of Aβ oligomers on hippocampal LTP requires PirB, and in a transgenic model of AD, PirB not only contributes to memory deficits present in adult mice, but also mediates loss of synaptic plasticity in juvenile visual cortex. These findings imply that LilrB2/PirB contributes to human AD neuropathology and suggest therapeutic outcomes from blocking LilrB2/PirB function.

Materials and Methods

Animals and human specimens. Wild type and PirB−/− mice were generated as described previously (J. Syken, et al. (2006) "PirB restricts ocular-dominance plasticity in visual cortex." Science 313, 1795) and APP/PS1 transgenic mice (J. L. Jankowsky, et al. (2004) "Mutant presenilins specifically elevate the levels of the 42 residue beta-amyloid peptide in vivo: evidence for augmentation of a 42-specific gamma secretase." Hum Mol Genet 13, 159; J. L. Jankowsky, et al. (2001) "Co-expression of multiple transgenes in mouse CNS: a comparison of strategies." *Biomol Eng* 17, 157) were obtained from Jackson Laboratory. To produce experimental PirB; APP/PS1 littermates (PirB+/−, PirB−/−, PirB+/− Tg and PirB−/− Tg), APP/PS1 mice were crossed with PirB−/− mice, and resulting PirB+/− Tg males were crossed with PirB−/− females.

Fresh frozen specimens of human frontal cortex were obtained from the Human Brain and Spinal Fluid Resource Center, VA West Los Angeles Healthcare center (Los Angeles, Calif.), sponsored by NINDS/NIMH, National Multiple Sclerosis Society, Department of Veterans Affairs.

All studies were conducted with approval of the Stanford IRB and Animal Care and Use Committees and in compliance with NIH guidelines for the use of experimental animals and human specimens. All experiments and data analysis were performed blind to genotype.

TABLE 1

Human brain specimens

| ID  | age | Sex | Neuropath. Diagnosis | Dissected Area |
|-----|-----|-----|----------------------|----------------|
| C1  | 68  | M   | normal               | Cortex, frontal lobe |
| C2  | 58  | M   | normal               | Cortex, frontal lobe |
| C3  | 53  | M   | normal               | Cortex, frontal lobe |
| AD1 | 61  | M   | Alzheimer's disease* | Cortex, frontal lobe |
| AD2 | 63  | M   | Alzheimer's disease, early onset (Braak V) | Cortex, frontal lobe |
| AD3 | 64  | M   | Alzheimer's disease** | Cortex, frontal lobe |
| AD4 | 62  | M   | Alzheimer's disease (Braak V) | Cortex, frontal lobe |

*Microscopic analysis of CNS tissues indicates that this is an advanced case of AD (see also FIG. 4H).
**Microscopic analysis of CNS tissues indicates that this is an intermediate or early case of AD (FIG. 4H).

Reagents. Reagents were obtained from the following sources: antibodies to amyloid-β 1-16 (6E10; catalog #: SIG-39320), amyloid-β 17-24 (4G8; #51G39220) and neuronal class III tubulin (Tuj1; #PRB-435P) are from Covance (Emeryville, Calif.); monoclonal antibody specific to oligomeric Aβ (OMAB; #AS10 932) (29) from Agrisera (Vännäs, Sweden); antibodies to PirB (#AF2754; also detects PirA) and LilrB2 (#AF2078), as well as LilrB2-Fc (#2078-T4) and Nogo-66-Fc proteins (#3728-NG) from R&D Systems (Minneapolis, Minn.); antibodies to cofilin (#3312), SHP-2 (#3752), pLIMK1/2 (#3841), pTau (#9632) and anti-pTyr conjugated beads (#9419) from Cell Signaling Technology (Danvers, Mass.); antibody to pCofilin (#ab12866) and β-tubulin (#ab6046) from Abcam (Cambridge, Mass.); antibody to PirA/B (6C1; #550348) from BD Biosciences (San Jose, Calif.); antibodies to SHP-2 (#SC-7384) and c-Myc (9E10; #SC-40) from Santa Cruz Biotechnology (Santa Cruz, Calif.); antibody to MAP2 (#AB15452) from Millipore (Temecula, Calif.); antibody to PSD-95 (#MA1-045) from Thermo Scientific (Rockford, Ill.); antibody specific to intracellular domain of PirB (4730) was generated as described previously (J. Syken, et al. (2006) "PirB restricts ocular-dominance plasticity in visual cortex." Science 313, 1795). HRP-conjugated secondary antibodies to rabbit, mouse, goat and human IgG from Jackson ImmunoResearch (West Grove, Pa.); Secondary antibodies with Alexa 488, 568, 596 and 647 conjugates are from Invitrogen (Carlsbad, Calif.) and Jackson ImmunoResearch. Streptavidin-conjugated beads from Thermo Scientific (Rockford, Ill.). DMEM, Neurobasal-A, B-27, fetal bovine serum, horse serum, Lipofectamine, protein A conjugated beads and protein G conjugated beads are from Invitrogen. Protease inhibitor cocktail (#P8340), phosphatase inhibitor cocktails (#P5726, #P0044) and all other chemicals are obtained from Sigma (St. Louis, Mo.).

DNA constructs. Plasmids encoding Myc-tagged human LilrB1 (GenBank Accession No. NM_001081637.1), LilrB2 (GenBank Accession No. NM_001080978.1) and LilrB3 (GenBank Accession No. NM_006864.2), as well as murine PirA1 (GenBank Accession No. NM_011087.1), PirA4 (GenBank Accession No.: NM_011091.1) and PirB (accession #: NM_011095.2) or rat PirB (GenBank Accession No. NM_031713.1) from OriGene Technologies (Rockville, Md.); human LilrB2 (GenBank Accession No. BC036827) and Kir (GenBank Accession No. BC028206) are from Openbiosystems (Lafayette, Colo.). The PirB IRESEGFP construct was generated by subcloning the full-length cDNA of PirB from pSPORT6-PirB (J. Syken, et al., "PirB restricts ocular-dominance plasticity in visual cortex." Science 313, 1795 (Sep. 22, 2006)) into pCAGIG vector (Addgene; Cambridge, Mass.; Dr. C. Cepko, Harvard). To generate PirB-Fc and LilrB2-Fc constructs, full-length or deleted PirB or LilrB2 extracellular domains are amplified by PCR, digested with NcoI/BglII (PirB-Fc constructs) or EcoRV/BglII (LilrB2-Fc constructs), and subcloned into pFUSE-hIgG1e3-Fc2 vectors (InvivoGen; San Diego, Calif.), using primers as follows. Amino acid residues corresponding to subcloned IgG (D) domain are noted on left.

PirB:24-643 (D1D6)
Fwd:
(SEQ ID NO: 7)
5'-ggccatggggtccctccctaagcctatcctcaga-3'

Rev:
(SEQ ID NO: 8)
5'-ccagatctagccttcaggtacatatgcagtccacctag-3'

PirB:221-643 (D3D6)
Fwd:
(SEQ ID NO: 9)
5'-ggccatgggtaatctccaaaaaccaaccatcaaggc-3'

Rev:
(SEQ ID NO: 10)
5'-ccagatctagccttcaggtacatatgcagtccacctag-3'

PirB:419-643 (D5D6)
Fwd:
(SEQ ID NO: 11)
5'-ggccatggggctgtccaagaagccctctctg-3'

Rev:
(SEQ ID NO: 12)
5'-ccagatctagccttcaggtacatatgcagtccacctag-3'

PirB:24-224 (D1D2)
Fwd:
(SEQ ID NO: 13)
5'-ggccatggggctgtccaagaagccctctctg-3'

Rev:
(SEQ ID NO: 14)
5'-ccagatctttggagattacctgagaccaggagctcc-3'

PirB:24-422 (D1D4)
Fwd:
(SEQ ID NO: 15)
5'-ggccatggggctgtccaagaagccctctctg-3'

Rev:
(SEQ ID NO: 16)
5'-ccagatctcttggacagccctgagatgagtatttgttg-3'

PirB:221-422 (D3D4)
Fwd:
(SEQ ID NO: 17)
5'-ggccatgggtaatctccaaaaaccaaccatcaaggc-3'

Rev:
(SEQ ID NO: 18)
5'-ccagatctcttggacagccctgagatgagtatttgttg-3'

-continued

Lilrb2:24-458 (D1D4)
Fwd:
(SEQ ID NO: 19)
5'-ccgatatcagggaccatccccaagcccaccct-3'

Rev:
(SEQ ID NO: 20)
5'-ccagatctgtgccttcccagaccactttgggg-3'

Lilrb2:219-458 (D3D4)
Fwd:
(SEQ ID NO: 21)
5-ccgatatcaccaggtgtttctaagaagccatcactctcag-3'

Rev:
(SEQ ID NO: 22)
5'-ccagatctgtgccttcccagaccactttgggg-3'

Lilrb2:24-223 (D1D2)
Fwd:
(SEQ ID NO: 23)
5'-ccgatatcagggaccatccccaagcccaccct-3'

Rev:
(SEQ ID NO: 24)
5'-ccagatctcttagaaacacctgggaccaggagctcc-3'

Lilrb2:119-323 (D2D3)
Fwd:
(SEQ ID NO: 25)
5-ccgatatcaggagcctacccaaaacccaccctctc-3'

Rev:
(SEQ ID NO: 26)
5-ccagatctgccatggatctgtcctgtgatcaggatg-3'

Aβ preparation and analysis. Biotinylated (N-terminal) or non-biotinylated synthetic human Aβ1-42 and Aβ1-40 are obtained from Anaspec (Fremont, Calif.), and prepared as described (J. Lauren (2009) Nature 457, 1128; J. L. Jankowsky et al. (2001) Biomol Eng 17, 157). Dissolved peptides were sonicated for 30 seconds and diluted in 1× phosphate buffered saline (PBS; 1.06 mM KH2PO4, 155.17 mM NaCl, 2.97 mM Na2HPO4-7H2O, pH7.4; Invitrogen; #10010) to the final concentration of 100 μM to make freshly prepared Aβ peptides (Mono-Aβ42). The peptides were then incubated at 22° C. for 16 hr followed by 24 hr incubation at 4° C., centrifuged at 16,000×g for 15 min, and the supernatant was collected as oligomerized Aβ peptides (Oligo-Aβ42). Typically ~50-60% of Aβ42 peptides were discarded as precipitates after oligomerization and centrifugation (FIG. 5A) and ~10-20% of Aβ42 peptides remained as monomers or low-n oligomers (FIGS. 1, A and B). Thus about 30% of total Aβ42 peptides represents the high-n species of Aβ oligomers (The Kd is calculated using concentration of monomer equivalent for total Aβ42 peptides (FIG. 5A). Since the Kd of mono-Aβ42 is minimal (FIG. 1J), it is likely that the Kd for PirB and high-n Aβ42 oligomers is much lower than 180 nM. If the high-n species of Aβ42 responsible for binding has a DPn≈60 (21) and consists of ~30% of total Aβ42 peptides (FIGS. 1, A and B, 5A), the corrected Kd would be approximately 1 nM.)

To analyze monomeric or oligomeric status of Aβ peptides in liquid phase, fresh or oligomerized Aβ42 peptides were injected onto a Superdex75 10/300 size exclusion column (SEC) on an AKTAPurifier (GE healthcare, Pittsburgh, Pa.). Sample retention volume was monitored via UV absorbance at 215 nm. The relative retention size was compared to gel filtration standards of known molecular weights (Bio-Rad Gel Filtration Standard #151-1901). Consistent oligomerization between Aβ preparations was also confirmed by Western blot analysis in partially reduced condition (e.g. FIG. 1B; see below).

Cellular and neuronal binding assays. HEK293 cells were transiently transfected (Lipofectamine; Invitrogen) with expression vectors (T. Kim, et al. (2009) "NRH2 is a trafficking switch to regulate sortilin localization and permit proneurotrophin-induced cell death." Embo J 28, 1612) encoding IRES-EGFP, PirB-IRES-EGFP, PirB, PirA1, PirA4, rat PirB, LilrB1, LilrB2, LilrB3, Kir or control empty vectors, and plated onto 8 chamber slides (Thermo Scientific). Two days post-transfection, cells were treated with biotinylated mono- or oligo-Aβ42 for 2 h at 37° C., washed twice, and fixed with 2% paraformaldehyde (PFA) in 1× PBS for 20 min. The bound Aβ peptides were visualized with streptavidin-Alexa fluorophore conjugates (Alexa 488, 598 or 647; wavelength choice depending on experiments) (J. Lauren, et al. (2009) "Cellular prion protein mediates impairment of synaptic plasticity by amyloid-beta oligomers." Nature 457, 1128). DAPI was used to counterstain cell nuclei; IRES-EGFP was used to monitor construct transfection; anti-PirB (4730) or c-Myc antibodies were used to co-stain PirB or LilrBs. Fluorescent images were captured with fixed illumination and exposure time using a Nikon 20× objective of numerical aperture 0.75, and then fluorescence intensity was quantified using ImageJ software (NIH). In each experiment, values from control vector transfected cells were used as background, and subtracted from those of experimental cells.

For quantitative analysis of mono-Aβ42 or oligo-Aβ42 binding to PirB or LilrB2, and to estimate their binding affinities, transfected HEK293 cells were treated with varying concentrations of Aβ42 peptides, and the bound Aβ peptides were visualized and quantified as described above. Values from control cells (IRES-EGFP or control empty vector transfected HEK293) were subtracted from those of experimental cells to measure specific binding (i.e. ΔPirB- or ΔLilrB2-HEK293 cells). Using Prism software (GraphPad, La Jolla, Calif.), saturation curves and scatchard plots were generated, and half-saturation points (dissociation constant; Kd) were determined.

To monitor Aβ42 oligomer binding to neuronal PirB, cortical neurons from embryonic day 16 (E16) WT or PirB-/- mice (C. Viesselmann, et al. (2011) "Nucleofection and primary culture of embryonic mouse hippocampal and cortical neurons." J Vis Exp.) were plated in 96-well plates and cultured for 21 days (DIV21). After treating with varying concentrations of biotinylated Aβ oligomers or vehicle, cells were washed twice with PBS, fixed with 2% PFA for 20 min and incubated with Alkaline phosphatase-conjugated SAv for 1 h at RT. The bound Aβ oligomers were detected using the QuantiChrom AP assay (DALP-250; BioAssay Systems, Hayward, Calif.) (J. K. Atwal et al. (2008) "PirB is a functional receptor for myelin inhibitors of axonal regeneration." Science 322, 967). To estimate Aβ42 oligomer binding to PirB in cortical neurons (ΔPirB), values of Aβ binding to PirB-/- neurons were subtracted from those to WT neurons and represented as WT minus PirB-/-.

Immunoprecipitation and western blotting. Soluble protein extracts of mouse and human brains were prepared based on previous publications (C. M. William et al. (2012) "Synaptic plasticity defect following visual deprivation in Alzheimer's disease model transgenic mice." J Neurosci 32, 8004; J. Syken, et al. (2006) "PirB restricts ocular-dominance plasticity in visual cortex." Science 313, 1795; M. A. Sherman, et al (2011) "Detecting abeta*56 oligomers in brain tissues." Methods Mol Biol 670, 45) to permit immunoprecipitation and detection of PirB, LilrB2 and Aβ. Mouse or human forebrains were dissected and homogenized in approximately 10 volumes of ice-cold lysis buffer containing 1% Triton-X 100, 150 mM NaCl, 50 mM Tris (pH 7.4), 1 mM phenylmethylsulfonyl fluoride, 1 mM sodium fluoride, protease inhibitor and phosphatase inhibitor cocktails. Samples were centrifuged at 16,000×g for 30 min at 4° C., and supernatants were pre-cleared sequentially with protein A beads and protein G beads for 30 min each at 4° C. followed by an additional centrifugation at 16,000×g for 90 min at 4° C. to save clear detergent-soluble fractions of brain extracts.

To purify hippocampal crude synaptosomes, dissected hippocampi from adult mice (P200) were homogenized in a buffer containing 0.32 M sucrose, 20 mM HEPES (pH 7.4), 1 mM EDTA with protease and phosphatase inhibitors and centrifuged for 10 min at 700×g at 4° C. Supernatants were then centrifuged at 10,000×g for 10 min and pellets (crude synaptosomal fractions) were saved for Western blot analysis (N. Li, et al. (2010) "mTOR-dependent synapse formation underlies the rapid antidepressant effects of NMDA antagonists." *Science* 329, 959).

For immunoprecipitation experiments, HEK293 cell lysates, brain extracts or cortical neuron lysates were incubated with appropriate antibodies overnight at 4° C. and immunoprecipitates were collected on protein G beads with extensive washes. Samples were separated by 4-20% or 4-15% SDS-PAGE (Bio-Rad Laboratories, Hercules, Calif.), transferred to Polyvinylidene fluoride (PVDF) membranes (Millipore), and probed with specific antibodies followed by visualization with enhanced chemiluminescence (ECL, Thermo Scientific) and x-ray film (Fuji, Lightlabs, Dallas, Tex.). Typically 10-20 mg of these brain extracts was used for each immunoprecipitation represented in FIG. 2E, FIG. 4A, FIG. 12 and FIG. 13.

To analyze SDS-stable oligomeric forms of Aβ (J. Lauren, et al. (2007) "Cellular prion protein mediates impairment of synaptic plasticity by amyloid-beta oligomers." Nature 457, 1128 (Feb. 26, 2009); T. J. Nelson, et al., "Protection against beta-amyloid-induced apoptosis by peptides interacting with beta-amyloid." J Biol Chem 282, 31238), as well as dimeric PirB, protein samples were prepared in Laemmli buffer without β-mercaptoethanol, without boiling steps, and separated by SDS-PAGE (partially reduced condition; i.e. FIG. 10). For Western blot analysis, samples were post-denatured by boiling the transferred membrane for 10 min in PBS, before probing with antibodies.

For quantitative analysis of cofilin phosphorylation (pCofilin/total Cofilin), the signals for phospho-cofilin were quantified with ImageJ (T. Kim, et al. (2009) "NRH2 is a trafficking switch to regulate sortilin localization and permit proneurotrophin-induced cell death." *Embo J* 28, 1612) and normalized by the signal intensities quantified from total cofilin bands. Detection of PSD-95 or pLIMK1/2 levels was determined using the same method. The reported result from forebrain samples (FIGS. 4B and 4D) is average±SEM from 4 independent experiments (total 13 animals/genotype; forebrains from 2 to 4 animals were pooled in each experiment).

Aβ binding to soluble PirB-Fc and LilrB2-Fc. To generate PirB-Fc or LilrB2-Fc proteins, HEK293T cells were transfected with various PirB-Fc or LilrB2-Fc constructs described above, and secreted PirB-Fc or LilrB2-Fc proteins in the conditioned media were purified using a protein A column (J. Lauren, et al. (2009) "Cellular prion protein mediates impairment of synaptic plasticity by amyloid-beta oligomers." Nature 457, 1128). To identify the domains of PirB or LilrB2 responsible for Aβ oligomer binding, full-length or deleted PirB-Fc or LilrB2-Fc proteins were incubated with Aβ42 oligomers for 2 h at 4° C. and washed extensively, and the bound Aβ42 oligomer was analyzed by Western blotting using Aβ antibody (6E10 or 4G8). Truncated PirB-Fc lacking the binding domain for Aβ oligomers, PirB (D5D6)-Fc was used as controls; anti-Aβ oligomer specific antibodies (OMAB) (M. Lindhagen-Persson, et al., "Amyloid-beta oligomer specificity mediated by the IgM isotype—implications for a specific protective mechanism exerted by endogenous auto-antibodies." PLoS One 5, e13928 (2010)) (FIG. 10D) were used to verify oligomeric status of immunoprecipitated Aβ peptides. The Aβ signals were quantified as described above.

Electrophysiology. Brains were isolated in compliance with Stanford University guidelines, from either 4-5 month old mice (hippocampal slice experiments) or P28-32 mice (visual cortical slice experiments). Mice were anaesthetized intraperitoneally with ketamine (132 mg/kg; Phoenix, St. Joseph, Mo.)-xylazine (14 mg/kg; Akorn, Decatur, Iowa)-acepromazine (0.2 mg/kg; Boehringer Ingelheim, St. Joseph, Mo.) cocktail before rapid decapitation and extraction of the brain. All electrophysiology results were analyzed with pCLAMP software (Molecular Devices, Sunnyvale, Calif.), blind to genotype. Only experiments without obvious drift in baseline fEPSP slope and without significant contamination from population spikes were included for analysis.

Hippocampal slice electrophysiology. LTP experiments were performed on slices prepared from hippocampus (J. Lauren, et al. (2009) "Cellular prion protein mediates impairment of synaptic plasticity by amyloid-beta oligomers." Nature 457, 1128; H. W. Kessels, et al. (2010) "The prion protein as a receptor for amyloid-beta." Nature 466, E3; M. Fa et al., (2010) "Preparation of oligomeric beta-amyloid 1-42 and induction of synaptic plasticity impairment on hippocampal slices." J Vis Exp) of adult WT or PirB−/− mice. Brains were rapidly dissected and immersed in ice-cold Ca++-free artificial cerebrospinal fluid (Ca++-free ACSF; containing 125 mM NaCl, 26 mM NaHCO3, 2.3 mM KCl, 1.26 mM KH2PO4, 1.3 mM MgCl2, and 25 mM glucose), pH 7.4, equilibrated with 95% O2 and 5% CO2. Hippocampi were quickly dissected from the brains and sectioned in the transverse plane into 400 μm-thick slices using a vibrating microtome (VT1000S, Leica Microsystems, Buffalo Grove, Ill.). Slices were then transferred to a recovery chamber containing ACSF (as Ca++-free ACSF above, but with the addition of 2.5 mM CaCl2), equilibrated with 95% O2 and 5% CO2, and incubated for at least 3 hours at room temperature until use. Following incubation, brain slices were transferred to recording chambers and superfused by recycling a volume of 200 ml at a rate of 2 ml/min with 30° C. ACSF with oligo-Aβ42 (200 nM total peptide) or vehicle, equilibrated with 95% O2 and 5% CO2. One recording chamber was superfused with peptide-containing ACSF, and the other recording chamber was simultaneously superfused with ACSF alone (vehicle control).

Field excitatory postsynaptic potentials (fEPSPs) were elicited by stimulation of Schaffer collaterals using 200 μs pulses delivered by a bipolar concentric stimulating electrode (125 μm outer diameter; FHC, Bowdoin, Me.). Borosilicate glass microelectrodes were filled with ACSF or ACSF with 200 nM oligomeric Aβ42 for extracellular recording (1-2 MΩ), and placed in the stratum radiatum in the CA1 region. Baseline responses were obtained every 30 s with a stimulation intensity that yielded 30% of the maximal response (between 10 and 37 μA). One episode of theta burst stimulation (TBS; 10 bursts of 4 pulses at 100 Hz, with an interburst interval of 200 ms) (J. Lauren, et al. (2009) "Cellular prion protein mediates impairment of synaptic plasticity by amyloid-beta oligomers." Nature 457, 1128) was given at the stimulation intensity given at baseline, and fEPSPs were recorded every 30 s for 60 min after inducing LTP.

Visual cortical slice electrophysiology. LTD experiments were performed on slices prepared from visual cortex of juvenile mice with or without the APP/PS1 transgene (R. A. Crozier, et al. (2007) "Deprivation-induced synaptic depression by distinct mechanisms in different layers of mouse visual cortex." Proc Natl Acad Sci USA 104, 1383). Slices were recorded, and results analyzed, blind to genotype. Brains were rapidly dissected and immersed in ice-cold slicing buffer containing 135 mM N-methyl D-glucamine (NMDG), 1 mM KCl, 1.2 mM KH2PO4, 1.5 mM MgCl2, 0.5 mM CaCl2, 20 mM choline bicarbonate, and 10 mM glucose, pH 7.4, equilibrated with 95% O2 and 5% CO2. Forebrains were sectioned in the coronal plane into 400 µm-thick slices using a vibrating microtome (VT1000S, Leica Microsystems, Buffalo Grove, Ill.). Slices containing visual cortex were transferred to a recovery chamber containing ACSF (as described above) equilibrated with 95% O2 and 5% CO2, and incubated at 32° C. for 45 min followed by at least 45 min at room temperature until use. Following incubation, brain slices were transferred to recording chambers and superf used at a rate of 2 ml/min with 30° C.-31° C. ACSF, equilibrated with 95% O2 and 5% CO2. Borosilicate glass microelectrodes were filled with ACSF for extracellular recording (1-2 MΩ), and placed in layer 2/3 of primary visual cortex (V1).

Synaptic responses were evoked from layer 4 with 200 µs pulses delivered by a bipolar concentric stimulating electrode (125 µm outer diameter; FHC, Bowdoin, Me.). Baseline responses were obtained every 30 s with a stimulation intensity that yielded a half-maximal response (between 13 and 85 µA). Three episodes of low-frequency stimulation (900 pulses at 1 Hz, at the stimulation intensity used at baseline) spaced 25 min apart were delivered to induce LTD. The field excitatory postsynaptic potentials (fEPSPs) were recorded every 30 s for 60 min after inducing LTD.

Recognition memory tests. Object and place recognition memory were tested in the Stanford Behavioral and Functional Neuroscience Laboratory according to standard protocols (M. Faizi, et al., "Thy1-hAPP (Lond/Swe+) mouse model of Alzheimer's disease displays broad behavioral deficits in sensorimotor, cognitive and social function." Brain Behav 2, 142 (March, 2012); M. Cisse, et al. (2011) "Reversing EphB2 depletion rescues cognitive functions in Alzheimer model." (Nature 469, 47; P. L. McClean, et al. (2011) "The diabetes drug liraglutide prevents degenerative processes in a mouse model of Alzheimer's disease." J Neurosci 31, 6587). Micewere transferred to the testing room and acclimatized for at least 1 hr before testing. The testing was performed in a chamber consisting of two arenas, each measuring 20 cm×40 cm. On Day 1, animals were habituated to the room for one hour and then placed in the arena for 15 min. On day 2, each mouse was presented with two identical objects in the same chamber and allowed to explore freely for 10 min. Three hours after this training session, animals were subjected to the novel place recognition (NPR) test. Of the two identical objects in each arena, the left object was moved to new location. Behavior was recorded with video tracking (Ethovision 8.1 XT) and the amount of time spent sniffing and head orientation within 1 cm of the objects was scored as interaction with the objects. After 10 min session, mouse was returned to the home cage. Arenas and objects were cleaned with % Virkon between each mouse. On day 3, the novel object recognition (NOR) test was performed: mice were placed back into the same arena used for NPR test on day 2, but one of the original objects was replaced with a novel, unfamiliar object of different shape and texture.

Frequency of interactions with the objects, as well as time spent exploring each object were recorded for subsequent data analysis. All behavior and analyses were performed blind to genotype. Exploration time (%) was defined as (TN/(TN+TF))×100 or (TF/(TN+TF))×100, where TN represents the amount of time exploring the novel object/place and TF, the familiar object/place.

OD plasticity measurement using Arc induction. As described previously (C. M. William et al. (2012) "Synaptic plasticity defect following visual deprivation in Alzheimer's disease model transgenic mice." J Neurosci 32, 8004; Y. Tagawa, et al. (2005) "Multiple periods of functional ocular dominance plasticity in mouse visual cortex." Nat Neurosci 8, 380), monocular enucleation (ME) was performed on postnatal day 22 (P22) mice to assess OD plasticity in visual cortex ipsilateral to the remaining eye. After 10 days of monocular vision, mice were placed briefly in total darkness for approximately 15 hr, and then to induce Arc mRNA, the mice were put in a room and exposed to bright fluorescent lighting through the remaining eye for 30 min. Then mice were deeply anaesthetized with Halothane (Halocarbon, River Edge, N.J.), brains were removed rapidly and flash-frozen in M-1 mounting medium (GE Healthcare Biosciences, Pittsburgh, Pa.). Coronal cryosections (8-10 µm) through visual cortex were collected on Superfrost slides (Thermo Fisher Scientific, Fremont, Calif.). To measure the width of visual cortex containing neurons responding to stimulation of the ipsilateral eye, the induction of mRNA for the immediate early gene Arc was assessed by in situ hybridization analysis using Digoxigenin-labeled antisense riboprobe for Arc (C. M. William et al. (2012) J Neurosci 32, 8004), followed by measurement of the width of the Arc-positive domain in layers 2/3 of visual cortex using ImageJ software. 3 to 15 sections/animal were analyzed. All measurements and analyses were performed blind to genotype.

This technique provides a sensitive measure of open-eye strengthening that accurately reflects OD plasticity as also assessed using single unit recording, visual evoked potential, or intrinsic signal imaging methods (C. M. William et al. (2012) J Neurosci 32, 8004; Y. Tagawa, et al. (2005) Nat Neurosci 8, 380), with an advantage that laminar and single cell resolution is provided. It should be noted that Arc has been recently implicated in Amyloid Precursor Protein (APP) trafficking and processing (J. Wu, et al. (2011) "Arc/Arg3.1 regulates an endosomal pathway essential for activity-dependent beta-amyloid generation." Cell 147, 615), but APP/PS1 mice have been shown to maintain intact Arc mRNA induction in response to ME and light exposure protocol described above (C. M. William et al. (2012) J Neurosci 32, 8004).

Statistical analyses. Statistical significance was typically determined by two-tailed Student's t-test after testing for normal distribution; paired t-test was used for NOR and NPR tests. Nonparametric Mann-Whitney U-test (Prism software; GraphPad) was used to calculate P values for analysis and comparison of separate Western Blots. Saturation binding curves, Kd and Scatchard plots were generated using Prism software. All analyses were performed blind to genotype.

Results

Aβ oligomers may exert some of their adverse effects on synaptic plasticity and memory by binding to receptors, thereby perturbing or engaging downstream signaling. At least two Aβ receptors, cellular Prion Protein (PrPC) and Ephrin type-B receptor 2 (EphB2) have been identified, and downstream signaling from both alters N-methyl-D-aspartate (NMDA) receptor function in response to Aβ (M. Cisse et al., (2011) Nature 469, 47; J. Laurén et al. (2009) Nature 457, 1128; J. W. Um et al., (2012) Nat Neurosci 15, 1227). Aβ oligomers are also known to engage other signaling pathways, including the actin-severing protein cofilin and protein phosphatases PP2A and PP2B/calcineurin, mediating spine loss and synaptic defects (G. M. Shankar et al., (2007) Natural oligomers of the Alzheimer amyloid-beta protein induce reversible synapse loss by modulating an NMDA-type glutamate receptor dependent signaling pathway. J Neurosci 27, 2866; X. Wang et al., (2012) Pyruvate Prevents the Inhibition of the Long-term Potentiation Induced by Amyloid-beta through Protein Phosphatase 2A Inactivation. J Alzheimers Dis), but signaling upstream of these pathways is not well understood.

Figures 8A, 8B:
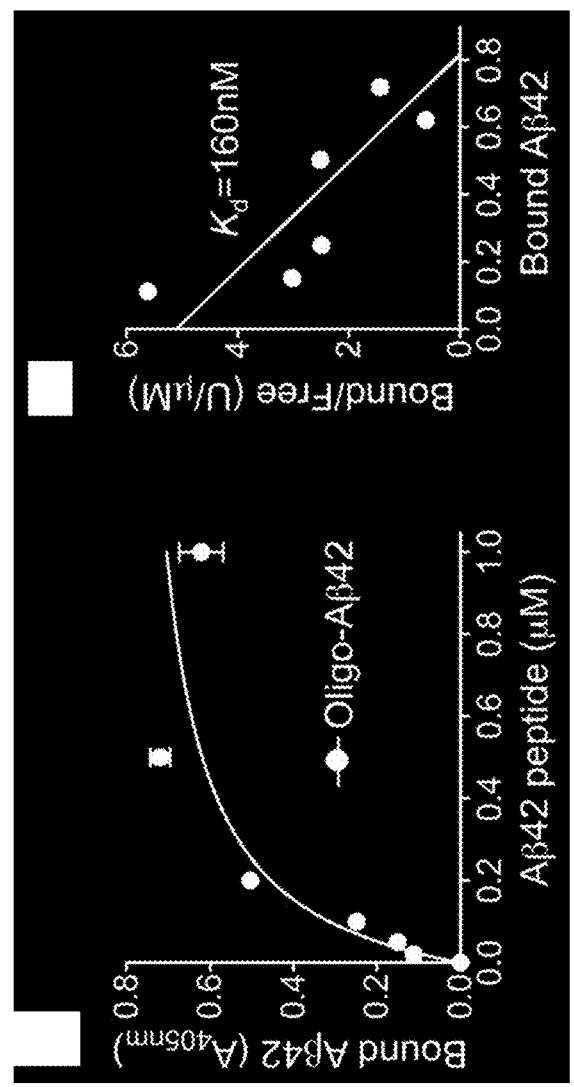
FIG. 8A-8B demonstrates dose-dependent binding of oligo-Aβ42 to PirB.

To determine if PirB can act as a receptor for soluble Aβ oligomers, biotinylated synthetic human Aβ1-42 (Aβ42) peptides were prepared either without (mono-Aβ42) or with oligomerization (oligo-Aβ42; consists primarily of high-n oligomers) (FIGS. 1, A and B, and FIG. 5A) (J. Laurén et al. (2009) Cellular prion protein mediates impairment of synaptic plasticity by amyloid-beta oligomers. Nature 457, 1128). Based on SEC (FIG. 1A) and Western blot analyses (FIG. 1B) as well as previous studies (Kamenetz et al. (2003) Neuron 37, 925), average degree of polymerization (DP) of oligomerized Aβ42 is estimated to be 60 (DPn≈270 kDa/4.5 kDa). The mono-Aβ42 preparation consists almost exclusively of monomeric peptides with a small fraction (<5%) of low-n oligomers (dimer, trimer or tetramer; FIGS. 1, A and B). We then measured binding of Aβ42 peptides to HEK293 cells that expressed mouse PirB (PirB-IRES-EGFP) or control vector (IRES-EGFP). Oligomerized Aβ42 peptides bind PirB-expressing cells about 6-fold more than monomeric Aβ42 (FIG. 1, A to D). Oligo-Aβ42 is consistently associated with PirB protein, as seen both by co-immunostaining (FIG. 1E: arrowheads) and by coimmuno-precipitation (fig. S1, B and C), indicating a direct interaction with PirB. This assay also confirms previously reported Nogo-66 binding to PirB (FIG. 6) (J. K. Atwal et al., (2008) PirB is a functional receptor for myelin inhibitors of axonal regeneration. Science 322, 967). In contrast, binding of Aβ42 oligomers was not evident in heterologous cells expressing mouse PirA1 and PirA4, or an isoform of rat PirB, receptors closely related to mouse PirB (FIGS. 1, F and G, and FIG. 7), indicating that Aβ42 oligomers bind selectively to PirB. Oligo-Aβ42 binding to PirB expressed in HEK293 cells is saturable, with an apparent dissociation constant (Kd) of 180 nM monomer-equivalent of total Aβ42 peptide (FIG. 1, H to J) (The Kd is calculated using concentration of monomer equivalent for total Aβ42 peptides (FIG. 5A). Since the Kd of mono-Aβ42 is minimal (FIG. 1J), it is likely that the Kd for PirB and high-n Aβ42 oligomers is much lower than 180 nM. If the high-n species of Aβ42 responsible for binding has a DPn≈60 (21) and consists of ~30% of total Aβ42 peptides (FIGS. 1, A and B, and 5), the corrected Kd would be approximately 1 nM). An alkaline phosphatase assay also gives similar binding affinity (Kd=160 nM; FIG. 8). In contrast, mono-Aβ42 exhibits no apparent binding affinity to PirB (FIG. 1, H to J).

Aβ42 oligomer binding to cultured cortical neurons from PirB−/− mice is diminished by about 50% compared to WT neurons, indicating that binding is PirB dependent. The estimated Kd for Aβ42 oligomers and neuronal PirB is 110 nM (FIG. 1K), similar to that observed for PirB-HEK293 cells (FIGS. 1, I and J). We note that this binding is not completely abolished in the absence of PirB (FIG. 1K), suggesting that additional binding sites for Aβ oligomers exist (M. Cisse et al., (2011) Reversing EphB2 depletion rescues cognitive functions in Alzheimer model. Nature 469, 47; J. Laurén et al. (2009) Cellular prion protein mediates impairment of synaptic plasticity by amyloid-beta oligomers. Nature 457, 1128; T.-I. Kam et al., (2013) FcgammaRIIb mediates amyloid-beta neurotoxicity and memory impairment in Alzheimer's disease. J Clin Invest 123, 2791). Together, results indicate that PirB is a new high-affinity receptor for Aβ oligomers.

The human homolog of murine PirB is Leukocyte immunoglobulin-like receptor B, comprised of 5 family members, LilrB1-LilrB5 (T. Takai (2005) Paired immunoglobulin-like receptors and their MHC class I recognition. Immunology 115, 433; J. K. Atwal et al., (2008) PirB is a functional receptor for myelin inhibitors of axonal regeneration. Science 322, 967). To identify which of these orthologs functions analogous to PirB as a receptor for Aβ oligomers, we examined the three most related LilrB receptors, LilrB1, 2 and 3 (T. Takai, (2005), supra; J. K. Atwal et al., (2008), supra; J. Zheng et al., (2012) Inhibitory receptors bind ANGPTLs and support blood stem cells and leukaemia development. Nature 485, 656; G. Ma et al., (2011) Paired immunoglobin-like receptor-B regulates the suppressive function and fate of myeloid-derived suppressor cells. Immunity 34, 385), as well as a moderately related human killer immune receptor (Kir) (FIG. 2A). Aβ42 oligomers robustly bind to LilrB2-expressing heterologous cells, but not to LilrB1-, LilrB3- or Kir (3DL1)-expressing cells (FIGS. 2B and 9A). Binding is saturable, with an apparent Kd of 206 nM (FIGS. 2, C and D; also FIGS. 9, B and C: Kd=250 nM). LilrB2 has minimal binding to mono-Aβ42 (FIGS. 2, C and D), indicating selective binding with Aβ42 oligomers. LilrB2 proteins were detected in human brain specimens from both Alzheimer's patients (AD) and non-AD adults (non-AD) (Table 1), with no significant difference in levels (FIGS. 2, E and F; but downstream signaling is altered in AD—see FIGS. 4, H and I). These results indicate that LilrB2 is available as a receptor for Aβ oligomers in human brain. LilrB2 has also been identified as a human ortholog of PirB for other non-immune ligands discovered recently: in vitro, PirB and LilrB2 act as functional receptors to inhibit axonal outgrowth on Nogo, myelin associated glycoprotein, and oligodendrocyte myelin glycoprotein substrates (J. K. Atwal et al., (2008) PirB is a functional receptor for myelin inhibitors of axonal regeneration. Science 322, 967); in the haematopoetic system, angiopoietin-like proteins can also bind to PirB and LilrB2 to support stem cell and leukemia development (J. Zheng et al., (2012) Inhibitory receptors bind ANGPTLs and support blood stem cells and leukaemia development. Nature 485, 656). These observations imply that mouse PirB may have diverse functions well beyond inhibitory signaling in the innate immune system, and that LilrB2 may execute these roles in humans, particularly in the nervous system.

Figure 10B:
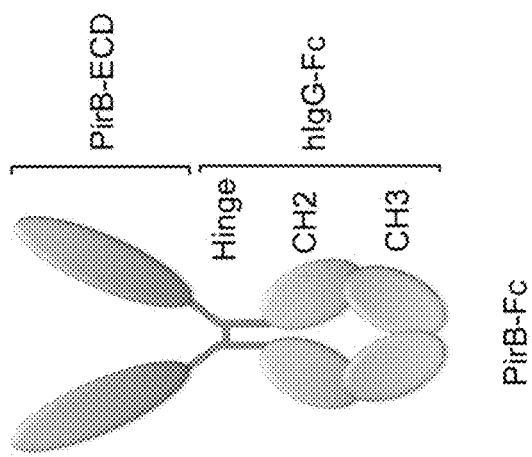
FIG. 10A-10D demonstrates that Aβ42 oligomers bind to the D1D2 domain of PirB.
Figure 10A:
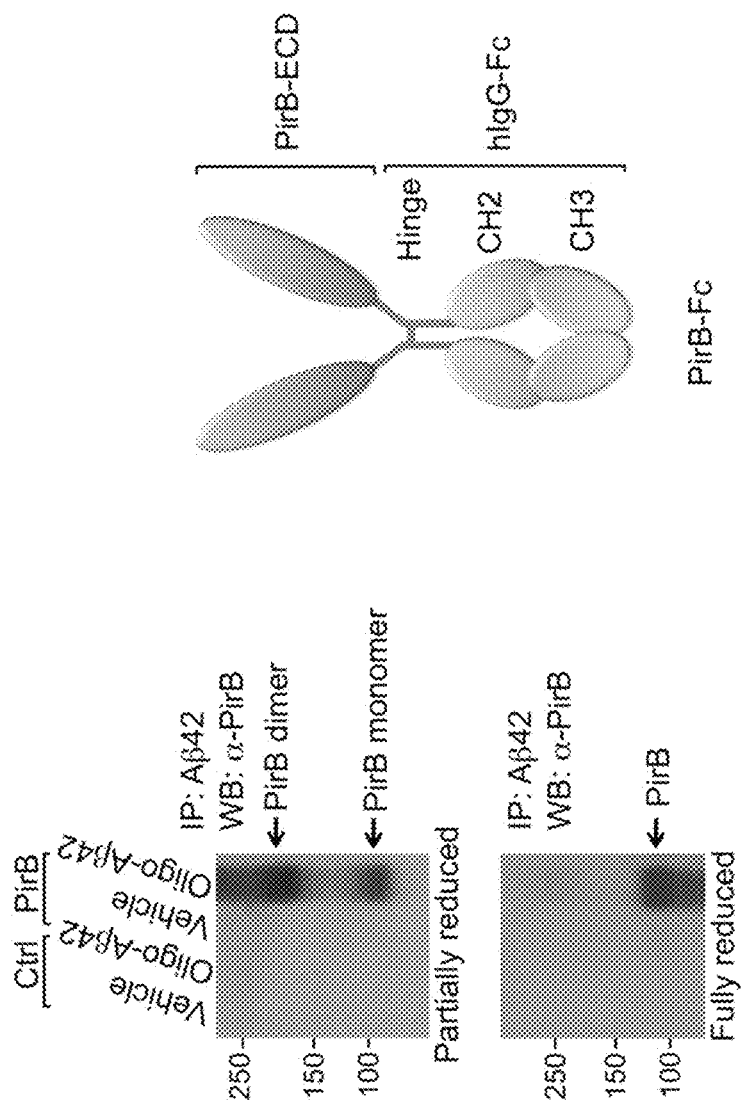
Figures 10C, 10D:
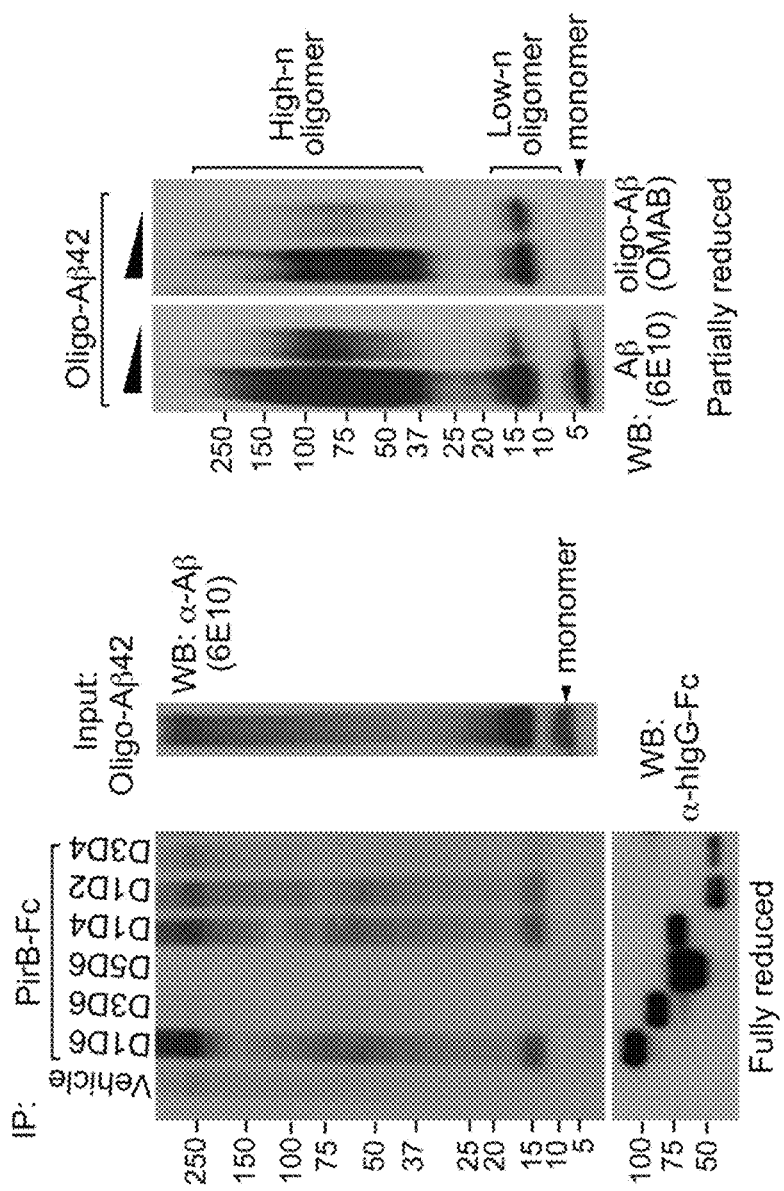
Figure 12:
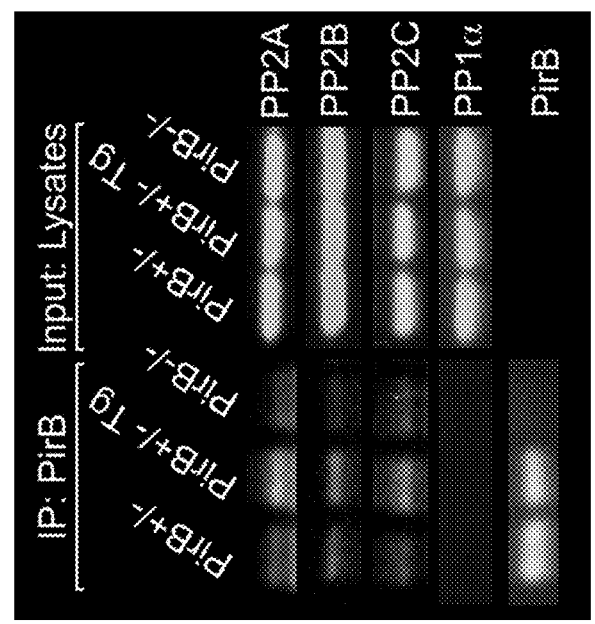
FIG. 12 illustrates that Interactions between PirB and protein phosphatases are increased in APP/PS1 brain. Recruitment of Ser/Thr phosphatases, PP2A, PP2B/calcineurin or PP2C, to PirB is increased in forebrains of juvenile (P30) APP/PS1 transgenic mice (PirB+/− Tg) compared to non-transgenic littermates, assessed by immunoprecipitation of PirB from forebrain lysates followed by probing with indicated antibodies.

To determine domains of PirB or LilrB2 responsible for Aβ oligomer binding, full-length or deletion mutants of PirB and LilrB2 were made (FIG. 2G). Because Aβ oligomers appear to bind preferentially to dimeric PirB in heterologous cells (FIG. 10A), soluble dimeric forms of PirB or LilrB2 extracellular domain were constructed using human IgG1-Fc (FIG. 10B). In vitro binding to Aβ42 oligomers revealed that the two most N-terminal IgG domains (D1 D2) of PirB and of LilrB2 are critical, whereas the PirBD5D6 and LilrB2-D3D4 domains have minimal affinity (FIGS. 2, G and H, and FIG. 10C) (The closest human homolog for murine PirB among the 5 members of the human leukocyte immunoglobulin (Ig)-like receptor B (LilrB) family has been considered to be LilrB3 based on overall amino acid sequence homology (FIG. 2A) (Ma et al. (2011) Immunity 34, 385). However, domain sequence analysis indicates that the D1D2 domain of LilrB2 aligns with the D1D2 domain of PirB, where Aβ oligomer binding occurs, whereas the D1D2 domain of LilrB3 aligns more closely with the D3D4 domain of PirB, suggesting that conservation present in the D1D2 domains as well as tertiary structure surrounding Aβ binding site is important for this binding). In this assay, PirB-Fc, LilrB2-Fc and PirB (D1 D2)-Fc proteins pull down high-n Aβ42 oligomers (FIG. 2H), recapitulating co-immunoprecipitation results (FIG. 5B). PirB (D5D6)-Fc was used as a negative control and the oligomeric status of bound Aβ42 was confirmed using the oligomer-specific antibody OMAB (M. Lindhagen-Persson, et al. (2010) Amyloid-beta oligomer specificity mediated by the IgM isotype—implications for a specific protective mechanism exerted by endogenous auto-antibodies. PLoS One 5, e13928) (FIGS. 2H and 10D). These results indicate that PirB and LilrB2 are potent receptors for Aβ42 oligomers, and that their D1D2 domains are sufficient to mediate binding.

If PirB or LilrB2 mediates deleterious effects of Aβ on synaptic function, then deletion of PirB should mitigate them in cellular or animal models of AD. A cellular mechanism proposed to underlie memory impairment in AD is loss of hippocampal LTP resulting from the presence of soluble Aβ oligomers (J. J. Palop, L. Mucke, (2010) Amyloid-beta-induced neuronal dysfunction in Alzheimer's disease: from synapses toward neural networks. Nat Neurosci 13, 812; J. Lauren et al. (2009) Cellular prion protein mediates impairment of synaptic plasticity by amyloid-beta oligomers. Nature 457, 1128). To assess a direct contribution of PirB to this cellular correlate of AD pathology, the effects of acute Aβ42 oligomer addition were examined in WT vs PirB−/− hippocampal slices; LTP at Schaffer collateral-CA1 synapses was measured (FIG. 3, A to D). Because PirB has high affinity for Aβ oligomers (Kd=~110-180 nM; FIG. 1 and FIG. 8), slices were treated with 200 nM total peptide of oligomerized Aβ42 or with vehicle control, and field excitatory postsynaptic potentials (fEPSPs) following theta burst stimulation (TBS) were recorded. Consistent with previous reports (J. Lauren et al. (2009) Cellular prion protein mediates impairment of synaptic plasticity by amyloid-beta oligomers. Nature 457, 1128; H. W. Kessels, (2010) The prion protein as a receptor for amyloid-beta. Nature 466, E3), Aβ42 oligomers abolish LTP in hippocampal slices from WT mice (Vehicle: 134%±4% of baseline vs Aβ42 oligomer: 94%±7% of baseline; FIGS. 3, A and C). In marked contrast in PirB−/− slices, LTP remains intact even in the presence of Aβ42 oligomers (135%±5% of baseline; FIGS. 3, B and C); these effects are significantly different between WT and PirB−/− slices (FIG. 3D). Application of vehicle control in PirB−/− slices does not alter the magnitude of LTP, which is similar to WT mice (125±4% of baseline; FIGS. 3, B and C), consistent with previous observations of hippocampal LTP in PirB−/− mice (S. J. Raiker et al., (2010) Oligodendrocyte-myelin glycoprotein and Nogo negatively regulate activity-dependent synaptic plasticity. J Neurosci 30, 12432). These experiments demonstrate that the deleterious effects of Aβ oligomers on hippocampal LTP depend upon PirB. To assess if PirB contributes in vivo to cognitive deficits, APP/PS1 transgenic (Tg) mice were crossed with PirB−/− mice to generate APP/PS1 littermates with (PirB+/− Tg) or without (PirB−/− Tg) PirB. First, recognition memory was examined using two tests: novel object recognition and novel place recognition (M. Cisse et al., (2011) Reversing EphB2 depletion rescues cognitive functions in Alzheimer model. Nature 469, 47; P. L. McClean et al. (2011) The diabetes drug liraglutide prevents degenerative processes in a mouse model of Alzheimer's disease. J Neurosci 31, 6587). Impaired behaviors were observed in both tests in 9 month old PirB+/− Tg mice; however these learning and memory defects are not evident in mice lacking PirB (PirB−/− Tg) (FIGS. 3, E and F). Together these observations demonstrate that PirB contributes not only to Aβ-mediated loss of hippocampal LTP, but also to defects in recognition memory that characterize older APP/PS1 mice and are symptoms of synaptic pathology in AD.

Figure 6B:
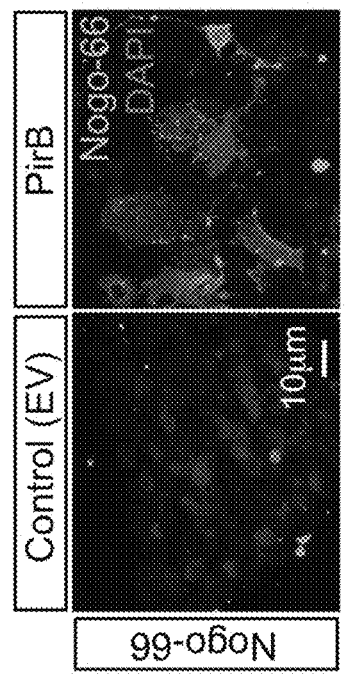
FIG. 6A-6B Nogo-66-Fc binds to PirB. HEK293 cells expressing PirB were treated with Nogo-66-Fc (100 nM) and binding was assessed by immunoprecipitation (FIG. 6A) or cell staining (FIG. 6B) for Nogo-66-Fc. These observations confirm a previously reported interaction between PirB and Nogo (J. K. Atwal et al. (2008) "PirB is a functional receptor for myelin inhibitors of axonal regeneration." Science 322, 967).
Figure 6A:
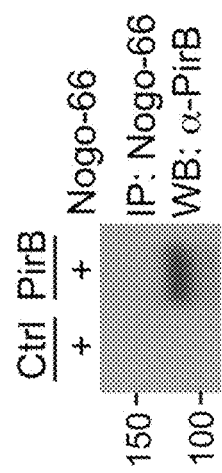
Figure 14:
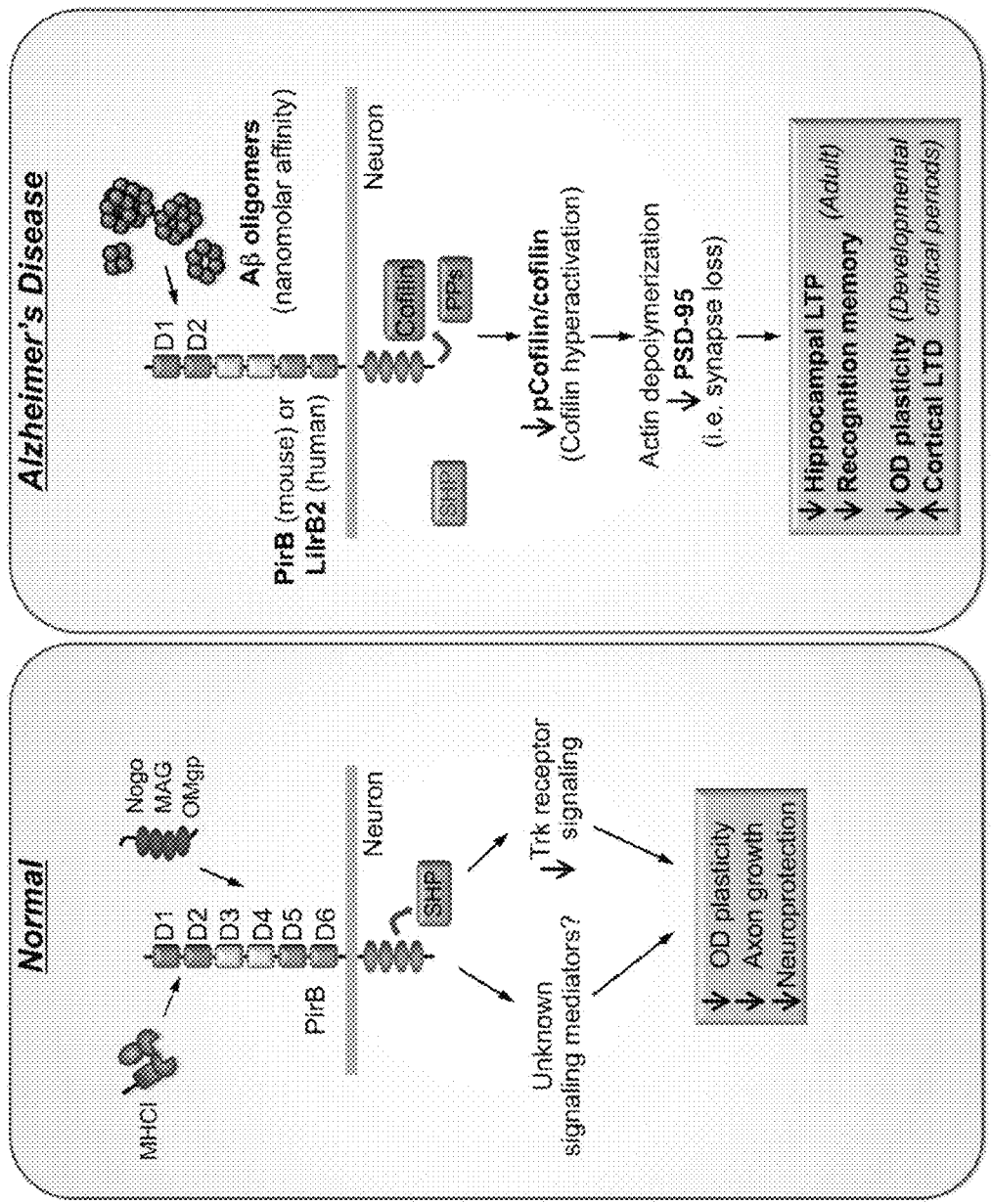
FIG. 14 provides a model for how PirB or LilrB2 might act in Alzheimer's brains. In healthy brain, PirB has been proposed to regulate OD plasticity and axon growth in response to MHCI ligands, or myelin inhibitory substrates Nogo, MAG and OMgp via alterations in SHP-1/2 and Trk signaling pathways (J. Syken, et al. (2006) "PirB restricts ocular-dominance plasticity in visual cortex." Science 313, 1795; J. K. Atwal et al. (2008) "PirB is a functional receptor for myelin inhibitors of axonal regeneration." Science 322, 967; Y. Fujita (2011) Myelin suppresses axon regeneration by PIR-B/SHP-mediated inhibition of Trk activity. Embo J 30, 1389; Y. Fujita et al. (2011) The p75 receptor mediates axon growth inhibition through an association with PIR-B. Cell Death Dis 2, e198). Here we have discovered that in Alzheimer's disease, PirB or LilrB2 engages altered downstream signaling (i.e. cofilin hyperactivation) in response to a high affinity ligand—soluble Aβ oligomers—leading to various synaptic and behavioral defects in vivo and in vitro. These observations imply that in humans upon ligation of Aβ42 oligomers, LilrB2 may engage downstream pathways similar to PirB, contributing to Alzheimer disease pathology via altered cofilin activity.

One of the earliest manifestations of pathology detected in APP/PS1 mice is impaired ocular dominance (OD) plasticity (C. M. William et al., (2012) Synaptic plasticity defect following visual deprivation in Alzheimer's disease model transgenic mice. J Neurosci 32, 8004). We evaluated OD plasticity during the developmental critical period (P22-32) by measuring the ability of one eye to expand its functional representation within visual cortex following removal of the other eye (FIG. 3G). OD plasticity is significantly diminished in APP/PS1 mice (PirB+/− Tg) (18%; FIGS. 3, H and I) (C. M. William et al., (2012), supra). When we deleted PirB, the mice (PirB−/− Tg) showed no loss in OD plasticity. In fact, PirB−/− Tg mice had OD plasticity similar to PirB−/− mice and greater than that of PirB+/− mice (FIGS. 3, H and I), consistent with previous observations (J. Syken et al. (2006), supra) and with the fact that PirB binds other ligands known to limit OD plasticity in addition to Aβ (i.e. MHCI; Nogo; FIGS. 6 and 14) (J. Syken et al. (2006). Supra; J. K. Atwal et al., (2008) PirB is a functional receptor for myelin inhibitors of axonal regeneration. Science 322, 967; A. W. McGee et al. (2005) Experience-driven plasticity of visual cortex limited by myelin and Nogo receptor. Science 309, 2222).

Cellular mechanisms associated with OD plasticity in visual cortex of juvenile APP/PS1 mice were also examined. LTD of synaptic responses in cortical layer 2/3 induced by low-frequency stimulation (LFS) of layer 4 (FIG. 11A) shares mechanisms with those that cause weakening of deprived-eye visually-driven responses after monocular deprivation (G. B. Smith, et al. (2009) Bidirectional synaptic mechanisms of ocular dominance plasticity in visual cortex. Philos Trans R Soc Lond B Biol Sci 364, 357; R. A. Crozier et al. (2007) Deprivation-induced synaptic depression by distinct mechanisms in different layers of mouse visual cortex. Proc Natl Acad Sci USA 104, 1383). The magnitude of LTD at L4 to L2/3 synapses in APP/PS1 mice is almost 3-fold greater than in non-transgenic littermates (FIGS. 11, B and C). This excessive LTD in PirB+/− Tg slices is not evident in PirB−/− Tg slices (FIG. 11, B to D). Collectively these data demonstrate that PirB function is associated not only with synaptic and cognitive alterations induced in adult mice by Aβ, but also with loss of plasticity during early development in visual cortex of APP/PS1 mice.

Figure 13:
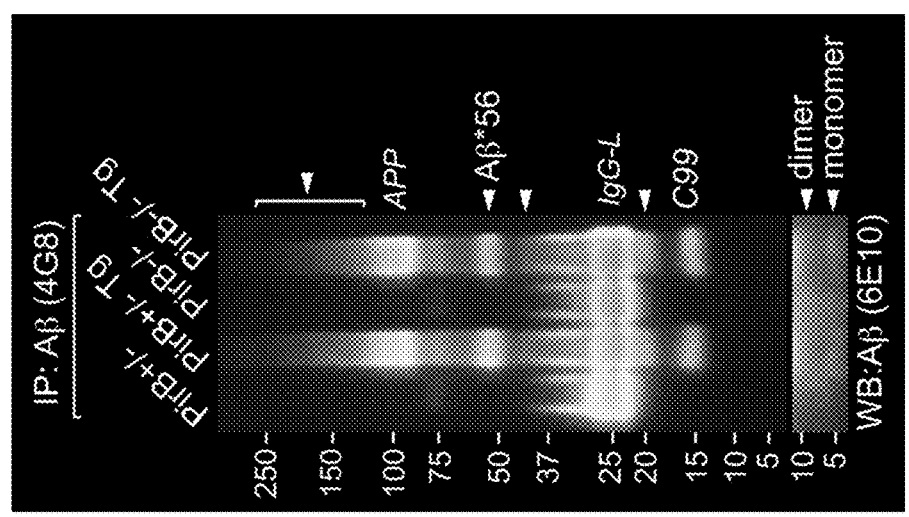
FIG. 13 demonstrates that Aβ oligomers can be detected at similar levels in APP/PS1 mice in vivo independent of PirB expression. Immunoprecipitation of Aβ from the soluble fraction of forebrain extracts detects multiple species of detergent-resistant Aβ oligomers, including previously reported 56 kDa, Aβ*56 (S. Lesne et al. (2006) A specific amyloid-beta protein assembly in the brain impairs memory. Nature 440, 352). Similar levels of oligomeric Aβ (e.g. arrowheads) as well as full-length and processed APP are detected in the forebrain of both PirB+/−; APP/PS1 (PirB+/− Tg) and PirB−/−; APP/PS1 (PirB−/−Tg) mice, indicating that APP processing or Aβ oligomerization status are not altered in the absence of PirB. Two anti-Aβ antibodies, 4G8 (detects both human and mouse Aβ17-24) and 6E10 (detects human Aβ1-16) were used. Bottom, Aβ dimer and monomer detected with longer exposure. APP, amyloid precursor protein; IgG-L, IgG light chain; C99, β-secretase cleaved 99 amino acid C-terminal fragment of APP. Representative data are shown (n=2).

Next, to identify signaling mechanisms engaged by the association of oligomeric Aβ with either PirB or LilrB2, we compared downstream signaling pathways in APP/PS1 mice with or without PirB. From an unbiased proteomic screen, we identified the actin depolymerizing factor cofilin, as well as the Ser/Thr phosphatases PP2A and PP2B/calcineurin, as potential PirB interactors. These candidates have already been implicated in Aβ-dependent synaptic loss and are engaged following induction of hippocampal LTD or LTP (G. M. Shankar et al., (2007) Natural oligomers of the Alzheimer amyloid-beta protein induce reversible synapse loss by modulating an NMDA-type glutamate receptordependent signaling pathway. J Neurosci 27, 2866; X. Wang et al., (2012) Pyruvate Prevents the Inhibition of the Long-term Potentiation Induced by Amyloid-beta through Protein Phosphatase 2A Inactivation. J Alzheimers Dis; S. Li et al., (2009) Soluble oligomers of amyloid Beta protein facilitate hippocampal long-term depression by disrupting neuronal glutamate uptake. Neuron 62, 788; H. Y. Wu et al., (2010) Amyloid beta induces the morphological neurodegenerative triad of spine loss, dendritic simplification, and neuritic dystrophies through calcineurin activation. J Neurosci 30, 2636; M. B. Rust et al., (2010) Learning, AMPA receptor mobility and synaptic plasticity depend on n-cofilin-mediated actin dynamics. Embo J 29, 1889). In forebrains of APP/PS1 (PirB+/− Tg) mice, interactions of PirB with cofilin (FIG. 4A), as well as with protein phosphatases PP2A, B or C (FIG. 12), are increased compared to non-transgenic littermates. In contrast, other PirB signaling pathways including Tyr-phosphorylation of PirB and its association with SHP-2 (J. Syken et al. (2006) PirB restricts ocular-dominance plasticity in visual cortex. Science 313, 1795; J. D. Adelson et al., (2012) Neuroprotection from stroke in the absence of MHCI or PirB. Neuron 73, 1100; Y. Fujita et al. (2011) Myelin suppresses axon regeneration by PIR-B/SHP-mediated inhibition of Trk activity. Embo J 30, 1389) are not significantly changed (FIG. 4A; lanes 1 vs 2), nor are the levels of Aβ oligomers, including previously reported Aβ*56 (S. Lesne et al., (2006) A specific amyloid-beta protein assembly in the brain impairs memory. Nature 440, 352) (56 kDa high-n oligomers) (FIG. 13; lanes 2 vs 4). Together, results indicate that the elevated interactions between PirB and cofilin/protein phosphatases in APP/PS1 mice are most likely to be caused by Aβ-PirB interactions.

PP2A and PP2B/calcineurin can activate cofilin by dephosphorylation at the Ser3 residue (P. J. Meberg, et al. (1998) Actin depolymerizing factor and cofilin phosphorylation dynamics: response to signals that regulate neurite extension. Cell Motil Cytoskeleton 39, 172; N. V. Oleinik, (2010) ALDH1 L1 inhibits cell motility via dephosphorylation of cofilin by PP1 and PP2A. Oncogene 29, 6233) and resulting actin filament disassembly appears to be crucial for Aβ oligomer-induced spine loss (9). Indeed, levels of cofilin phosphorylation at Ser3 normalized to total cofilin levels are reduced about 40% in juvenile (P30) APP/PS1 forebrains (FIGS. 4, B and D) as well as in adult (P200) hippocampal synaptosomes (FIGS. 4, C and E), which are fully restored to normal levels by knocking out PirB (FIG. 4, B to E). Cofilin activity can be decreased by LIM kinase (LIMK) 1/2, an upstream kinase that phosphorylates cofilin at Ser3 residue; no evident change was detected in LIMK1/2 activity in APP/PS1 mice with or without PirB (FIG. 4, B to E), implying that PirB and LIMK signaling may regulate cofilin independently. Addition of Aβ42 oligomers to cultures of cortical neurons also consistently triggers cofilin activation (25% reduction in cofilin phosphorylation in WT neurons after 1 hr treatment), as well as the loss of the postsynaptic protein PSD-95 (23% reduction after 24 hr treatment) (FIGS. 4, F and G). These changes do not occur in cortical neuron cultures from PirB−/− mice. Levels of cofilin phosphorylation in human Alzheimer's brains are reduced by about 38% compared to those in non-AD control brains (FIGS. 4, H and I). In AD brains, elevated Tau phosphorylation is also observed (FIG. 4H), consistent with AD diagnosis (Table 1). Thus, PirB receptor may act directly to link Aβ-induced synaptotoxicity and cofilin/protein phosphatase pathways (G. M. Shankar et al., (2007) Natural oligomers of the Alzheimer amyloid-beta protein induce reversible synapse loss by modulating an NMDA-type glutamate receptordependent signaling pathway. J Neurosci 27, 2866): Aβ oligomer-PirB binding would recruit cofilin-signaling modules to facilitate actin depolymerization, resulting in synaptic loss (indicated by reduction of PSD-95), ultimately leading to altered synaptic plasticity and cognitive deficits in APP/PS1 mice (FIG. 14). In the cerebral cortex of Alzheimer's patients, LilrB2 could engage similar cofilin-mediated downstream mechanisms.

The data above indicates that murine PirB and its human ortholog LilrB2 act as receptors for oligomeric forms of Aβ42. Mice lacking PirB are immune to the damaging effects of Aβ in hippocampal LTP and recognition memory, as well as to alterations in cofilin signaling and PSD-95 synaptic loss. This indicates that interactions between Aβ oligomers and PirB generate not only synaptotoxicity in mouse models of AD, but also early defects in developmental plasticity present in visual cortex (C. M. William et al., (2012) Synaptic plasticity defect following visual deprivation in Alzheimer's disease model transgenic mice. J Neurosci 32, 8004). The demonstration here that PirB−/− but not WT hippocampal slices are resistant to the acute effects of Aβ oligomers on LTP, and that Aβ oligomers can alter cofilin signaling in WT but not PirB−/− cortical neurons in vitro, also argues that the rescue of AD phenotypes in PirB−/− Tg mice is via direct abrogation of PirB action, rather than indirect compensation or parallel signaling pathways. We also identify in human brain LilrB2 as an Aβ receptor that may contribute to synaptic loss and cognitive impairment in Alzheimer disease progression. The results above show that via PirB, Aβ oligomers can engage signaling pathways for neuronal actin organization that lead to synapse elimination. Given this, therapies that selectively block LilrB2 function will be useful treatment of Alzheimer's disease even in the prodromal stage.

Example 2

Neural plasticity is high during developmental critical periods, then declines by adulthood. By acutely disrupting Paired immunoglobulin like receptor B (PirB) function at different ages, we show that PirB actively represses plasticity throughout life. Temporal disruption was achieved via either a conditional PirB allele or by minipump infusion of a soluble PirB ectodomain (sPirB) into mouse visual cortex. Results reveal that ocular dominance (OD) plasticity can be enhanced not only during the critical period, but also when PirB function is disrupted in adulthood. Acute blockade of PirB even after the close of the critical period also triggers formation of new functional synapses, as indicated by increases in mEPSC frequency and spine density on dendrites of layer 5 pyramidal neurons. Moreover, the profound and usually irreversible decrease in spine density typically resulting from long term monocular deprivation (LTMD) can be entirely reversed by a 1 week infusion of sPirB following the period of LTMD. These observations imply that mechanisms for enhanced structural and functional plasticity are present in adult visual cortex, but are actively repressed by PirB. By removing negative regulators such as PirB, we show that it is possible to engage these endogenous mechanisms to facilitate recovery from otherwise irreversible effects of abnormal experience during development. Similar manipulations will be useful in other situations where restoring synaptic plasticity and increasing spine density would have therapeutic value.

Materials and Methods

Mouse strains. PirB−/− and PirB flox/flox mice were generated as previously described (J. Syken et al. (2006) PirB restricts ocular-dominance plasticity in visual cortex. Science 313, 1795). A PirBWT line was maintained on the same background and used for all minipump infusion experiments performed during the critical period (P21-32). For adult minipump experiments (P63-74), PirBWT and KO mice were crossed with the Thy-1 YFP-H transgenic line (JAX #003782), which expresses YFP in a subset of layer 5 pyramidal neurons (G. Feng et al. (2000) Imaging neuronal subsets in transgenic mice expressing multiple spectral variants of GFP. Neuron 28, 41). For inducible knockout experiments, UbC-CreERT2 mice (JAX #007001) (Y. Ruzankina et al., (2007) Deletion of the developmentally essential gene ATR in adult mice leads to age-related phenotypes and stem cell loss. Cell Stem Cell 1, 113) were bred with PirB flox mice to generate UbC-CreERT2; PirB flox/flox mice and PirB flox/flox littermates. For conditional knockout experiments, CamKIIa-Cre; PirB flox/+ mice (J. Z. Tsien (1998) Behavioral genetics: subregion- and cell type-restricted gene knockout in mouse brain. Pathol Biol (Paris) 46, 699) were bred with PirB flox/+ mice to generate CamKIIa-Cre; PirB flox/flox mice and CamKIIa-Cre; PirB+/+ littermates. CamKIIa-Cre mice were also bred with Ai14 TdTomato reporter mice (N. Ramanan et al. (2005) SRF mediates activity-induced gene expression and synaptic plasticity but not neuronal viability. Nat Neurosci 8, 759). All experiments were performed blind to genotype and/or treatment, and in accordance with protocols approved by Stanford University Animal Care and Use Committee in keeping with the National Institutes of Health's Guide for the Care and Use of Laboratory Animals.

Tamoxifen injections. Tamoxifen free base (Sigma T5648) was dissolved at 20 mg/mL in a mixture of 2% ethanol in corn oil (Sigma C8267), and stored in aliquots at −20° C. For juvenile mice, 7 mg of tamoxifen was injected intraperitoneally into the mother daily when the pups were P3-P7. For adult mice, 4 mg of tamoxifen were injected daily when mice were P45-49.

PCR Genotyping. Samples from mouse cortex were lysed and genomic DNA extracted using the DNEasy Blood and Tissue Kit (Qiagen). Excision of PirB was detected using primers flanking the floxed region of PirB with sequences ctgccctcatgtcttaactt (SEQ ID NO:27) and gagaatcaccagaca-catgc (SEQ ID NO:28). Samples were run on a 1.5% agarose gel in TAE buffer, and visualized with ethidium bromide.

Western Blotting for PirB. Mice were anesthetized with isoflurane, decapitated, and forebrains (cortex and hippocampus) were removed and placed in ice-cold lysis buffer (50 mM Tris, pH 7.4, 150 mM NaCl, 1% NP-40) with protease inhibitor cocktail (Sigma P8340-1 ML). Samples were centrifuged to remove cellular debris, and then incubated overnight at 4° C. with anti-PirB 6C1 (BD Biosciences BDB550348). Immunoprecipitate was collected on Protein G beads and liberated by incubation at 85° C. for 5 minutes. Samples were loaded in a 7.5% bis-acrylamide gel and blotted with a 1:1000 dilution of a rabbit antibody raised against the floxed region of PirB. Semi-quantitative densitometry was performed using ImageJ software. Normalized values were then compared with Mann-Whitney U tests. For PirB phosphorylation studies, cortical tissue samples posterior to the infusion site were lysed and pooled together (4 animals/prep), then incubated overnight with anti-phospho-tyrosine-conjugated beads (Cell Signaling 9419S). Immunoprecipitate was collected by centrifugation, then liberated, loaded and blotted against PirB as described above.

sPirB Immunohistochemistry. Brains were snap-frozen in M1 mounting media (Shandon), and sectioned at 16 μm on a cryostat. Sections were fixed in 4% paraformaldehyde in 0.1 M PBS for 30 minutes, washed with PBS, and then blocked in 10% goat serum, 0.3% Triton-X for 1 hour. Sections were incubated overnight at 4° C. with anti-Myc mouse monoclonal 4A6 (Millipore 05-724) at a 1:500 dilution in 2% goat serum and 0.1% Triton-X, then washed, and incubated at room temperature for 1 hour with goat anti-mouse secondary antibody conjugated to alkaline phosphatase (Jackson Immunoresearch 115-055-062) at a 1:1000 dilution in 1% goat serum. Staining was visualized using the colorimetric NBT/BCIP substrate (Roche 11681451001).

sPirB Protein Production. To create a soluble PirB mimic, the PirB ectodomain was cloned into a plasmid containing a His tag for purification and a Myc tag for antibody detection, with a sequence identical to previous publications (J. Syken et al. (2006) PirB restricts ocular-dominance plasticity in visual cortex. Science 313, 1795; J. K. Atwal et al., (2008) PirB is a Functional Receptor for Myelin Inhibitors of Axonal Regeneration. Science 322, 967; H. Matsushita et al. (2011) Differential but competitive binding of Nogo protein and class I major histocompatibility complex (MHCI) to the PIR-B ectodomain provides an inhibition of cells. J Biol Chem 286, 25739). HEK 293 cells were transfected using Lipofectamine 2000 (Invitrogen) with a plasmid containing PirB-Myc-His or a control plasmid containing Alkaline Phosphatase-Myc-His. Conditioned media was collected, concentrated with a 50 kDa exclusion column (Millipore), and purified using a HisSpin Trap column (GE Healthcare). Western blots were performed using anti-Myc mouse monoclonal 9E10 (Developmental Studies Hybridoma Bank, Iowa, 9E10), and a polyclonal goat anti-PirB antibody (R&D Systems #AF2754) directed against the extracellular domain. Subsequently, Invitrogen Custom Services produced PirB-Myc-His in FreeStyle HEK 293 cells and purified it on a nickel column. Aliquots of this commercially produced protein were also assayed for quality with western blotting as described above—results were identical to those shown in FIG. 18B.

Monocular deprivation or enucleation. For monocular enucleation (ME), mice were anesthetized with 1-2.5% isoflurane, one eye was removed and a drop of Vetbond (3M) was placed on eyelids to prevent reopening. Monocular deprivation (MD) was performed on juvenile (P19) mice for 4 weeks. Mice were anesthetized using isoflurane gas anesthesia (~1.5-2%). Hair near the eyelid was trimmed, the lid margin was surgically removed and a small drop of ophthalmic cream (Isopto-Max, Alcon Pharma GmbH, or Vetropolycin HC, Pharmaderm Animal Health, NY) was applied to the eye. The eyelid was sutured with 2 to 3 mattress stitches using 6-0 silk (Ethicon). Eye reopening was carried out at P47 under isoflurane anesthesia. The reopened eye was covered with ophthalmic cream again to prevent corneal damage, and was inspected daily to ensure that it did not re-close.

Arc mRNA induction and in situ hybridization. As described (Y. Tagawa et al. (2005) Multiple periods of functional ocular dominance plasticity in mouse visual cortex. Nat Neurosci 8, 380), ME was performed shortly before Arc induction unless it had previously occurred as part of an OD plasticity experiment. Mouse cages were placed overnight in total darkness (16-18 hr), then the cage was brightly illuminated for 30 minutes to permit vision through the open eye prior to euthanasia via isoflurane anesthesia and decapitation. Brains were removed rapidly and flash-frozen in M-1 mounting medium (Shandon, Thermo Scientific). Sections including visual cortex were cut on a cryostat (16 μm) in the coronal plane and collected on Superfrost slides (Fisher Scientific) for subsequent in situ hybridization. A digoxigenin-labeled Arc antisense mRNA probe was generated from a pBS-Arc plasmid (G. L. Lyford et al. (1995) Arc, a growth factor and activity-regulated gene, encodes a novel cytoskeleton-associated protein that is enriched in neuronal dendrites. Neuron 14, 433) using T7 RNA polymerase, and in situ hybridizations were performed as described previously (J. Syken et al. (2006), supra; Y. Tagawa et al. (2005), supra; C. M. William et al. (2012) Synaptic plasticity defect following visual deprivation in Alzheimer's disease model transgenic mice. J Neurosci 32, 8004; A. Datwani et al. (2009) Classical MHCI molecules regulate retinogeniculate refinement and limit ocular dominance plasticity. Neuron 64, 463; M. Djurisic et al. (2013) PirB regulates a structural substrate for cortical plasticity. Proc Natl Acad Sci USA 110, 20771). Probe was detected using a sheep anti-digoxigenen polyclonal antibody conjugated to alkaline phosphatase (Roche 11093274910), and visualized using the colorimetric NBT/BCIP substrate (Roche 11681451001). Images were acquired via brightfield microscopy at 2× magnification, and analyzed using the Line Scan function of NeuroLens software (Rick Hoge, McGill University, Montreal, Canada; neurolens.org). The software was used to measure intensity through the Arc signal in layer 4 of visual cortex ipsilateral to the open (nondeprived) eye and a linear background model was subtracted out, allowing for quantitative measurement of the width of cortical territory functionally activated by the ipsilateral eye. Approximately 6-8 sections containing visual cortex were scanned and averaged per animal, yielding one data point per individual. Data acquisition and analyses were performed blind to genotype and/or treatment regime.

Osmotic Minipump implantations and sPirB infusion. Minipumps (Alzet model 1002; 0.25 μL/hr, 100 μL capacity) were filled the night before surgery and stored in 0.9% saline at 37° C. before implantation. Mice were anesthetized with 1-2.5% isoflurane and positioned on a stereotaxic frame (Kopf). A scalp incision exposed the cranium, and coordinates were zeroed at bregma and lambda to ensure the skull was flat. After a craniotomy, a custom minipump cannula (Plastics One, Roanoke, Va.) with a beveled 30-gauge needle and containing either 1 mg/mL PirBMyc-His, or 1 mg/mL Bovine Serum Albumin (BSA, VWR EM-2930) was implanted. To minimize damage, the minipump cannula was inserted just anterior to visual cortex (2.5 mm lateral and 3 mm posterior to bregma), with the needle bevel facing posterior and its opening located 1 mm below the skull surface, to direct sPirB into visual cortex (FIG. 21A). The cannula base was secured to the skull with Loctite 454 cyanoacrylate glue (Henkel, Westlake, Ohio). The minipump was attached to the cannula via plastic tubing and placed subcutaneously between the scapulae. Minipumps contained either 1 mg/mL PirB-Myc-His, or 1 mg/mL Bovine Serum Albumin (BSA, VWR EM-2930) in 0.1 M phosphate buffered saline (PBS). All experiments involved littermate controls and were performed blind to genotype and/or treatment.

Dendritic Spine Analysis. After minipump infusion, mice were deeply anaesthetized with isoflurane, and the brain was fixed by transcardial perfusion of 0.1 M phosphate buffered saline, followed by 4% paraformaldehyde in PBS. 150 μm thick coronal sections were cut on a vibratome (Leica), mounted on slides with Prolong Gold with DAPI (Invitrogen) and imaged using two-photon laser scanning microscopy (Prairie Technologies, Middleton, Wis.). YFP labeled pyramidal somata were anatomically localized to layer 5 in the binocular zone of the visual cortex using a 10× objective, then imaged using a 60× coverslip-corrected water immersion objective (Olympus, NA 1.2) and 4× optical zoom. For apical tuft spines, each L5 cell's apical dendrite was traced to the first branch point in layer 2/3, and z-stacks were acquired of as much dendritic arbor as was visible in the section (at least 100 μm). For basolateral dendrites, z-stacks were acquired for a single dendrite per cell, again with a minimum length of 100 μm. Spine density was measured in Fiji, a build of ImageJ software (www.fiji.sc), using the Cell Counter (Kurt De Vos) and Simple Neurite Tracer (Mark Longair) plugins to count spines and measure dendritic length. All analysis was performed blind to treatment.

Electrophysiology. After brief intracardial perfusion of ice-cold ACSF (in mM; 125 NaCl, 26 NaHCO3, 2.3 KCl, 1.26 KH2PO4, 1.3 MgCl2, 2.5 CaCl2, and 10 glucose, aerated with 95% O2/5% CO2) brains from P60-70 mice were removed and coronal sections (400 μm) including visual cortex were made using a vibratome (Leica VT1000S) in ice-cold NMDG solution (in mM: 135 NMDG, 1 KCl, 1.2 KH2PO4, 1.5 MgCl2, 0.5 CaCl2, 20 choline bicarbonate, and 10 glucose). Sections were transferred to a recovery chamber containing 37° C. ACSF for 30 min, then at room temperature for 30 min before recordings. All recordings were done at 30-32° C. in a chamber with constant ACSF flow.

Whole-cell patch clamp recordings were performed from pyramidal neurons in layer 5 of visual cortex. The recording pipette (2~4 MΩ) contained Cs+-based internal solution (in mM: 105 CsCl, 20 TEA-Cl, 2 MgCl2, 1 EGTA, 10 HEPES, 3 Mg-ATP, 15 Phosphocreatine, 1 Na-GTP, 5 QX-314, pH 7.4, 280 mOsm). Miniature excitatory postsynaptic currents (mEPSCs) were isolated by applying TTX (1 μM, Sigma), SR95531 (20 μM; Tocris, Mo.) to block GABA-A receptors and APV (100 μM; Tocris, Mo.) to block NMDA receptors. Synaptic responses were recorded using an Axopatch 200B amplifier (Molecular Devices, CA), digitized using Digidata 1322A (Axon Instruments, CA) and data acquisition was performed by Clampex 9.2 (Axon Instruments, CA). Data analysis was conducted using MiniAnalysis software (ver. 6.0.7) (Synaptosoft).

Statistical Analyses. All statistical analyses were performed with Prism software (Graphpad). When only two groups were involved, two-sample t-tests were used, with Welch's correction for unequal variances applied where appropriate. Data for which a normal distribution could not be assumed was analyzed with Mann-Whitney U tests. In cases of 3 or more groups, a one-way ANOVA was conducted, with Tukey post-hoc tests for individual pairs of columns.

Results

During postnatal development, the capacity of the brain to undergo experience-dependent changes in synaptic strength and circuit connectivity is dynamically regulated, with plasticity peaking during developmental critical periods, and then decreasing as the brain matures (D. H. Hubel, T. N. Wiese) (1970) The period of susceptibility to the physiological effects of unilateral eye closure in kittens. The Journal of Physiology 206, 419; E. I. Knudsen, (2004) Sensitive periods in the development of the brain and behavior. J Cogn Neurosci 16, 1412; C. N. Levelt, M. Hubener, (2012) Critical-period plasticity in the visual cortex. Annu Rev Neurosci 35, 309). Critical periods represent key times when sensory experience is necessary for normal circuit development, and when abnormal experience can generate enduring changes in brain structure and function (E. I. Knudsen, (2004), supra; T. Pizzorusso et al., (2006) Structural and functional recovery from early monocular deprivation in adult rats. Proc Natl Acad Sci USA 103, 8517). Ocular dominance (OD) plasticity is a graphic example of experience-driven synaptic and circuit plasticity. Following a brief period of monocular visual deprivation (MD) or enucleation (ME) during juvenile life, visually-driven responses of neurons in the binocular zone of mammalian primary visual cortex (V1) shift towards the open eye, and cortical territory containing neurons responding to open eye stimulation expands (C. N. Levelt, M. Hubener, (2012), supra; J. A. Gordon, M. P. Stryker, (1996) Experience-dependent plasticity of binocular responses in the primary visual cortex of the mouse. J Neurosci 16, 3274; Y. Tagawa et al. (2005) Multiple periods of functional ocular dominance plasticity in mouse visual cortex. Nat Neurosci 8, 380).

These deprivation effects peak around postnatal day 28 (P28) in mouse, and decrease thereafter, so that by adulthood little if any OD plasticity resulting from eye closure can be detected (J. A. Gordon, M. P. Stryker, (1996), supra; Y. Tagawa et al. (2005), supra). Furthermore, a long term period of MD (LTMD) spanning the entire critical period (e.g. P19-47) causes an enduring loss of visual acuity and functional input from the deprived eye even if binocular vision is restored in adulthood (T. Pizzorusso et al. (2006), supra; H. Y. He et al. (2007) Experience-dependent recovery of vision following chronic deprivation amblyopia. Nat Neurosci 10, 1134; E. Kang et al., (2013) Visual acuity development and plasticity in the absence of sensory experience. J Neurosci 33, 17789). The normal decrease in plasticity by adulthood, while important for stabilizing neural circuits, also may act as a barrier to recovery, limiting cortical reorganization after injury, locking in effects of dysfunctional development, and even opposing acquisition of new learning. If it were possible to restore adult neural circuits to a more immature state, effectively re-opening critical periods, it might be possible to recover function after nervous system damage, to treat neurodegenerative or developmental disorders, or even to enhance learning in healthy individuals.

A limited number of candidate molecules that appear to act as endogenous negative regulators of cortical plasticity have been identified. Here we examine if it is possible to restore critical period-like plasticity to adult visual cortex by acutely manipulating the function of PirB at specific postnatal ages, including adulthood.

Figure 15A:
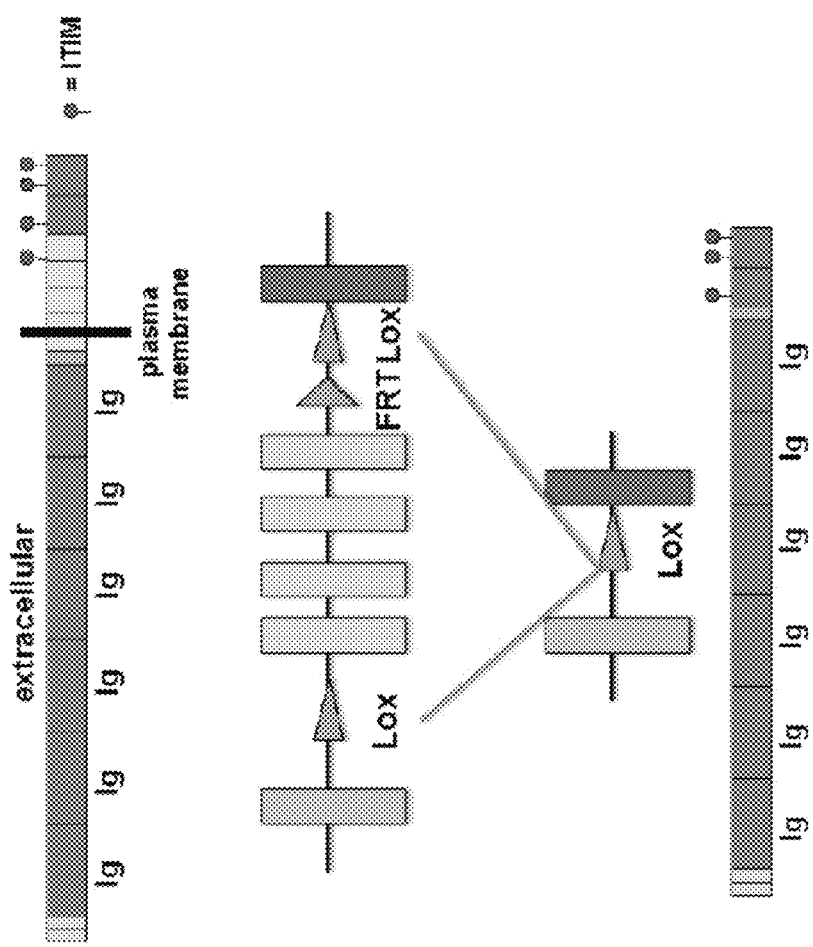

Genetic deletion of PirB conditional allele enhances OD plasticity. To disrupt PirB function with temporal control, a conditional allele of PirB was generated by inserting loxP sites surrounding exons 10-13, containing the transmembrane domain and first ITIM domain of PirB (FIG. 15A). To obtain robust widespread deletion, this PirB flox line was crossed with a transgenic line expressing tamoxifen-inducible Cre-ERT2 on a Ubiquitin C promoter (Y. Ruzankina et al., (2007) Deletion of the developmentally essential gene ATR in adult mice leads to age-related phenotypes and stem cell loss. Cell Stem Cell 1, 113). The resulting Ubc-Cre-ERT2; PirB flox/flox mice were bred with PirB flox/flox mice, producing both experimental Ubc-CreERT2; PirB flox/flox animals (henceforth called Cre+) and PirB flox/flox (Cre−) littermate controls. Tamoxifen injections given either neonatally or after critical period closure induced robust deletion of the floxed allele from genomic DNA within one week (FIG. 15B). PirB protein loss is more gradual; for example, daily tamoxifen from P3-P7 diminishes protein in forebrain by ~90% by P27 (FIG. 15C, D). Similar gradual loss of protein is seen at P70 following tamoxifen from P45-49 (FIG. 15C, E). Thus tamoxifen administration can substantially reduce PirB protein by the peak of the OD critical period at P28 (J. A. Gordon, M. P. Stryker, (1996) Experience-dependent plasticity of binocular responses in the primary visual cortex of the mouse. J Neurosci 16, 3274), as well as in adulthood by P70.

To assess if OD plasticity during the critical period is increased following acute postnatal removal of PirB, mice received ME from P28-32 (FIG. 16A-D). Then at P32 Arc mRNA induction was used to assess the extent to which the functional representation of the spared eye has expanded within visual cortex (Y. Tagawa et al. (2005) Multiple periods of functional ocular dominance plasticity in mouse visual cortex. Nat Neurosci 8, 380). The horizontal extent of Arc mRNA in situ hybridization signal in layer 4 of visual cortex ipsilateral to the spared eye was measured. This expansion in width of Arc mRNA signal is a measure of open eye strengthening following visual deprivation and is known to correlate well with OD plasticity measurements obtained using electrophysiological methods and intrinsic signal imaging (Y. Tagawa et al. (2005), supra; M. Djurisic et al., (2013) PirB regulates a structural substrate for cortical plasticity. Proc Natl Acad Sci USA 110, 20771; P. O. Kanold et al. (2009) Co-regulation of ocular dominance plasticity and NMDA receptor subunit expression in glutamic acid decarboxylase-65 knock-out mice. The Journal of Physiology 587, 2857; C. M. William et al., (2012) Synaptic plasticity defect following visual deprivation in Alzheimer's disease model transgenic mice. J Neurosci 32, 8004). As expected during the critical period, 4 days of ME in either Cre+ or Cre− mice generates substantial expansion in width of Arc mRNA signal as compared to normally reared controls (FIG. 16B-D). However, in mice lacking PirB (Cre+), the open-eye representation expands 21% more than in control (Cre−) littermates, while in normally-reared mice, there is no difference between genotypes in width of Arc mRNA signal induced by stimulation of the ipsilateral eye (FIG. 16D). To facilitate comparisons between genotypes, a plasticity index was calculated by normalizing the width of Arc mRNA induction following ME to the normally reared value for each genotype. The plasticity index in Cre+ mice is 23% higher than in Cre− mice (FIG. 20A), consistent with the fact that PirB is absent. These observations imply that PirB need not act only early in fetal life, but rather actively represses OD plasticity during the critical period.

Figures 16E, 16F, 16G, 16H:
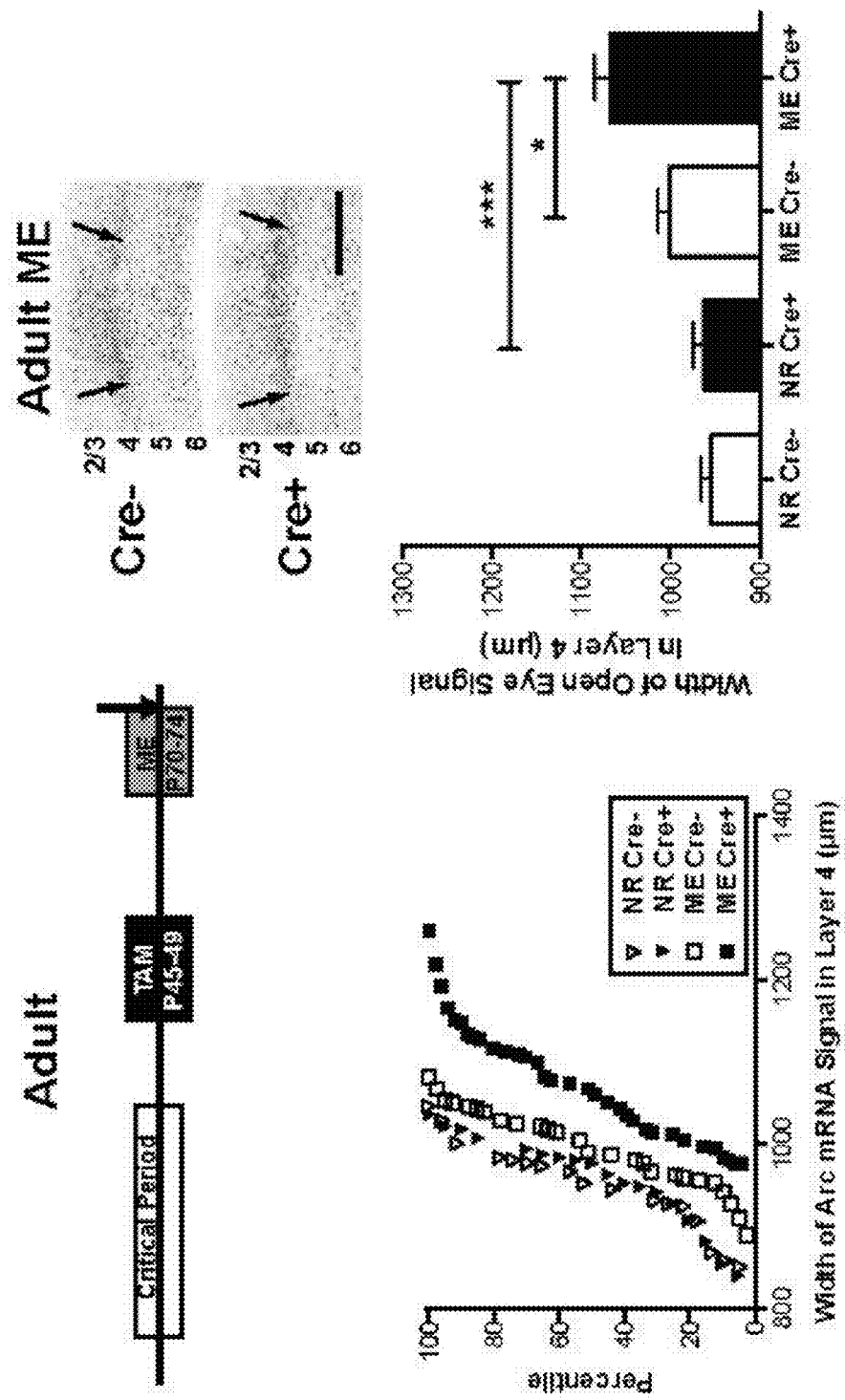

In developing WT animals, OD plasticity decreases around P35-40 (the end of the critical period), and 4 days of monocular deprivation or enucleation thereafter has little or no effect (J. A. Gordon, M. P. Stryker, (1996) Experience-dependent plasticity of binocular responses in the primary visual cortex of the mouse. J Neurosci 16, 3274; Y. Tagawa et al. (2005) Multiple periods of functional ocular dominance plasticity in mouse visual cortex. Nat Neurosci 8, 380; K. Lehmann, S. Lowel, Age-dependent ocular dominance plasticity in adult mice. PLoS One 3, e3120). To determine if targeting PirB function might enhance plasticity later in life, tamoxifen was administered from P45-49 (FIG. 16E), resulting in almost complete loss of PirB protein by P70 (FIG. 15C, E). Then these adult mice received ME from P70-74, weeks after the critical period would normally have closed. As with juvenile mice, at P74 there is no significant difference in baseline width of Arc mRNA signal between genotypes in normally reared controls (FIG. 16G, H). There was also no significant difference (p=0.18) in width of Arc mRNA signal following ME from P70-74 in Cre− controls. However, a significant expansion of open-eye representation (p=0.0004) was observed in Cre+ mice with 4 day ME (FIG.

16G, H; FIG. 20B). While the magnitude of OD plasticity in this experiment is reduced across all genotypes as compared with that seen during the critical period, deletion of PirB in adults is still sufficient to enhance OD plasticity and to cause a significant expansion in open eye representation not observed in adult littermate controls.

Figure 17A:
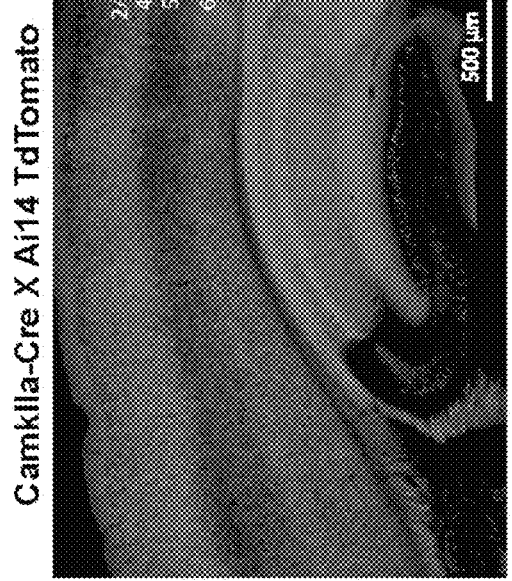
FIG. 17A-17C shows that Cre-mediated deletion of PirB from forebrain excitatory neurons is sufficient to enhance adult OD plasticity.
Figure 17B:
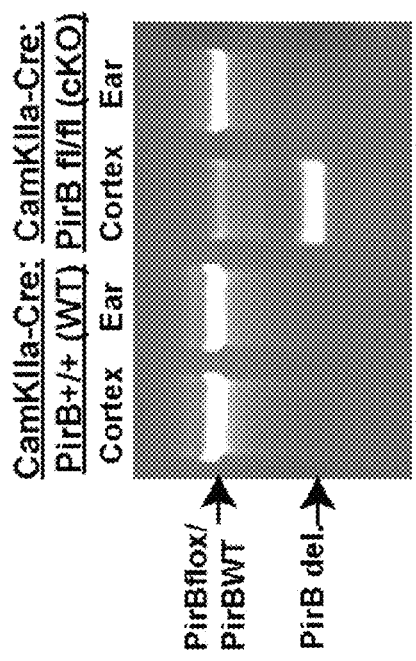

Postnatal deletion of PirB from excitatory neurons is sufficient to enhance adult OD plasticity. In the experiments above, a ubiquitously expressed Cre recombinase was used to achieve robust deletion of PirB in all cells. Next, we investigated if loss of PirB specifically in forebrain excitatory neurons is sufficient to enhance OD plasticity. PirB flox/flox mice were crossed with a CamKIIa-Cre line, which expresses Cre exclusively in forebrain excitatory neurons (J. Z. Tsien et al. (1996) Subregion- and cell type-restricted gene knockout in mouse brain. Cell 87, 1317; N. Ramanan et al. (2005) SRF mediates activity-induced gene expression and synaptic plasticity but not neuronal viability. Nat Neurosci 8, 759), generating CamKIIa-Cre; PirB flox/flox conditional knockouts, and CamKIIa-Cre; PirB+/+ littermate controls. PCR genotyping of brain and ear from these two genotypes confirms brain specific deletion of the floxed region of PirB (FIG. 17A). To confirm the spatial pattern of Cre deletion, CamKIIa-Cre mice were also crossed with the Ai14 TdTomato reporter line (L. Madisen et al., A robust and high-throughput Cre reporting and characterization system for the whole mouse brain. Nat Neurosci 13, 133). Results show faithful Cre activity at P30 in the pyramidal neurons of hippocampus and cortex (FIG. 17B). Prior studies have shown that excision of floxed regions of DNA in this Cre line is gradual, with complete deletion occurring around 3 months of age (N. Ramanan et al. (2005) SRF mediates activity-induced gene expression and synaptic plasticity but not neuronal viability. Nat Neurosci 8, 759), permitting us to examine effects of PirB deletion in adulthood.

Figure 17C:
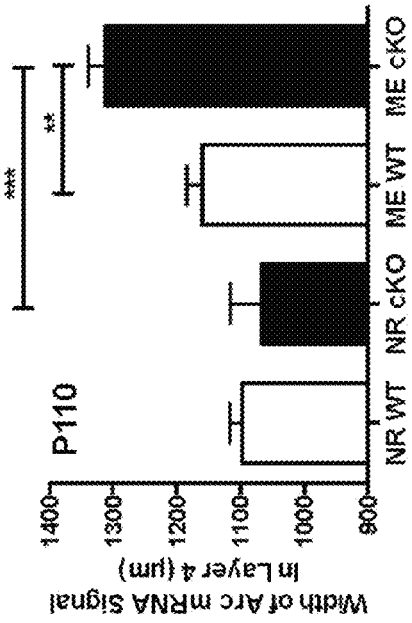

CamKIIa-Cre; PirB flox/flox conditional knockouts, and CamKIIa-Cre; PirB+/+ littermate controls received 10 days ME from P100-110, followed by assessment of OD plasticity. Open eye expansion in visual cortex in CamKIIa conditional knockout mice is ~13% greater than in littermate controls (FIG. 17C; FIG. 20), indicating that postnatal deletion of PirB from excitatory neurons is sufficient to increase OD plasticity by P110. Furthermore, this increase is similar in magnitude to prior observations of enhanced OD plasticity in adult mice with germline deletion of PirB, indicating that loss of PirB function in excitatory neurons may be largely responsible for the observed PirB−/− phenotype.

Rapid enhancement of OD plasticity by pharmacological blockade of PirB ligand binding. The genetic approaches used above excise PirB from the genome but the ensuing loss of PirB protein is gradual and widespread. To achieve a rapid and local disruption of PirB function within visual cortex, a molecular pharmacological approach was employed. A soluble PirB ectodomain (sPirB) protein labeled with His and Myc tags for purification and detection was generated (FIG. 18A). Soluble ectodomains of receptors and other proteins have been used routinely in experimental and therapeutic contexts to disrupt endogenous ligand binding (S. Davis et al., (1994) Ligands for EPH-related receptor tyrosine kinases that require membrane attachment or clustering for activity. Science 266, 816; R. J. Cabelli et al. (1997) Blockade of endogenous ligands of trkB inhibits formation of ocular dominance columns. Neuron 19, 63; J. Holash et al., (2002) VEGF-Trap: a VEGF blocker with potent antitumor effects. Proc Natl Acad Sci USA 99, 11393); in the case of PirB these ligands include MHC Class I proteins (J. Syken et al. (2006) PirB restricts ocular-dominance plasticity in visual cortex. Science 313, 1795; A. Maeda, et al. (1998) Requirement of SH2-containing protein tyrosine phosphatases SHP-1 and SHP-2 for paired immunoglobulin-like receptor B (PIR-B)-mediated inhibitory signal. J Exp Med 187, 1355; H. Matsushita et al. (2011) Differential but competitive binding of Nogo protein and class I major histocompatibility complex (MHCI) to the PIR-B ectodomain provides an inhibition of cells. J Biol Chem 286, 25739). Amyloid Beta oligomers (example 1 above), and NogoA peptide (J. K. Atwal et al., (2008) PirB is a Functional Receptor for Myelin Inhibitors of Axonal Regeneration. Science 322, 967; H. Matsushita et al. (2011) Differential but competitive binding of Nogo protein and class I major histocompatibility complex (MHCI) to the PIR-B ectodomain provides an inhibition of cells. J Biol Chem 286, 25739). When a plasmid coding for sPirB is transfected into HEK293 cells, the recombinant protein is secreted into culture supernatant, and can be detected via western blotting against both the Myc tag and the PirB ectodomain (FIG. 18B).

Next, sPirB was infused into visual cortex (V1) of WT mice via osmotic minipumps. To assess efficacy of sPirB infusions, minipumps were implanted at P21. 7 days later cortical tissue was harvested posterior to the implantation site in the infused and contralateral hemispheres, as well as in uninfused littermates. PirB phosphorylation is noticeably decreased in visual cortex posterior to the infusion site as compared both to the contralateral hemisphere and to untreated littermate control hemispheres (FIG. 18C). 11 days after implantation, extensive diffusion of sPirB can be detected via anti-Myc immunostaining of sections (FIG. 18D) across visual cortex as far as 2 mm posterior to the infusion site (FIG. 21B); no anti-Myc staining can be detected in BSA-infused control brains (FIG. 21C).

Figures 20D, 20E:
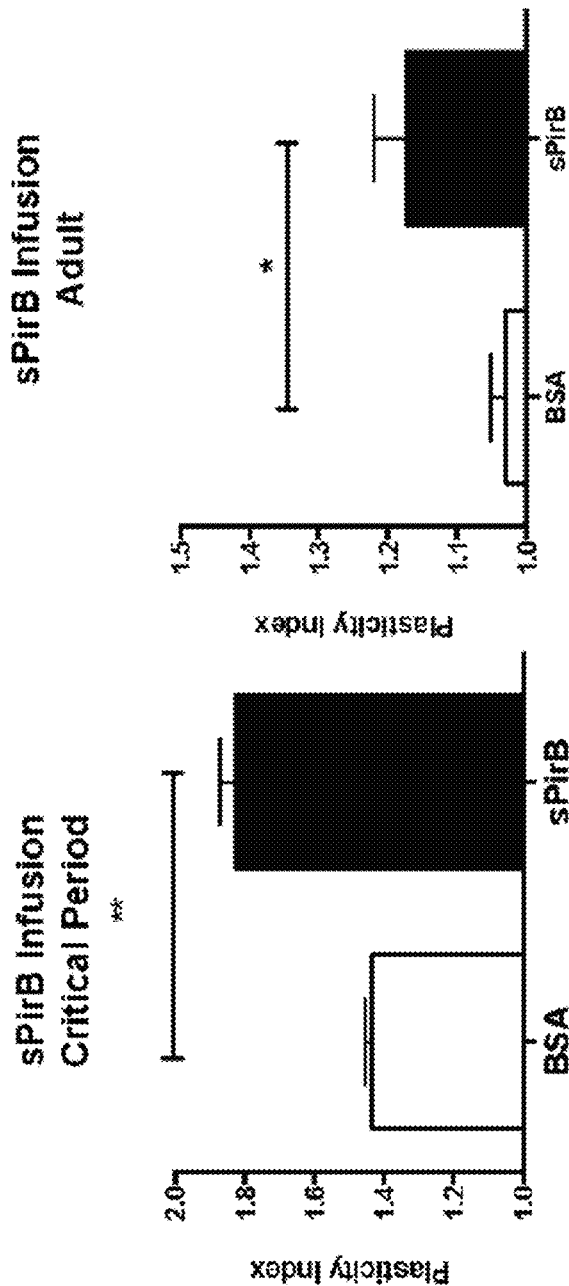

Minipump infusion of sPirB into visual cortex of WT mice for 11 days during the critical period (P21-32), combined with 4 days of ME from P28-32, results in a very pronounced expansion in width of visual cortex containing neurons functionally driven by the open (ipsilateral) eye, as assessed with Arc mRNA induction (FIG. 18E). By this measure, OD plasticity is 24% greater with sPirB infusion than in controls infused with an equivalent concentration of BSA (FIG. 18F; FIG. 20D). Because the infusion is local and limited to an 11 day period beginning at the onset of the critical period (J. A. Gordon, M. P. Stryker, (1996) Experience-dependent plasticity of binocular responses in the primary visual cortex of the mouse. J Neurosci 16, 3274; Y. Tagawa et al. (2005) Multiple periods of functional ocular dominance plasticity in mouse visual cortex. Nat Neurosci 8, 380), the results of this experiment make it possible to narrow considerably the spatiotemporal window in which PirB may act to suppress plasticity. Taken together with the tamoxifen-inducible PirB knockout results presented above, these data indicate that PirB actively suppresses plasticity locally in visual cortex during the critical period for OD plasticity.

Remarkably, substantial OD plasticity can also be restored to the visual cortex of adult WT mice after minipump infusions of sPirB between P63-74. ME from P70-74 in the presence of sPirB, but not BSA, causes a 12.5% expansion in the functional representation of the open eye (FIG. 18G, H; FIG. 20E). This expansion is twice as large as that in tamoxifen-driven PirB excision in adult mice (cf FIG. 16H). In contrast, there is no significant effect of 11-day minipump infusions of either BSA or sPirB on OD plasticity in mice reared with normal vision, as assessed by measuring open eye expansion (FIG. 18H).

Figure 22A:
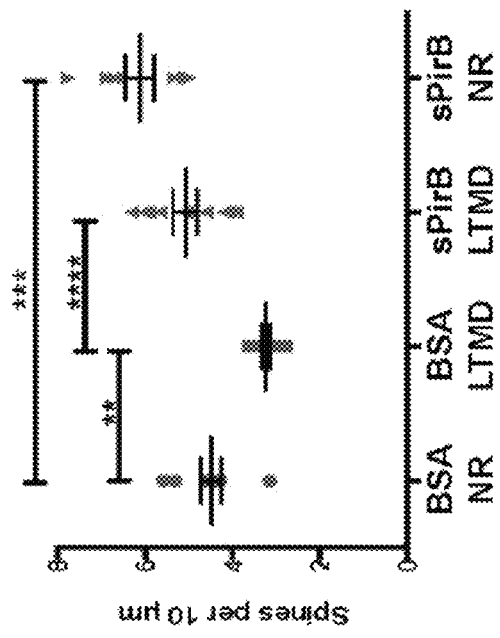
FIG. 22A-22D illustrates the effect of minipump infusions of sPirB or BSA on dendritic spines by cells and by spine type.
Figure 22B:
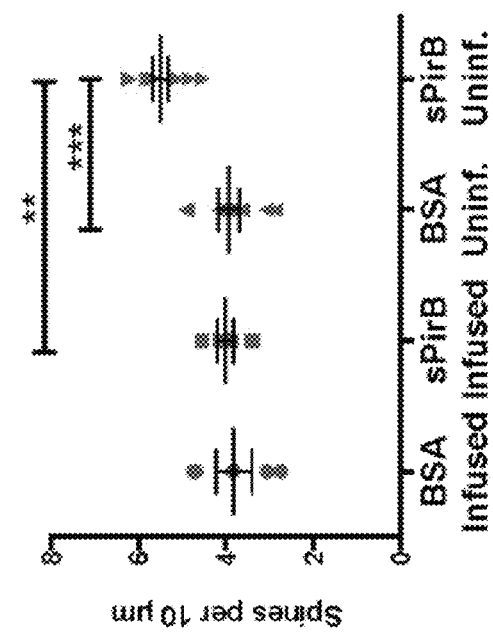
Figure 22C:
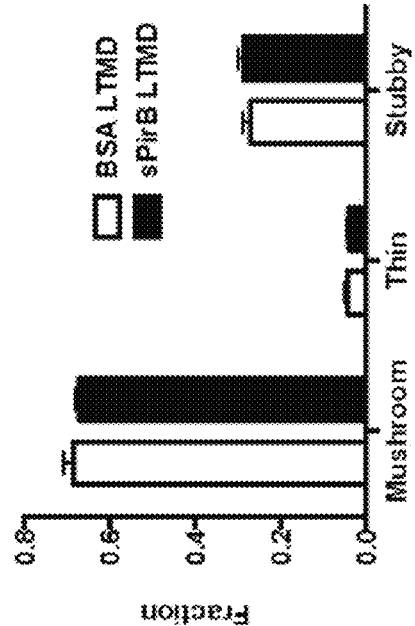

PirB binds multiple ligands (J. K. Atwal et al., (2008) PirB is a Functional Receptor for Myelin Inhibitors of Axonal Regeneration. Science 322, 967; H. Matsushita et al. (2011) Differential but competitive binding of Nogo protein and class I major histocompatibility complex (MHCI) to the PIR-B ectodomain provides an inhibition of cells. J Biol Chem 286, 25739), which themselves can bind to other receptors (J. K. Atwal et al., (2008), supra; H. Matsushita et al. (2011), supra), possibly accounting for the observation that sPirB has a larger effect on OD plasticity than genetically induced deletion of PirB. To test this hypothesis, sPirB or BSA was infused via minipumps into adult germ-line PirB−/− mice, which also received 4 day ME (P70-74). Germline PirB−/− mice implanted with BSA minipumps experienced the expected increase in OD plasticity as compared to WT receiving BSA (FIG. 18H, 18I; p=0.03). However, there was no additional effect of sPirB infusion compared to BSA infusion in PirB−/− mice (FIG. 18I). This lack of effect of sPirB infusion in adult PirB−/− visual cortex indicates that endogenous PirB is not only required to enhance OD plasticity, but also that the pharmacological blockade is PirB-specific. Together with results from the tamoxifen-inducible PirB mice, these findings indicate that acute, specific manipulations that delete or block PirB function are sufficient to enhance OD plasticity even well beyond the end of the critical period.

sPirB infusion increases synaptic density on L5 pyramidal neurons. Recent studies have shown that sensory experience as well as motor learning causes a lasting increase in dendritic spine density on cortical pyramidal neurons (G. Yang, et al. (2009) Stably maintained dendritic spines are associated with lifelong memories. Nature 462, 920; T. Xu et al., (2009) Rapid formation and selective stabilization of synapses for enduring motor memories. Nature 462, 915; S. B. Hofer et al. (2009) Experience leaves a lasting structural trace in cortical circuits. Nature 457, 313). This increase is thought to represent a "structural trace" of the experience that can serve as a synaptic substrate for more robust and rapid plasticity when the same experience occurs at a later time (E. I. Knudsen et al. (2000) Traces of learning in the auditory localization pathway. Proc Natl Acad Sci USA 97, 11815). For example, monocular deprivation (MD) for 3 days, followed by eye reopening and a second closure of the same eye in adulthood produces significantly more OD plasticity than usual in adult visual cortex (S. B. Hofer et al. (2009) Experience leaves a lasting structural trace in cortical circuits. Nature 457, 313; S. B. Hofer et al. (2006) Prior experience enhances plasticity in adult visual cortex. Nat Neurosci 9, 127). The initial MD causes a significant spine density increase on the apical dendrites of layer 5 (L5) pyramidal neurons in visual cortex (S. B. Hofer et al. (2009), supra) that is maintained after eye reopening (S. B. Hofer et al. (2009), supra; S. B. Hofer et al. (2006), supra).

sPirB infusion might trigger an increase in spine density that could account for the observed enhancement of OD plasticity. To test this hypothesis, visual cortex of wild type Thy-1 YFP-H transgenic mice (G. Feng et al. (2000) Imaging neuronal subsets in transgenic mice expressing multiple spectral variants of GFP. Neuron 28, 41) in which the dendrites and spines of cortical L5 pyramidal neurons are labeled with YFP, received minipump infusion of either sPirB or BSA between P63-74. To determine if de novo spine formation can occur simply with sPirB treatment, no monocular visual deprivation was performed (FIG. 19A, B). Spines on the apical dendrites of L5 pyramidal neurons were examined in the binocular zone at a distance posterior to the infusion site comparable to that studied above for assessment of OD plasticity. In this region following sPirB infusion, pyramidal neuron somata, dendrites and spines appeared intact and healthy, without fragmentation or blebbing (FIG. 19A). Spine density on L5 apical dendritic tufts increases by 38% in the presence of sPirB vs. BSA controls (FIG. 19B). Spine density on L5 neurons in the uninfused hemisphere was not altered. The observed density increase could arise if sPirB acts on a subclass of dendritic spines. However, after 11 day infusion of either sPirB or BSA there was no significant difference in the proportion of spines classified as mushroom, thin, or stubby (K. M. Harris et a. (1992) Three-dimensional structure of dendritic spines and synapses in rat hippocampus (CA1) at postnatal day 15 and adult ages: implications for the maturation of synaptic physiology and long-term potentiation. J Neurosci 12, 2685) (FIG. 22B, P>0.999). Together, results indicate that in adult visual cortex, it is actually possible to generate a local increase in spine density on L5 neurons by infusing sPirB.

To examine if these changes in spine density represent new functional synapses, miniature EPSCs (mEPSCs) were recorded from L5 pyramidal neurons in slices of visual cortex from P70-77 mice, following 7-11 days minipump infusion in vivo (FIG. 19C). mEPSC frequency was significantly increased in sPirB treated animals as compared to BSA treated littermates (FIG. 19D), with no change in mEPSC amplitude (FIG. 19E). This finding is consistent with the idea that there is an increase in synaptic connectivity, suggesting that new spines formed during sPirB infusion represent sites of functional synapses.

Improved structural recovery from long-term monocular deprivation after acute PirB blockade. Prior studies have shown that long term monocular deprivation (LTMD) profoundly decreases visual acuity as well as the number of cortical neurons visually driven by the deprived eye and that there is little if any recovery even with restoration of binocular (T. Pizzorusso et al., (2006) Structural and functional recovery from early monocular deprivation in adult rats. Proc Natl Acad Sci USA 103, 8517; H. Y. He et al. (2007) Experience-dependent recovery of vision following chronic deprivation amblyopia. Nat Neurosci 10, 1134; E. Kang et al., (2013) Visual acuity development and plasticity in the absence of sensory experience. J Neurosci 33, 17789; H. Morishita et al. (2010) Lynx1, a cholinergic brake, limits plasticity in adult visual cortex. Science 330, 1238; K. L. Montey, E. M. Quinlan (2011) Recovery from chronic monocular deprivation following reactivation of thalamocortical plasticity by dark exposure. Nat Commun 2, 317). It has been proposed that the decrease in dendritic spine density known to accompany prolonged visual deprivation underlies these deficits. For example, Quinlan and colleagues (K. L. Montey, E. M. Quinlan (2011), supra) have shown that LTMD generates a significant decline in spine density on basolateral dendrites of L5 pyramidal neurons contralateral to the deprived eye.

Given the remarkable generative effect of sPirB on spine density and mEPSC frequency, we examined if recovery from LTMD—assessed by monitoring spine density along the basolateral dendrites of L5 pyramidal neurons—is facilitated by sPirB infusion. Thy-1 YFP mice were either normally reared or received LTMD from P19-47, spanning the entire critical period for OD plasticity. At P47 the deprived eye was reopened to restore binocular vision, and then at P54 minipumps were implanted contralateral to the deprived eye to infuse either sPirB or BSA until P61 (FIG. 19F). In BSA treated controls, LTMD resulted in a 28% decrease in spine density along L5 basolateral dendrites despite several weeks of subsequent binocular vision (FIG. 19G, H), as expected from previous studies (T. Pizzorusso et al. (2006), supra; K. L. Montey, E. M. Quinlan (2011), supra). In normally-reared littermates infused with sPirB, spine density increased on basolateral dendrites compared to normally-reared BSA infused controls, demonstrating that sPirB infusion can increase spine density not only on apical dendritic tufts of L5 pyramidal neurons, but also on their basolateral dendrites.

Figure 22D:
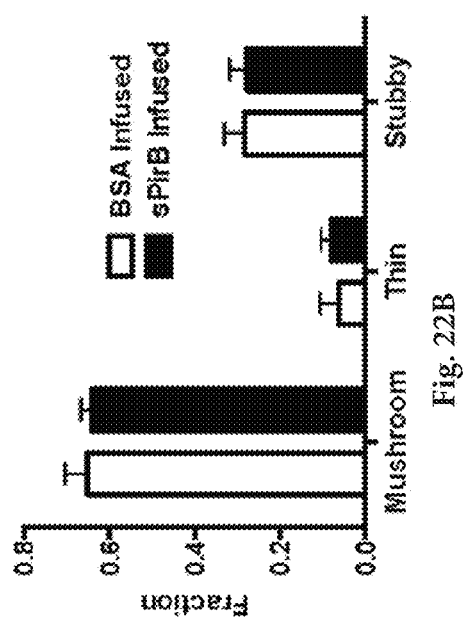

The spine loss accompanying LTMD can be almost entirely reversed by minipump infusion of sPirB. There is a striking 57% increase in basolateral dendritic spine density compared to LTMD BSA-treated controls, essentially restoring spine density to the level of BSA treated controls reared with normal vision (FIG. 19H). However, there was no detectable change in overall distribution of basolateral spine types (FIG. 22D), similar to observations above for L5 apical dendrites. The results of this experiment demonstrate that sPirB can reverse spine loss resulting from LTMD even when infused a week after eye reopening.

Discussion

The results of this study have shown that OD plasticity in visual cortex of adult mice can be enhanced long after critical period closure by acutely disrupting the function of an endogenous receptor: PirB. Mechanistically, blockade of PirB results in increased synaptic density on L5 pyramidal neurons, creating a substrate for additional experience-dependent circuit change even in adulthood. This acutely added cortical plasticity could be recruited to promote recovery from an extended period of developmental monocular deprivation that is usually irreversible even if binocular vision is restored.

Two independent but complementary methods were used—genetic deletion of PirB with temporal control, or blockade of ligand binding using a soluble PirB decoy. Both methods generate enhanced OD plasticity not only during the critical period but also when employed in adulthood. Further, the sPirB minipump infusion experiments reveal that OD plasticity and spine density can be altered specifically, locally within visual cortex, and within 7-11 days. Together, these results indicate that endogenous PirB functions actively to limit mechanisms of structural and functional plasticity throughout life, validating PirB as a target for therapeutic interventions that could improve recovery from injury, correct dysfunctional developmental plasticity, or even temporarily enhance learning in normal individuals.

Mechanism of PirB function involves acute regulation of spine and synapse density. In adulthood, acute deletion or blockade of PirB generates a rapid increase in spine density and mEPSC frequency, and infusion of sPirB following LTMD can rescue spine loss. New sensory experience and motor learning are correlated directly with increases in structural connectivity in a variety of neural structures, including somatosensory (G. Yang, et al. (2009) Stably maintained dendritic spines are associated with lifelong memories. Nature 462, 920), visual (S. B. Hofer et al. (2009) Experience leaves a lasting structural trace in cortical circuits. Nature 457, 313) and motor cortex (T. Xu et al., (2009) Rapid formation and selective stabilization of synapses for enduring motor memories. Nature 462, 915), and optic tectum (E. I. Knudsen et al. (2000) Traces of learning in the auditory localization pathway. Proc Natl Acad Sci USA 97, 11815; B. A. Linkenhoker et al. (2005) Anatomical traces of juvenile learning in the auditory system of adult barn owls. Nat Neurosci 8, 93). Spine density increases also correlate with enhanced subsequent plasticity. Studies of repeated MD have shown that structural traces of prior experience can be co-opted for faster, more robust OD plasticity, particularly on the apical tufts of layer 5 pyramidal neurons (M. Djurisic et al., (2013) PirB regulates a structural substrate for cortical plasticity. Proc Natl Acad Sci USA 110, 20771; 32. S. B. Hofer et al. (2009) Experience leaves a lasting structural trace in cortical circuits. Nature 457, 313; S. B. Hofer et al. (2006) Prior experience enhances plasticity in adult visual cortex. Nat Neurosci 9, 127).

Similarly, implantation of inhibitory neuron progenitors into adult visual cortex induces more numerous, albeit weaker connections and a concomitant increase in OD plasticity (D. G. Southwell et al. (2010) Cortical Plasticity Induced by Inhibitory Neuron Transplantation. Science 327, 1145). Germline deletion of the receptor NgR1, which is thought to share several ligands with PirB (J. K. Atwal et al., (2008) PirB is a Functional Receptor for Myelin Inhibitors of Axonal Regeneration. Science 322, 967), also negatively regulates OD plasticity in adult but not juvenile visual cortex (A. W. McGee et al. (2005) Experience-driven plasticity of visual cortex limited by myelin and Nogo receptor. Science 309, 2222), and acute deletion of NgR1 increases spine turnover but not density in visual and somatosensory cortex (F. V. Akbik et al. (2013) Anatomical plasticity of adult brain is titrated by Nogo Receptor 1. Neuron 77, 859), suggesting a role for spine dynamics as well as density. Furthermore, the enhanced OD plasticity present in germline PirB−/− mice is associated with an 85% increase in spine density on apical dendrites of L5 neurons, as well as with a significant increase in spine stability and enhanced L4 to L2/3 LTP in visual cortex (M. Djurisic et al., (2013) PirB regulates a structural substrate for cortical plasticity. Proc Natl Acad Sci USA 110, 20771). Collectively these experiments strongly connect an increase in spine density and functional connectivity to enhanced OD plasticity. Thus sPirB infusions may act to enhance OD plasticity in WT cortex by creating a more highly interconnected structural substrate for synaptic change that can be accessed when normal visual experience is perturbed by ME or MD.

Long term monocular visual deprivation during the critical period leads to a profound loss of visual acuity, as well as to loss of visual responsiveness of cortical neurons to stimulation of the deprived eye; both are highly resistant to recovery even when binocular vision is subsequently restored. Thus it was striking to find here that LTMD followed by only 7 days of sPirB infusion plus binocular vision is sufficient to generate substantial structural recovery of spine density on basolateral dendrites of L5 neurons, whereas no recovery occurs with control BSA infusions. Prior studies of LTMD have reported spine density decreases on both L2/3 (T. Pizzorusso et al. (2006) Structural and functional recovery from early monocular deprivation in adult rats. Proc Natl Acad Sci USA 103, 8517), as well as on pyramidal neurons throughout cortex (K. L. Montey, E. M. Quinlan (2011) Recovery from chronic monocular deprivation following reactivation of thalamocortical plasticity by dark exposure. Nat Commun 2, 317). Spine loss on cortical pyramidal neurons has been reversed either by suturing closed the formerly open eye and then applying Chondroitinase ABC to digest extracellular matrix (T. Pizzorusso et al. (2006), supra), or by treating animals with 10 days of dark exposure (K. L. Montey, E. M. Quinlan (2011), supra). These treatments are not necessary with sPirB infusion, which is sufficient by itself to bring back spine density values close to normal. This regeneration of spines is highly likely to be accompanied by a restoration of visual function via the deprived eye, given results from many other studies showing this association (T. Pizzorusso et al. (2006), supra; S. B. Hofer et al. (2009) Experience leaves a lasting structural trace in cortical circuits. Nature 457, 313; B. A. Linkenhoker et al. (2005) Anatomical traces of juvenile learning in the auditory system of adult barn owls. Nat Neurosci 8, 93). Indeed, it may even be that some of the exogenous treatments and manipulations including dark rearing mentioned above antagonize PirB downstream signaling, which could explain how they work to alter spine density and restore OD plasticity.

PirB: an endogenous negative regulator of plasticity as a therapeutic target. Here we have shown that disrupting PirB in visual cortex specifically alters signaling that normally represses plasticity, unmasking existing physiological mechanisms that promote plasticity. In contrast, many prior studies have elicited changes in structural and/or functional plasticity by employing interventions proposed to regulate plasticity positively, such as protease treatment, transplanted inhibitory progenitors, GABAergic blockers, growth factors, or transgenic kinase overexpression. Furthermore, such studies often focus on restoring plasticity later in life, whereas disrupting PirB function can enhance plasticity during development as well, thus opening up the possibility for treating neurodevelopmental defects. By generating a recombinant soluble PirB protein and using it to disrupt PirB ligand binding acutely, we have revealed a connection between enhanced plasticity on the one hand and rapid generation of spines and synapses on the other. Our observations add a new dimension to a growing body of research that has unmasked active roles for molecules acting normally in the brain as negative regulators of OD plasticity, including NgR1, Otx2 and Lynx1. In the case of PirB this negative regulation may also be hijacked, as in Alzheimer's disease where amyloid beta oligomers have been shown to bind with nanomolar affinity to PirB, causing deficits in cortical and hippocampal plasticity (see example 1, above). Together these observations imply that acute manipulations of PirB and other endogenous negative regulators can be used therapeutically in both healthy and impaired brains, to engage mechanisms that substantially enhance structural and functional cortical plasticity.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A composition comprising a LILRB2 polypeptide consisting of the first two Ig-like domains of LILRB2, which are residues 24-223 of SEQ ID NO: 3; and an Fc domain.

2. A composition comprising a polypeptide dimer, the dimer comprising: a first polypeptide, which comprises a dimerizing Fc domain fused to a LILRB2 polypeptide consisting of the first two Ig-like domains of LILRB2, which are residues 24-223 of SEQ ID NO: 3; and a second polypeptide, which comprises a dimerizing Fc domain fused to a LILRB2 polypeptide consisting of the first two Ig-like domains LILRB2, which are residues 24-223 of SEQ ID NO: 3.

3. The composition according to claim 2, wherein the dimerizing Fc domain is human IgG1-Fc.

* * * * *

UNITED STATES PATENT AND TRADEMARK OFFICE
CERTIFICATE OF CORRECTION

PATENT NO. : 10,138,286 B2
APPLICATION NO. : 14/772357
DATED : November 27, 2018
INVENTOR(S) : Carla J. Shatz et al.

Page 1 of 1

It is certified that error appears in the above-identified patent and that said Letters Patent is hereby corrected as shown below:

In the Specification

At Column 1, in the paragraph at Line 4 please insert the Government Support Clause so the paragraph reads:
--FEDERALLY SPONSORED RESEARCH AND DEVELOPMENT
This invention was made with Government support under contract EY002858 awarded by the National Institutes of Health. The Government has certain rights in the invention.--

Signed and Sealed this
Fifth Day of March, 2019

Andrei Iancu
*Director of the United States Patent and Trademark Office*